US009057096B2

(12) United States Patent
Liu et al.

(10) Patent No.: US 9,057,096 B2
(45) Date of Patent: Jun. 16, 2015

(54) REGULATION OF WNT/BETA-CATENIN SIGNALING

(75) Inventors: Qingyun Liu, The Woodlands, TX (US); Kendra Carmon, Houston, TX (US); Xing Gong, Pearland, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 160 days.

(21) Appl. No.: 13/475,657

(22) Filed: May 18, 2012

(65) Prior Publication Data

US 2013/0143227 A1 Jun. 6, 2013

Related U.S. Application Data

(60) Provisional application No. 61/488,643, filed on May 20, 2011.

(51) Int. Cl.
*C12Q 1/66* (2006.01)
*G01N 33/53* (2006.01)
*G01N 33/50* (2006.01)

(52) U.S. Cl.
CPC .............. *C12Q 1/66* (2013.01); *G01N 33/5011* (2013.01); *G01N 2333/726* (2013.01)

(58) Field of Classification Search
CPC . C12Q 1/66; G01N 33/5011; G01N 2333/726
See application file for complete search history.

(56) References Cited

U.S. PATENT DOCUMENTS

| | | | |
|---|---|---|---|
| 7,163,799 | B2 | 1/2007 | Liu et al. |
| 2009/0074782 | A1 | 3/2009 | Gurney |
| 2009/0191205 | A1 | 7/2009 | Gurney |

FOREIGN PATENT DOCUMENTS

| | | |
|---|---|---|
| WO | 2009005809 | 1/2009 |
| WO | 2010016766 | 2/2010 |

OTHER PUBLICATIONS

Carmon et al., R-spondins function as ligands of the orphan receptors LGR4 and LGR5 to regulate Wnt/beta-catenin signaling. Proc. Natl. Acad. Sci. U S A Jul. 12, 2011;108(28):11452-11457.*

Glinka et al., LGR4 and LGR5 are R-spondin receptors mediating Wnt/β-catenin and Wnt/PCP signalling.EMBO Sep. 30, 2011;12(10):1055-1061.*

* cited by examiner

*Primary Examiner* — Ruixiang Li

(74) *Attorney, Agent, or Firm* — Jackson Walker L.L.P.

(57) ABSTRACT

A composition and method for detecting the ability of a compound to modulate the activity of LGR4, LGR5, or LGR6 receptors in a cell. LGR4, LGR5, and LGR6 are capable of activating the Wnt/β-catenin signaling system which plays essential roles in embryonic development and in the self-renewal and maintenance of adult stem cells.

4 Claims, 10 Drawing Sheets

A

B

A

B

SEQUENCE LISTING

```
<160> NUMBER OF SEQ ID NOS: 54

<210> SEQ ID NO 1
<211> LENGTH: 27
<212> TYPE: DNA
<213> ORGANISM: Artificial Sequence
<220> FEATURE:
<223> OTHER INFORMATION: Nucleotide sequence of HA tag

<400> SEQUENCE: 1

tacccatacg acgttccaga ctacgct                                        27


<210> SEQ ID NO 2
<211> LENGTH: 9
<212> TYPE: PRT
<213> ORGANISM: Artificial Sequence
<220> FEATURE:
<223> OTHER INFORMATION: Polypeptide sequence of HA tag

<400> SEQUENCE: 2

Tyr Pro Tyr Asp Val Pro Asp Tyr Ala
1               5


<210> SEQ ID NO 3
<211> LENGTH: 30
<212> TYPE: DNA
<213> ORGANISM: Artificial Sequence
<220> FEATURE:
<223> OTHER INFORMATION: Nucleotide sequence of Myc tag

<400> SEQUENCE: 3

gagcagaaac tcatctcaga agaggatctg                                     30


<210> SEQ ID NO 4
<211> LENGTH: 10
<212> TYPE: PRT
<213> ORGANISM: Artificial Sequence
<220> FEATURE:
<223> OTHER INFORMATION: Polypeptide sequence of Myc-tag

<400> SEQUENCE: 4

Glu Gln Lys Leu Ile Ser Glu Glu Asp Leu
1               5                   10


<210> SEQ ID NO 5
<211> LENGTH: 19
<212> TYPE: PRT
<213> ORGANISM: Artificial Sequence
<220> FEATURE:
<223> OTHER INFORMATION: CD8 signal peptide

<400> SEQUENCE: 5

Met Ala Leu Pro Val Thr Ala Leu Leu Leu Pro Leu Ala Leu Leu Leu
1               5                   10                  15

His Ala Ala
```

<210> SEQ ID NO 6
<211> LENGTH: 2662
<212> TYPE: DNA
<213> ORGANISM: Artificial Sequence
<220> FEATURE:
<223> OTHER INFORMATION: Nucleotide sequence encoding the mature form of human LGR5

<400> SEQUENCE: 6

```
ggcagctctc ccaggtctgg tgtgttgctg aggggctgcc ccacacactg tcattgcgag     60
cccgacggca ggatgttgct cagggtggac tgctccgacc tggggctctc ggagctgcct    120
tccaacctca gcgtcttcac ctcctaccta gacctcagta tgaacaacat cagtcagctg    180
ctcccgaatc ccctgcccag tctccgcttc ctggaggagt tacgtcttgc gggaaacgct    240
ctgacataca ttcccaaggg agcattcact ggcctttaca gtcttaaagt tcttatgctg    300
cagaataatc agctaagaca cgtacccaca gaagctctgc agaatttgcg aagccttcaa    360
tccctgcgtc tggatgctaa ccacatcagc tatgtgcccc caagctgttt cagtggcctg    420
cattccctga ggcacctgtg gctggatgac aatgcgttaa cagaaatccc cgtccaggct    480
tttagaagtt tatcggcatt gcaagccatg accttggccc tgaacaaaat acaccacata    540
ccagactatg cctttggaaa cctctccagc ttggtagttc tacatctcca taacaataga    600
atccactccc tgggaaagaa atgctttgat gggctccaca gcctagagac tttagattta    660
aattacaata accttgatga attccccact gcaattagga cactctccaa ccttaaagaa    720
ctaggatttc atagcaacaa tatcaggtcg atacctgaga aagcatttgt aggcaaccct    780
tctcttatta caatacattt ctatgacaat cccatccaat ttgttgggag atctgctttt    840
caacatttac ctgaactaag aacactgact ctgaatggtg cctcacaaat aactgaattt    900
cctgatttaa ctggaactgc aaacctggag agtctgactt taactggagc acagatctca    960
tctcttcctc aaaccgtctg caatcagtta cctaatctcc aagtgctaga tctgtcttac   1020
aacctattag aagatttacc cagtttttca gtctgccaaa agcttcagaa aattgaccta   1080
agacataatg aaatctacga aattaaagtt gacactttcc agcagttgct tagcctccga   1140
tcgctgaatt tggcttggaa caaaattgct attattcacc ccaatgcatt ttccactttg   1200
ccatccctaa taaagctgga cctatcgtcc aacctcctgt cgtcttttcc tataactggg   1260
ttacatggtt taactcactt aaaattaaca ggaaatcatg ccttacagag cttgatatca   1320
tctgaaaact ttccagaact caaggttata gaaatgcctt atgcttacca gtgctgtgca   1380
tttggagtgt gtgagaatgc ctataagatt tctaatcaat ggaataaagg tgacaacagc   1440
agtatggacg accttcataa gaaagatgct ggaatgtttc aggctcaaga tgaacgtgac   1500
cttgaagatt tcctgcttga ctttgaggaa gacctgaaag cccttcattc agtgcagtgt   1560
tcaccttccc caggcccctt caaaccctgt gaacacctgc ttgatggctg gctgatcaga   1620
attggagtgt ggaccatagc agttctggca cttacttgta atgctttggt gacttcaaca   1680
gttttcagat cccctctgta catttccccc attaaactgt taattggggt catcgcagca   1740
gtgaacatgc tcacgggagt ctccagtgcc gtgctggctg gtgtggatgc gttcactttt   1800
ggcagctttg cacgacatgg tgcctggtgg gagaatgggg ttggttgcca tgtcattggt   1860
tttttgtcca tttttgcttc agaatcatct gttttcctgc ttactctggc agccctggag   1920
cgtgggttct ctgcgaaata ttctgcaaaa tttgaaacga aagctccatt ttctagcctg   1980
aaagtaatca ttttgctctg tgccctgctg gccttgacca tggccgcagt tcccctgctg   2040
ggtggcagca agtatggcgc ctcccctctc tgcctgcctt tgccttttgg ggagcccagc   2100
```

```
accatgggct acatggtcgc tctcatcttg ctcaattccc tttgcttcct catgatgacc   2160

attgcctaca ccaagctcta ctgcaatttg gacaagggag acctggagaa tatttgggac   2220

tgctctatgg taaaacacat tgccctgttg ctcttcacca actgcatcct aaactgccct   2280

gtggctttct tgtccttctc ctctttaata aaccttacat ttatcagtcc tgaagtaatt   2340

aagtttatcc ttctggtggt agtcccactt cctgcatgtc tcaatcccct tctctacatc   2400

ttgttcaatc ctcactttaa ggaggatctg gtgagcctga gaaagcaaac ctacgtctgg   2460

acaagatcaa aacacccaag cttgatgtca attaactctg atgatgtcga aaaacagtcc   2520

tgtgactcaa ctcaagcctt ggtaaccttt accagctcca gcatcactta tgacctgcct   2580

cccagttccg tgccatcacc agcttatcca gtgactgaga gctgccatct ttcctctgtg   2640

gcatttgtcc catgtctcta ag                                              2662
```

```
<210> SEQ ID NO 7
<211> LENGTH: 886
<212> TYPE: PRT
<213> ORGANISM: Artificial Sequence
<220> FEATURE:
<223> OTHER INFORMATION: Polypeptide sequence of human LGR5 encoded by
      the above nucleotide sequence

<400> SEQUENCE: 7

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Leu Pro Asn Pro
    50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
            100                 105                 110

Leu Gln Asn Leu Arg Ser Leu Gln Ser Leu Arg Leu Asp Ala Asn His
        115                 120                 125

Ile Ser Tyr Val Pro Pro Ser Cys Phe Ser Gly Leu His Ser Leu Arg
    130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
            180                 185                 190

Val Leu His Leu His Asn Asn Arg Ile His Ser Leu Gly Lys Lys Cys
        195                 200                 205

Phe Asp Gly Leu His Ser Leu Glu Thr Leu Asp Leu Asn Tyr Asn Asn
    210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
                245                 250                 255
```

-continued

```
Val Gly Asn Pro Ser Leu Ile Thr Ile His Phe Tyr Asp Asn Pro Ile
            260                 265                 270

Gln Phe Val Gly Arg Ser Ala Phe Gln His Leu Pro Glu Leu Arg Thr
        275                 280                 285

Leu Thr Leu Asn Gly Ala Ser Gln Ile Thr Glu Phe Pro Asp Leu Thr
    290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
        355                 360                 365

Lys Val Asp Thr Phe Gln Gln Leu Leu Ser Leu Arg Ser Leu Asn Leu
    370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Ile Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
        435                 440                 445

Val Ile Glu Met Pro Tyr Ala Tyr Gln Cys Cys Ala Phe Gly Val Cys
    450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
        515                 520                 525

Pro Cys Glu His Leu Leu Asp Gly Trp Leu Ile Arg Ile Gly Val Trp
    530                 535                 540

Thr Ile Ala Val Leu Ala Leu Thr Cys Asn Ala Leu Val Thr Ser Thr
545                 550                 555                 560

Val Phe Arg Ser Pro Leu Tyr Ile Ser Pro Ile Lys Leu Leu Ile Gly
                565                 570                 575

Val Ile Ala Ala Val Asn Met Leu Thr Gly Val Ser Ser Ala Val Leu
            580                 585                 590

Ala Gly Val Asp Ala Phe Thr Phe Gly Ser Phe Ala Arg His Gly Ala
        595                 600                 605

Trp Trp Glu Asn Gly Val Gly Cys His Val Ile Gly Phe Leu Ser Ile
    610                 615                 620

Phe Ala Ser Glu Ser Ser Val Phe Leu Leu Thr Leu Ala Ala Leu Glu
625                 630                 635                 640

Arg Gly Phe Ser Ala Lys Tyr Ser Ala Lys Phe Glu Thr Lys Ala Pro
                645                 650                 655

Phe Ser Ser Leu Lys Val Ile Ile Leu Leu Cys Ala Leu Leu Ala Leu
            660                 665                 670
```

```
Thr Met Ala Ala Val Pro Leu Leu Gly Gly Ser Lys Tyr Gly Ala Ser
        675                 680                 685

Pro Leu Cys Leu Pro Leu Pro Phe Gly Glu Pro Ser Thr Met Gly Tyr
    690                 695                 700

Met Val Ala Leu Ile Leu Leu Asn Ser Leu Cys Phe Leu Met Met Thr
705                 710                 715                 720

Ile Ala Tyr Thr Lys Leu Tyr Cys Asn Leu Asp Lys Gly Asp Leu Glu
                725                 730                 735

Asn Ile Trp Asp Cys Ser Met Val Lys His Ile Ala Leu Leu Leu Phe
            740                 745                 750

Thr Asn Cys Ile Leu Asn Cys Pro Val Ala Phe Leu Ser Phe Ser Ser
        755                 760                 765

Leu Ile Asn Leu Thr Phe Ile Ser Pro Glu Val Ile Lys Phe Ile Leu
    770                 775                 780

Leu Val Val Val Pro Leu Pro Ala Cys Leu Asn Pro Leu Leu Tyr Ile
785                 790                 795                 800

Leu Phe Asn Pro His Phe Lys Glu Asp Leu Val Ser Leu Arg Lys Gln
                805                 810                 815

Thr Tyr Val Trp Thr Arg Ser Lys His Pro Ser Leu Met Ser Ile Asn
            820                 825                 830

Ser Asp Asp Val Glu Lys Gln Ser Cys Asp Ser Thr Gln Ala Leu Val
        835                 840                 845

Thr Phe Thr Ser Ser Ser Ile Thr Tyr Asp Leu Pro Pro Ser Ser Val
    850                 855                 860

Pro Ser Pro Ala Tyr Pro Val Thr Glu Ser Cys His Leu Ser Ser Val
865                 870                 875                 880

Ala Phe Val Pro Cys Leu
                885
```

<210> SEQ ID NO 8
<211> LENGTH: 2829
<212> TYPE: DNA
<213> ORGANISM: Artificial Sequence
<220> FEATURE:
<223> OTHER INFORMATION: Nucleotide sequence encoding the mature form of human LGR6

<400> SEQUENCE: 8

```
ccccagcccg gcccggggcc caccgcctgc ccggccccct gccactgcca ggaggacggc     60

atcatgctgt ctgccgactg ctctgagctc gggctgtccg ccgttccggg ggacctggac    120

cccctgacgg cttacctgga cctcagcatg aacaacctca cagagcttca gcctggcctc    180

ttccaccacc tgcgcttctt ggaggagctg cgtctctctg ggaaccatct ctcacacatc    240

ccaggacaag cattctctgg tctctacagc ctgaaaatcc tgatgctgca gaacaatcag    300

ctgggaggaa tccccgcaga ggcgctgtgg gagctgccga gcctgcagtc gctgcgccta    360

gatgccaacc tcatctccct ggtcccggag aggagctttg aggggctgtc ctccctccgc    420

cacctctggc tggacgacaa tgcactcacg gagatccctg tcagggccct caacaacctc    480

cctgccctgc aggccatgac cctggccctc aaccgcatca gccacatccc cgactacgcg    540

ttccagaatc tcaccagcct tgtggtgctg catttgcata acaaccgcat ccagcatctg    600

gggacccaca gcttcgaggg gctgcacaat ctggagacac tagacctgaa ttataacaag    660

ctgcaggagt tccctgtggc catccggacc ctgggcagac tgcaggaact ggggttccat    720

aacaacaaca tcaaggccat cccagaaaag gccttcatgg ggaaccctct gctacagacg    780
```

```
atacactttt atgataaccc aatccagttt gtgggaagat cggcattcca gtacctgcct    840

aaactccaca cactatctct gaatggtgcc atggacatcc aggagtttcc agatctcaaa    900

ggcaccacca gcctggagat cctgaccctg acccgcgcag gcatccggct gctcccatcg    960

gggatgtgcc aacagctgcc caggctccga gtcctggaac tgtctcacaa tcaaattgag   1020

gagctgccca gcctgcacag gtgtcagaaa ttggaggaaa tcggcctcca acacaaccgc   1080

atctgggaaa ttggagctga caccttcagc cagctgagct ccctgcaagc cctggatctt   1140

agctggaacg ccatccggtc catccacccc gaggccttct ccaccctgca ctccctggtc   1200

aagctggacc tgacagacaa ccagctgacc acactgcccc tggctggact tgggggcttg   1260

atgcatctga agctcaaagg gaaccttgct ctctcccagg ccttctccaa ggacagtttc   1320

ccaaaactga ggatcctgga ggtgccttat gcctaccagt gctgtcccta tgggatgtgt   1380

gccagcttct tcaaggcctc tgggcagtgg gaggctgaag accttcacct tgatgatgag   1440

gagtcttcaa aaaggcccct gggcctcctt gccagacaag cagagaacca ctatgaccag   1500

gacctggatg agctccagct ggagatggag gactcaaagc cacaccccag tgtccagtgt   1560

agccctactc caggcccctt caagccctgt gagtacctct ttgaaagctg ggcatccgc    1620

ctggccgtgt gggccatcgt gttgctctcc gtgctctgca atggactggt gctgctgacc   1680

gtgttcgctg gcgggcctgt ccccctgccc ccggtcaagt ttgtggtagg tgcgattgca   1740

ggcgccaaca ccttgactgg catttcctgt ggccttctag cctcagtcga tgccctgacc   1800

tttggtcagt tctctgagta cggagcccgc tgggagacgg ggctaggctg ccgggccact   1860

ggcttcctgg cagtacttgg gtcggaggca tcggtgctgc tgctcactct ggccgcagtg   1920

cagtgcagcg tctccgtctc ctgtgtccgg gcctatggga agtccccctc cctgggcagc   1980

gttcgagcag ggtcctaggg ctgcctggca ctggcagggc tggccgccgc gctgcccctg   2040

gcctcagtgg gagaatacgg ggcctcccca ctctgcctgc cctacgcgcc acctgagggt   2100

cagccagcag ccctgggctt caccgtggcc ctggtgatga tgaactcctt ctgtttcctg   2160

gtcgtggccg gtgcctacat caaactgtac tgtgacctgc cgcggggcga ctttgaggcc   2220

gtgtgggact gcgccatggt gaggcacgtg gcctggctca tcttcgcaga cgggctcctc   2280

tactgtcccg tggccttcct cagctttgcc tccatgctgg gcctcttccc tgtcacgccc   2340

gaggccgtca agtctgtcct gctggtggtg ctgcccctgc ctgcctgcct caacccactg   2400

ctgtacctgc tcttcaaccc ccacttccgg gatgaccttc ggcggcttcg gccccgcgca   2460

ggggactcag ggcccctagc ctatgctgcg gccggggagc tggagaagag ctcctgtgat   2520

tctacccagg ccctggtagc cttctctgat gtggatctca ttctggaagc ttctgaagct   2580

gggcggcccc ctgggctgga gacctatggc ttcccctcag tgaccctcat ctcctgtcag   2640

cagccagggg cccccaggct ggagggcagc cattgtgtag agccagaggg gaaccacttt   2700

gggaaccccc aaccctccat ggatggagaa ctgctgctga gggcagaggg atctacgcca   2760

gcaggtggag gcttgtcagg gggtggcggc tttcagccct ctggcttggc ctttgcttca   2820

cacgtgtaa                                                           2829
```

```
<210> SEQ ID NO 9
<211> LENGTH: 942
<212> TYPE: PRT
<213> ORGANISM: Artificial Sequence
<220> FEATURE:
<223> OTHER INFORMATION: Polypeptide sequence of human LGR6 encoded by
      the above nucleotide sequence
```

<400> SEQUENCE: 9

```
Pro Gln Pro Gly Pro Gly Pro Thr Ala Cys Pro Ala Pro Cys His Cys
1               5                   10                  15

Gln Glu Asp Gly Ile Met Leu Ser Ala Asp Cys Ser Glu Leu Gly Leu
            20                  25                  30

Ser Ala Val Pro Gly Asp Leu Asp Pro Leu Thr Ala Tyr Leu Asp Leu
        35                  40                  45

Ser Met Asn Asn Leu Thr Glu Leu Gln Pro Gly Leu Phe His His Leu
    50                  55                  60

Arg Phe Leu Glu Glu Leu Arg Leu Ser Gly Asn His Leu Ser His Ile
65                  70                  75                  80

Pro Gly Gln Ala Phe Ser Gly Leu Tyr Ser Leu Lys Ile Leu Met Leu
                85                  90                  95

Gln Asn Asn Gln Leu Gly Gly Ile Pro Ala Glu Ala Leu Trp Glu Leu
            100                 105                 110

Pro Ser Leu Gln Ser Leu Arg Leu Asp Ala Asn Leu Ile Ser Leu Val
        115                 120                 125

Pro Glu Arg Ser Phe Glu Gly Leu Ser Ser Leu Arg His Leu Trp Leu
    130                 135                 140

Asp Asp Asn Ala Leu Thr Glu Ile Pro Val Arg Ala Leu Asn Asn Leu
145                 150                 155                 160

Pro Ala Leu Gln Ala Met Thr Leu Ala Leu Asn Arg Ile Ser His Ile
                165                 170                 175

Pro Asp Tyr Ala Phe Gln Asn Leu Thr Ser Leu Val Val Leu His Leu
            180                 185                 190

His Asn Asn Arg Ile Gln His Leu Gly Thr His Ser Phe Glu Gly Leu
        195                 200                 205

His Asn Leu Glu Thr Leu Asp Leu Asn Tyr Asn Lys Leu Gln Glu Phe
    210                 215                 220

Pro Val Ala Ile Arg Thr Leu Gly Arg Leu Gln Glu Leu Gly Phe His
225                 230                 235                 240

Asn Asn Asn Ile Lys Ala Ile Pro Glu Lys Ala Phe Met Gly Asn Pro
                245                 250                 255

Leu Leu Gln Thr Ile His Phe Tyr Asp Asn Pro Ile Gln Phe Val Gly
            260                 265                 270

Arg Ser Ala Phe Gln Tyr Leu Pro Lys Leu His Thr Leu Ser Leu Asn
        275                 280                 285

Gly Ala Met Asp Ile Gln Glu Phe Pro Asp Leu Lys Gly Thr Thr Ser
    290                 295                 300

Leu Glu Ile Leu Thr Leu Thr Arg Ala Gly Ile Arg Leu Leu Pro Ser
305                 310                 315                 320

Gly Met Cys Gln Gln Leu Pro Arg Leu Arg Val Leu Glu Leu Ser His
                325                 330                 335

Asn Gln Ile Glu Glu Leu Pro Ser Leu His Arg Cys Gln Lys Leu Glu
            340                 345                 350

Glu Ile Gly Leu Gln His Asn Arg Ile Trp Glu Ile Gly Ala Asp Thr
        355                 360                 365

Phe Ser Gln Leu Ser Ser Leu Gln Ala Leu Asp Leu Ser Trp Asn Ala
    370                 375                 380

Ile Arg Ser Ile His Pro Glu Ala Phe Ser Thr Leu His Ser Leu Val
385                 390                 395                 400

Lys Leu Asp Leu Thr Asp Asn Gln Leu Thr Thr Leu Pro Leu Ala Gly
                405                 410                 415
```

```
Leu Gly Gly Leu Met His Leu Lys Leu Lys Gly Asn Leu Ala Leu Ser
            420                 425                 430

Gln Ala Phe Ser Lys Asp Ser Phe Pro Lys Leu Arg Ile Leu Glu Val
        435                 440                 445

Pro Tyr Ala Tyr Gln Cys Cys Pro Tyr Gly Met Cys Ala Ser Phe Phe
    450                 455                 460

Lys Ala Ser Gly Gln Trp Glu Ala Glu Asp Leu His Leu Asp Asp Glu
465                 470                 475                 480

Glu Ser Ser Lys Arg Pro Leu Gly Leu Leu Ala Arg Gln Ala Glu Asn
                485                 490                 495

His Tyr Asp Gln Asp Leu Asp Glu Leu Gln Leu Glu Met Glu Asp Ser
            500                 505                 510

Lys Pro His Pro Ser Val Gln Cys Ser Pro Thr Pro Gly Pro Phe Lys
        515                 520                 525

Pro Cys Glu Tyr Leu Phe Glu Ser Trp Gly Ile Arg Leu Ala Val Trp
    530                 535                 540

Ala Ile Val Leu Leu Ser Val Leu Cys Asn Gly Leu Val Leu Leu Thr
545                 550                 555                 560

Val Phe Ala Gly Gly Pro Val Pro Leu Pro Pro Val Lys Phe Val Val
                565                 570                 575

Gly Ala Ile Ala Gly Ala Asn Thr Leu Thr Gly Ile Ser Cys Gly Leu
            580                 585                 590

Leu Ala Ser Val Asp Ala Leu Thr Phe Gly Gln Phe Ser Glu Tyr Gly
        595                 600                 605

Ala Arg Trp Glu Thr Gly Leu Gly Cys Arg Ala Thr Gly Phe Leu Ala
    610                 615                 620

Val Leu Gly Ser Glu Ala Ser Val Leu Leu Leu Thr Leu Ala Ala Val
625                 630                 635                 640

Gln Cys Ser Val Ser Val Ser Cys Val Arg Ala Tyr Gly Lys Ser Pro
                645                 650                 655

Ser Leu Gly Ser Val Arg Ala Gly Val Leu Gly Cys Leu Ala Leu Ala
            660                 665                 670

Gly Leu Ala Ala Ala Leu Pro Leu Ala Ser Val Gly Glu Tyr Gly Ala
        675                 680                 685

Ser Pro Leu Cys Leu Pro Tyr Ala Pro Pro Glu Gly Gln Pro Ala Ala
    690                 695                 700

Leu Gly Phe Thr Val Ala Leu Val Met Met Asn Ser Phe Cys Phe Leu
705                 710                 715                 720

Val Val Ala Gly Ala Tyr Ile Lys Leu Tyr Cys Asp Leu Pro Arg Gly
                725                 730                 735

Asp Phe Glu Ala Val Trp Asp Cys Ala Met Val Arg His Val Ala Trp
            740                 745                 750

Leu Ile Phe Ala Asp Gly Leu Leu Tyr Cys Pro Val Ala Phe Leu Ser
        755                 760                 765

Phe Ala Ser Met Leu Gly Leu Phe Pro Val Thr Pro Glu Ala Val Lys
    770                 775                 780

Ser Val Leu Leu Val Val Leu Pro Leu Pro Ala Cys Leu Asn Pro Leu
785                 790                 795                 800

Leu Tyr Leu Leu Phe Asn Pro His Phe Arg Asp Asp Leu Arg Arg Leu
                805                 810                 815

Arg Pro Arg Ala Gly Asp Ser Gly Pro Leu Ala Tyr Ala Ala Ala Gly
            820                 825                 830
```

```
Glu Leu Glu Lys Ser Ser Cys Asp Ser Thr Gln Ala Leu Val Ala Phe
        835                 840                 845

Ser Asp Val Asp Leu Ile Leu Glu Ala Ser Glu Ala Gly Arg Pro Pro
    850                 855                 860

Gly Leu Glu Thr Tyr Gly Phe Pro Ser Val Thr Leu Ile Ser Cys Gln
865                 870                 875                 880

Gln Pro Gly Ala Pro Arg Leu Glu Gly Ser His Cys Val Glu Pro Glu
                885                 890                 895

Gly Asn His Phe Gly Asn Pro Gln Pro Ser Met Asp Gly Glu Leu Leu
            900                 905                 910

Leu Arg Ala Glu Gly Ser Thr Pro Ala Gly Gly Gly Leu Ser Gly Gly
        915                 920                 925

Gly Gly Phe Gln Pro Ser Gly Leu Ala Phe Ala Ser His Val
    930                 935                 940


<210> SEQ ID NO 10
<211> LENGTH: 24
<212> TYPE: DNA
<213> ORGANISM: Artificial Sequence
<220> FEATURE:
<223> OTHER INFORMATION: Nucleotide sequence of FLAG tag

<400> SEQUENCE: 10

gattacaagg atgacgacga taag                                              24


<210> SEQ ID NO 11
<211> LENGTH: 8
<212> TYPE: PRT
<213> ORGANISM: Artificial Sequence
<220> FEATURE:
<223> OTHER INFORMATION: Polypeptide sequence of FLAG tag

<400> SEQUENCE: 11

Asp Tyr Lys Asp Asp Asp Asp Lys
1               5


<210> SEQ ID NO 12
<211> LENGTH: 2787
<212> TYPE: DNA
<213> ORGANISM: Artificial Sequence
<220> FEATURE:
<223> OTHER INFORMATION: Nucleotide sequence encoding the mature form of
      mouse LGR4

<400> SEQUENCE: 12

gctgcgccac ctctctgcgc tgcgccctgc agctgcgacg gcgaccgtcg ggtggactgc     60

tccgggaagg ggttgacggc ggtaccggag gggctcagcg ccttcaccca agcactggat    120

atcagtatga acaatatcac tcagttacca gaagatgcat ttaagaattt tccttttcta    180

gaggagctac aactggctgg taacgacctt tcttttatcc acccaaaagc cttgtctggg    240

ttgaaagaac tcaaagtcct aaccctccag aacaatcagt tgaaaacagt acccagtgaa    300

gccattcgtg gactgagtgc tttgcagtct ctacgcttag atgccaacca tattacctca    360

gtccccggagg acagttttga agggctcgtt cagttgcggc atctgtggct ggatgacaac    420

atcttgacgg aagtgcctgt gcgtccgctc agcaacctgc caaccctgca ggcgctgacc    480

ttggctctca acaacatctc aagcatcccc gacttcgcat tcaccaacct ttcaagcttg    540

gtagtgctgc atcttcataa caataaaatt aaaagcctca gtcaacactg ttttgatgga    600

ctagataacc tggaaaccct ggacttgaat tataataact tggatgaatt tcctcaggct    660
```

```
attaaagccc ttcccagcct taaagagctg ggatttcaca gtaattctat ttctgttatc    720
ccggatggag catttgctgg taatccactg ctaagaacta tccatttgta tgataatcct    780
ctgtcttttg tggggaactc agcatttcac aacctgtctg atctgcattc cttagtcatt    840
cgtggtgcaa gcctggtgca gtggttcccc aatctggccg gaactgtcca tctggagagt    900
ctaaccttga cagggacaaa aataagcagc atacctgatg atctgtgcca aaaccaaaag    960
atgctgcgga ctctggactt atcttataac gatataagag accttccaag ttttaatggt   1020
tgtcgtgcat tggaagaaat ttcattgcag cgtaatcaaa tctccctgat aaaggaaact   1080
acttttcaag gcctaacatc cctaaggatt ctagatctga gtagaaacct gattcgtgaa   1140
attcacagtg gagcttttgc gaagcttggg acaattacta acctggatgt gagtttcaat   1200
gaattaacct catttcctac ggaaggcctg aatgggctca atcaacttaa acttgtgggt   1260
aacttccagc tgaaagatgc cttggcagcc agagactttg ccaatctcag gtctctatca   1320
gtaccatatg cttatcagtg ttgtgcattt tgggggtgtg actcttatgc aaatttaaac   1380
acagaagata acagcccccca agaccacagt gtgacaaaag agaaaggtgc tacagatgca   1440
gcaaatgcca ccagcactgc tgaaagtgaa gaacatagcc aaataatcat ccattgtaca   1500
ccttcaacag gtgcttttaa gccctgtgaa tatttactgg gaagctggat gattcgcctt   1560
acagtgtggt tcattttcct ggtcgccttg cttttcaacc tgcttgtcat tttaacagtg   1620
tttgcgtctt gttcatcact gcctgcctcc aagctcttca taggcttgat ttctgtgtct   1680
aacttactca tgggcatcta tactggcatc cttacttttc ttgatgctgt gtcctggggc   1740
cgatttgctg aatttggcat ttggtgggaa actggcagcg gctgcaaggt agctgggtct   1800
ctggcagtct tctcctcaga gagcgccgta ttcctgttaa ccctggcagc cgtggaaaga   1860
agcgtttttg caaaggatgt aatgaaaaat gggaaaagca gtcacctccg acagttccag   1920
gtggctgccc tcgtagcttt gctgggtgct gcaatagcag gctgcttccc cctttttcac   1980
ggagggcaat attctgcatc acccttgtgc ttgccatttc ctacaggaga gacaccatca   2040
ttaggattca ctgtgaccct agtgctatta aactcactag cattttttatt gatggccatt  2100
atctacacta aactctactg caacttagag aaagaagacc cgtcagaaaa ctcccagtct   2160
agcatgatta agcacgttgc ttggctcatc ttcacaaact gcatcttctt ctgccctgtt   2220
gcatttttct cattcgcacc attgatcacg gcaatctcca tcagccccga gataatgaag   2280
tctgttacgc tgatattctt cccgctgcct gcttgcctga atccagtcct gtacgttttc   2340
ttcaacccaa agtttaaaga cgactggaag ctcctgaagc ggcgtgtcac caggaaacac   2400
ggatcagtct cagtctccat cagcagccaa ggcggttgtg gggaacagga tttctactac   2460
gactgtggca tgtattccca cttgcagggt aacctgactg tctgtgactg ctgtgagtca   2520
tttcttctga caaaaccagt atcgtgcaaa cacttaataa aatcgcacag ttgtcctgta   2580
ttgacagtgg cctcttgcca gaggccagag gcctactggt ctgattgtgg cacacagtcg   2640
gcccattctg actatgcaga tgaagaggat tcctttgtct cggacagctc tgaccaggtg   2700
caggcctgtg gacgagcctg cttctaccag agtcgcggat tccctctggt gcgctatgct   2760
tataatctac cgagagtcag agactga                                       2787
```

<210> SEQ ID NO 13
<211> LENGTH: 928
<212> TYPE: PRT
<213> ORGANISM: Artificial Sequence
<220> FEATURE:
<223> OTHER INFORMATION: Polypeptide sequence of mouse LGR4 encoded by the above nucleotide sequence

<400> SEQUENCE: 13

```
Ala Ala Pro Pro Leu Cys Ala Ala Pro Cys Ser Cys Asp Gly Asp Arg
1               5                   10                  15

Arg Val Asp Cys Ser Gly Lys Gly Leu Thr Ala Val Pro Glu Gly Leu
            20                  25                  30

Ser Ala Phe Thr Gln Ala Leu Asp Ile Ser Met Asn Asn Ile Thr Gln
        35                  40                  45

Leu Pro Glu Asp Ala Phe Lys Asn Phe Pro Phe Leu Glu Glu Leu Gln
    50                  55                  60

Leu Ala Gly Asn Asp Leu Ser Phe Ile His Pro Lys Ala Leu Ser Gly
65                  70                  75                  80

Leu Lys Glu Leu Lys Val Leu Thr Leu Gln Asn Asn Gln Leu Lys Thr
                85                  90                  95

Val Pro Ser Glu Ala Ile Arg Gly Leu Ser Ala Leu Gln Ser Leu Arg
            100                 105                 110

Leu Asp Ala Asn His Ile Thr Ser Val Pro Glu Asp Ser Phe Glu Gly
        115                 120                 125

Leu Val Gln Leu Arg His Leu Trp Leu Asp Asp Asn Ile Leu Thr Glu
    130                 135                 140

Val Pro Val Arg Pro Leu Ser Asn Leu Pro Thr Leu Gln Ala Leu Thr
145                 150                 155                 160

Leu Ala Leu Asn Asn Ile Ser Ser Ile Pro Asp Phe Ala Phe Thr Asn
                165                 170                 175

Leu Ser Ser Leu Val Val Leu His Leu His Asn Asn Lys Ile Lys Ser
            180                 185                 190

Leu Ser Gln His Cys Phe Asp Gly Leu Asp Asn Leu Glu Thr Leu Asp
        195                 200                 205

Leu Asn Tyr Asn Asn Leu Asp Glu Phe Pro Gln Ala Ile Lys Ala Leu
    210                 215                 220

Pro Ser Leu Lys Glu Leu Gly Phe His Ser Asn Ser Ile Ser Val Ile
225                 230                 235                 240

Pro Asp Gly Ala Phe Ala Gly Asn Pro Leu Leu Arg Thr Ile His Leu
                245                 250                 255

Tyr Asp Asn Pro Leu Ser Phe Val Gly Asn Ser Ala Phe His Asn Leu
            260                 265                 270

Ser Asp Leu His Ser Leu Val Ile Arg Gly Ala Ser Leu Val Gln Trp
        275                 280                 285

Phe Pro Asn Leu Ala Gly Thr Val His Leu Glu Ser Leu Thr Leu Thr
    290                 295                 300

Gly Thr Lys Ile Ser Ser Ile Pro Asp Asp Leu Cys Gln Asn Gln Lys
305                 310                 315                 320

Met Leu Arg Thr Leu Asp Leu Ser Tyr Asn Asp Ile Arg Asp Leu Pro
                325                 330                 335

Ser Phe Asn Gly Cys Arg Ala Leu Glu Glu Ile Ser Leu Gln Arg Asn
            340                 345                 350

Gln Ile Ser Leu Ile Lys Glu Thr Thr Phe Gln Gly Leu Thr Ser Leu
        355                 360                 365

Arg Ile Leu Asp Leu Ser Arg Asn Leu Ile Arg Glu Ile His Ser Gly
    370                 375                 380

Ala Phe Ala Lys Leu Gly Thr Ile Thr Asn Leu Asp Val Ser Phe Asn
385                 390                 395                 400
```

```
Glu Leu Thr Ser Phe Pro Thr Glu Gly Leu Asn Gly Leu Asn Gln Leu
                405                 410                 415

Lys Leu Val Gly Asn Phe Gln Leu Lys Asp Ala Leu Ala Ala Arg Asp
            420                 425                 430

Phe Ala Asn Leu Arg Ser Leu Ser Val Pro Tyr Ala Tyr Gln Cys Cys
        435                 440                 445

Ala Phe Trp Gly Cys Asp Ser Tyr Ala Asn Leu Asn Thr Glu Asp Asn
    450                 455                 460

Ser Pro Gln Asp His Ser Val Thr Lys Glu Lys Gly Ala Thr Asp Ala
465                 470                 475                 480

Ala Asn Ala Thr Ser Thr Ala Glu Ser Glu Glu His Ser Gln Ile Ile
                485                 490                 495

Ile His Cys Thr Pro Ser Thr Gly Ala Phe Lys Pro Cys Glu Tyr Leu
            500                 505                 510

Leu Gly Ser Trp Met Ile Arg Leu Thr Val Trp Phe Ile Phe Leu Val
        515                 520                 525

Ala Leu Leu Phe Asn Leu Leu Val Ile Leu Thr Val Phe Ala Ser Cys
    530                 535                 540

Ser Ser Leu Pro Ala Ser Lys Leu Phe Ile Gly Leu Ile Ser Val Ser
545                 550                 555                 560

Asn Leu Leu Met Gly Ile Tyr Thr Gly Ile Leu Thr Phe Leu Asp Ala
                565                 570                 575

Val Ser Trp Gly Arg Phe Ala Glu Phe Gly Ile Trp Trp Glu Thr Gly
            580                 585                 590

Ser Gly Cys Lys Val Ala Gly Ser Leu Ala Val Phe Ser Ser Glu Ser
        595                 600                 605

Ala Val Phe Leu Leu Thr Leu Ala Ala Val Glu Arg Ser Val Phe Ala
    610                 615                 620

Lys Asp Val Met Lys Asn Gly Lys Ser Ser His Leu Arg Gln Phe Gln
625                 630                 635                 640

Val Ala Ala Leu Val Ala Leu Leu Gly Ala Ala Ile Ala Gly Cys Phe
                645                 650                 655

Pro Leu Phe His Gly Gly Gln Tyr Ser Ala Ser Pro Leu Cys Leu Pro
            660                 665                 670

Phe Pro Thr Gly Glu Thr Pro Ser Leu Gly Phe Thr Val Thr Leu Val
        675                 680                 685

Leu Leu Asn Ser Leu Ala Phe Leu Leu Met Ala Ile Ile Tyr Thr Lys
    690                 695                 700

Leu Tyr Cys Asn Leu Glu Lys Glu Asp Pro Ser Glu Asn Ser Gln Ser
705                 710                 715                 720

Ser Met Ile Lys His Val Ala Trp Leu Ile Phe Thr Asn Cys Ile Phe
                725                 730                 735

Phe Cys Pro Val Ala Phe Phe Ser Phe Ala Pro Leu Ile Thr Ala Ile
            740                 745                 750

Ser Ile Ser Pro Glu Ile Met Lys Ser Val Thr Leu Ile Phe Phe Pro
        755                 760                 765

Leu Pro Ala Cys Leu Asn Pro Val Leu Tyr Val Phe Phe Asn Pro Lys
    770                 775                 780

Phe Lys Asp Asp Trp Lys Leu Leu Lys Arg Arg Val Thr Arg Lys His
785                 790                 795                 800

Gly Ser Val Ser Val Ser Ile Ser Ser Gln Gly Gly Cys Gly Glu Gln
                805                 810                 815

Asp Phe Tyr Tyr Asp Cys Gly Met Tyr Ser His Leu Gln Gly Asn Leu
```

```
            820                 825                 830

Thr Val Cys Asp Cys Cys Glu Ser Phe Leu Leu Thr Lys Pro Val Ser
        835                 840                 845

Cys Lys His Leu Ile Lys Ser His Ser Cys Pro Val Leu Thr Val Ala
    850                 855                 860

Ser Cys Gln Arg Pro Glu Ala Tyr Trp Ser Asp Cys Gly Thr Gln Ser
865                 870                 875                 880

Ala His Ser Asp Tyr Ala Asp Glu Glu Asp Ser Phe Val Ser Asp Ser
                885                 890                 895

Ser Asp Gln Val Gln Ala Cys Gly Arg Ala Cys Phe Tyr Gln Ser Arg
            900                 905                 910

Gly Phe Pro Leu Val Arg Tyr Ala Tyr Asn Leu Pro Arg Val Arg Asp
        915                 920                 925


<210> SEQ ID NO 14
<211> LENGTH: 2790
<212> TYPE: DNA
<213> ORGANISM: Artificial Sequence
<220> FEATURE:
<223> OTHER INFORMATION: Nucleic acid sequence encoding the mature form
      of human LGR4

<400> SEQUENCE: 14

ggcgcggcgc cgcctctctg cgcggcgccc tgcagctgcg acggcgaccg tcgggtggac     60

tgctccggga aggggctgac ggccgtgccc gaggggctca gcgccttcac ccaagcgctg    120

gatatcagta tgaacaacat tactcagttg ccagaagatg catttaagaa ctttcctttt    180

ctagaagagc tacaattggc gggcaacgac ctttctttta tccacccaaa ggccttgtct    240

gggttgaaag aactcaaagt tctaacgctc cagaataatc agttgaaaac agtacccagt    300

gaagccattc gagggctgag tgctttgcag tctttgcgtt tagatgccaa ccatattacc    360

tcagtccccg aggacagttt tgaaggactt gttcagttac ggcatctgtg gctggatgac    420

aacagcttga cggaggtgcc tgtgcacccc ctcagcaatc tgcccaccct acaggcgctg    480

accctggctc tcaacaagat ctcaagcatc cctgactttg catttaccaa cctttcaagc    540

ctggtagttc tgcatcttca taacaataaa attagaagcc tgagtcaaca ctgttttgat    600

ggactagata acctggagac cttagacttg aattataata acttggggga atttcctcag    660

gctattaaag cccttcctag ccttaaagag ctaggatttc atagtaattc tatttctgtt    720

atccctgatg gagcatttga tggtaatcca ctcttaagaa ctatacattt gtatgataat    780

cctctgtctt ttgtggggaa ctcagcattt cacaatttat ctgatcttca ttccctagtc    840

attcgtggtg caagcatggt gcagcagttc cccaatctta caggaactgt ccacctggaa    900

agtctgactt tgacaggtac aaagataagc agcataccta ataatttgtg tcaagaacaa    960

aagatgctta ggactttgga cttgtcttac aataatataa gagaccttcc aagttttaat   1020

ggttgccatg ctctggaaga aatttcttta cagcgtaatc aaatctacca aataaaggaa   1080

ggcacctttc aaggcctgat atctctaagg attctagatc tgagtagaaa cctgatacat   1140

gaaattcaca gtagagcttt tgccacactt gggccaataa ctaacctaga tgtaagtttc   1200

aatgaattaa cttcctttcc tacggaaggc ctgaatgggc taaatcaact gaaacttgtg   1260

ggcaacttca agctgaaaga agccttagca gcaaaagact ttgttaacct caggtcttta   1320

tcagtaccat atgcttatca gtgctgtgca ttttggggtt gtgactctta tgcaaattta   1380

aacacagaag ataacagcct ccaggaccac agtgtggcac aggagaaagg tactgctgat   1440
```

```
gcagcaaatg tcacaagcac tcttgaaaat gaagaacata gtcaaataat tatccattgt   1500

acaccttcaa caggtgcttt taagccctgt gaatatttac tgggaagctg gatgattcgt   1560

cttactgtgt ggttcatttt cttggttgca ttatttttca acctgcttgt tattttaaca   1620

acatttgcat cttgtacatc actgccttcg tccaaattgt ttataggctt gatttctgtg   1680

tctaacttat tcatgggaat ctatactggc atcctaactt ttcttgatgc tgtgtcctgg   1740

ggcagattcg ctgaatttgg catttggtgg gaaactggca gtggctgcaa agtagctggg   1800

tttcttgcag ttttctcctc agaaagtgcc atattttat taatgctagc aactgtcgaa   1860

agaagcttat ctgcaaaaga tataatgaaa aatgggaaga gcaatcatct caaacagttc   1920

cgggttgctg cccttttggc tttcctaggt gctacagtag caggctgttt tcccctttc   1980

catagagggg aatattctgc atcacccctt tgtttgccat ttcctacagg tgaaacgcca   2040

tcattaggat tcactgtaac gttagtgcta ttaaactcac tagcattttt attaatggcc   2100

gttatctaca ctaagctata ctgcaacttg gaaaaagagg acctctcaga aaactcacaa   2160

tctagcatga ttaagcatgt cgcttggcta atcttcacca attgcatctt tttctgccct   2220

gtggcgtttt tttcatttgc accattgatc actgcaatct ctatcagccc cgaaataatg   2280

aagtctgtta ctctgatatt ttttccattg cctgcttgcc tgaatccagt cctgtatgtt   2340

ttcttcaacc caaagtttaa agaagactgg aagttactga agcgacgtgt taccaagaaa   2400

agtggatcag tttcagtttc catcagtagc caaggtggtt gtctggaaca ggatttctac   2460

tacgactgtg gcatgtactc acatttgcag ggcaacctga ctgtttgcga ctgctgcgaa   2520

tcgtttcttt taacaaagcc agtatcatgc aaacacttga taaaatcaca cagctgtcct   2580

gcattggcag tggcttcttg ccaaagacct gagggctact ggtccgactg tggcacacag   2640

tcggcccact ctgattatgc agatgaagaa gattcctttg tctcagacag ttctgaccag   2700

gtgcaggcct gtggacgagc ctgcttctac cagagtagag gattcccttt ggtgcgctat   2760

gcttacaatc taccaagagt taaagactga                                    2790
```

```
<210> SEQ ID NO 15
<211> LENGTH: 928
<212> TYPE: PRT
<213> ORGANISM: Artificial Sequence
<220> FEATURE:
<223> OTHER INFORMATION: Polypeptide sequence of human LGR4 encoded by
      the above nucleotide sequence

<400> SEQUENCE: 15

Ala Ala Pro Pro Leu Cys Ala Ala Pro Cys Ser Cys Asp Gly Asp Arg
1               5                   10                  15

Arg Val Asp Cys Ser Gly Lys Gly Leu Thr Ala Val Pro Glu Gly Leu
            20                  25                  30

Ser Ala Phe Thr Gln Ala Leu Asp Ile Ser Met Asn Asn Ile Thr Gln
        35                  40                  45

Leu Pro Glu Asp Ala Phe Lys Asn Phe Pro Phe Leu Glu Glu Leu Gln
    50                  55                  60

Leu Ala Gly Asn Asp Leu Ser Phe Ile His Pro Lys Ala Leu Ser Gly
65                  70                  75                  80

Leu Lys Glu Leu Lys Val Leu Thr Leu Gln Asn Asn Gln Leu Lys Thr
                85                  90                  95

Val Pro Ser Glu Ala Ile Arg Gly Leu Ser Ala Leu Gln Ser Leu Arg
            100                 105                 110

Leu Asp Ala Asn His Ile Thr Ser Val Pro Glu Asp Ser Phe Glu Gly
```

```
        115                 120                 125

Leu Val Gln Leu Arg His Leu Trp Leu Asp Asp Asn Ser Leu Thr Glu
    130                 135                 140

Val Pro Val His Pro Leu Ser Asn Leu Pro Thr Leu Gln Ala Leu Thr
145                 150                 155                 160

Leu Ala Leu Asn Lys Ile Ser Ser Ile Pro Asp Phe Ala Phe Thr Asn
                165                 170                 175

Leu Ser Ser Leu Val Val Leu His Leu His Asn Asn Lys Ile Arg Ser
            180                 185                 190

Leu Ser Gln His Cys Phe Asp Gly Leu Asp Asn Leu Glu Thr Leu Asp
        195                 200                 205

Leu Asn Tyr Asn Asn Leu Gly Glu Phe Pro Gln Ala Ile Lys Ala Leu
    210                 215                 220

Pro Ser Leu Lys Glu Leu Gly Phe His Ser Asn Ser Ile Ser Val Ile
225                 230                 235                 240

Pro Asp Gly Ala Phe Asp Gly Asn Pro Leu Leu Arg Thr Ile His Leu
                245                 250                 255

Tyr Asp Asn Pro Leu Ser Phe Val Gly Asn Ser Ala Phe His Asn Leu
            260                 265                 270

Ser Asp Leu His Ser Leu Val Ile Arg Gly Ala Ser Met Val Gln Gln
        275                 280                 285

Phe Pro Asn Leu Thr Gly Thr Val His Leu Glu Ser Leu Thr Leu Thr
    290                 295                 300

Gly Thr Lys Ile Ser Ser Ile Pro Asn Asn Leu Cys Gln Glu Gln Lys
305                 310                 315                 320

Met Leu Arg Thr Leu Asp Leu Ser Tyr Asn Asn Ile Arg Asp Leu Pro
                325                 330                 335

Ser Phe Asn Gly Cys His Ala Leu Glu Glu Ile Ser Leu Gln Arg Asn
            340                 345                 350

Gln Ile Tyr Gln Ile Lys Glu Gly Thr Phe Gln Gly Leu Ile Ser Leu
        355                 360                 365

Arg Ile Leu Asp Leu Ser Arg Asn Leu Ile His Glu Ile His Ser Arg
    370                 375                 380

Ala Phe Ala Thr Leu Gly Pro Ile Thr Asn Leu Asp Val Ser Phe Asn
385                 390                 395                 400

Glu Leu Thr Ser Phe Pro Thr Glu Gly Leu Asn Gly Leu Asn Gln Leu
                405                 410                 415

Lys Leu Val Gly Asn Phe Lys Leu Lys Glu Ala Leu Ala Ala Lys Asp
            420                 425                 430

Phe Val Asn Leu Arg Ser Leu Ser Val Pro Tyr Ala Tyr Gln Cys Cys
        435                 440                 445

Ala Phe Trp Gly Cys Asp Ser Tyr Ala Asn Leu Asn Thr Glu Asp Asn
    450                 455                 460

Ser Leu Gln Asp His Ser Val Ala Gln Glu Lys Gly Thr Ala Asp Ala
465                 470                 475                 480

Ala Asn Val Thr Ser Thr Leu Glu Asn Glu Glu His Ser Gln Ile Ile
                485                 490                 495

Ile His Cys Thr Pro Ser Thr Gly Ala Phe Lys Pro Cys Glu Tyr Leu
            500                 505                 510

Leu Gly Ser Trp Met Ile Arg Leu Thr Val Trp Phe Ile Phe Leu Val
        515                 520                 525

Ala Leu Phe Phe Asn Leu Leu Val Ile Leu Thr Thr Phe Ala Ser Cys
    530                 535                 540
```

```
Thr Ser Leu Pro Ser Ser Lys Leu Phe Ile Gly Leu Ile Ser Val Ser
545                 550                 555                 560

Asn Leu Phe Met Gly Ile Tyr Thr Gly Ile Leu Thr Phe Leu Asp Ala
                565                 570                 575

Val Ser Trp Gly Arg Phe Ala Glu Phe Gly Ile Trp Trp Glu Thr Gly
            580                 585                 590

Ser Gly Cys Lys Val Ala Gly Phe Leu Ala Val Phe Ser Ser Glu Ser
        595                 600                 605

Ala Ile Phe Leu Leu Met Leu Ala Thr Val Glu Arg Ser Leu Ser Ala
    610                 615                 620

Lys Asp Ile Met Lys Asn Gly Lys Ser Asn His Leu Lys Gln Phe Arg
625                 630                 635                 640

Val Ala Ala Leu Leu Ala Phe Leu Gly Ala Thr Val Ala Gly Cys Phe
                645                 650                 655

Pro Leu Phe His Arg Gly Glu Tyr Ser Ala Ser Pro Leu Cys Leu Pro
            660                 665                 670

Phe Pro Thr Gly Glu Thr Pro Ser Leu Gly Phe Thr Val Thr Leu Val
        675                 680                 685

Leu Leu Asn Ser Leu Ala Phe Leu Leu Met Ala Val Ile Tyr Thr Lys
    690                 695                 700

Leu Tyr Cys Asn Leu Glu Lys Glu Asp Leu Ser Glu Asn Ser Gln Ser
705                 710                 715                 720

Ser Met Ile Lys His Val Ala Trp Leu Ile Phe Thr Asn Cys Ile Phe
                725                 730                 735

Phe Cys Pro Val Ala Phe Phe Ser Phe Ala Pro Leu Ile Thr Ala Ile
            740                 745                 750

Ser Ile Ser Pro Glu Ile Met Lys Ser Val Thr Leu Ile Phe Phe Pro
        755                 760                 765

Leu Pro Ala Cys Leu Asn Pro Val Leu Tyr Val Phe Phe Asn Pro Lys
    770                 775                 780

Phe Lys Glu Asp Trp Lys Leu Leu Lys Arg Arg Val Thr Lys Lys Ser
785                 790                 795                 800

Gly Ser Val Ser Val Ser Ile Ser Ser Gln Gly Gly Cys Leu Glu Gln
                805                 810                 815

Asp Phe Tyr Tyr Asp Cys Gly Met Tyr Ser His Leu Gln Gly Asn Leu
            820                 825                 830

Thr Val Cys Asp Cys Cys Glu Ser Phe Leu Leu Thr Lys Pro Val Ser
        835                 840                 845

Cys Lys His Leu Ile Lys Ser His Ser Cys Pro Ala Leu Ala Val Ala
    850                 855                 860

Ser Cys Gln Arg Pro Glu Gly Tyr Trp Ser Asp Cys Gly Thr Gln Ser
865                 870                 875                 880

Ala His Ser Asp Tyr Ala Asp Glu Glu Asp Ser Phe Val Ser Asp Ser
                885                 890                 895

Ser Asp Gln Val Gln Ala Cys Gly Arg Ala Cys Phe Tyr Gln Ser Arg
            900                 905                 910

Gly Phe Pro Leu Val Arg Tyr Ala Tyr Asn Leu Pro Arg Val Lys Asp
        915                 920                 925
```

<210> SEQ ID NO 16
<211> LENGTH: 1572
<212> TYPE: DNA
<213> ORGANISM: Artificial Sequence
<220> FEATURE:

<223> OTHER INFORMATION: Nucleotide sequence encoding mRSPO1-Fc

<400> SEQUENCE: 16

```
atggagacag acacactcct gctatgggta ctgctgctct gggttccagg ttccactggt     60
gactatccat atgatgttcc agattatgct ggggcccagc cggcctggac acacatcgcc    120
gtgggcagcc gggggatcaa gggcaagaga cagaggcgga tcagtgctga ggggagccaa    180
gcctgcgcca agggctgtga gctctgttca gaagtcaacg gttgcctcaa gtgctcgccc    240
aagctcttca ttctgctgga gaggaacgac atccgccagg tgggcgtctg cctgccgtcc    300
tgcccacctg gatactttga tgcccgcaac cccgacatga acaaatgcat caaatgcaag    360
atcgagcact gtgaggcctg cttcagccac aacttctgca ccaagtgtca ggagggcttg    420
tacttacaca agggccgctg ctatccagcc tgccctgagg gctctacagc cgctaacagc    480
accatggagt gcggcagtcc tgcacaatgt gaaatgagcg agtggtcccc gtggggaccc    540
tgctccaaga agaggaagct gtgcggtttc cggaagggat cggaagagcg gacacgcaga    600
gtgctccatg ctcccggggg agaccacacc acctgctccg acaccaaaga gacccgcaag    660
tgtaccgtgc gcaggacgcc ctgcccagag gggcagaaga ggaggaaggg gggccagggc    720
cggagggaga atgccaacag gcatccggcc aggaagaaca gcaaggagcc gggctccaac    780
tctcggagac acaaagggca acagcagcca cagccaggga caacagggcc actcacatca    840
gtaggaccta cctgggcaca gcgtcgacta gagcccagag ggcccacaat caagccctgt    900
cctccatgca aatgcccagc acctaacctc ttgggtggac catccgtctt catcttccct    960
ccaaagatca aggatgtact catgatctcc ctgagcccca tagtcacatg tgtggtggtg   1020
gatgtgagcg aggatgaccc agatgtccag atcagctggt ttgtgaacaa cgtggaagta   1080
cacacagctc agacacaaac ccatagagag gattacaaca gtactctccg ggtggtcagt   1140
gccctcccca tccagcacca ggactggatg agtggcaagg agttcaaatg caaggtcaac   1200
aacaaagacc tcccagcgcc catcgagaga accatctcaa aacccaaagg gtcagtaaga   1260
gctccacagg tatatgtctt gcctccacca gaagaagaga tgactaagaa acaggtcact   1320
ctgacctgca tggtcacaga cttcatgcct gaagacattt acgtggagtg gaccaacaac   1380
gggaaaacag agctaaacta caagaacact gaaccagtcc tggactctga tggttcttac   1440
ttcatgtaca gcaagctgag agtggaaaag aagaactggg tggaaagaaa tagctactcc   1500
tgttcagtgg tccacgaggg tctgcacaat caccacacga ctaagagctt ctcccggact   1560
ccgggtaaat ga                                                       1572
```

<210> SEQ ID NO 17
<211> LENGTH: 523
<212> TYPE: PRT
<213> ORGANISM: Artificial Sequence
<220> FEATURE:
<223> OTHER INFORMATION: Polypeptide sequence of mRSPO1-Fc encoded by the above nucleotide sequence

<400> SEQUENCE: 17

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Trp Thr His Ile Ala Val Gly Ser Arg Gly Ile Lys Gly
        35                  40                  45

Lys Arg Gln Arg Arg Ile Ser Ala Glu Gly Ser Gln Ala Cys Ala Lys
```

```
    50                  55                  60

Gly Cys Glu Leu Cys Ser Glu Val Asn Gly Cys Leu Lys Cys Ser Pro
65                  70                  75                  80

Lys Leu Phe Ile Leu Leu Glu Arg Asn Asp Ile Arg Gln Val Gly Val
                85                  90                  95

Cys Leu Pro Ser Cys Pro Pro Gly Tyr Phe Asp Ala Arg Asn Pro Asp
            100                 105                 110

Met Asn Lys Cys Ile Lys Cys Lys Ile Glu His Cys Glu Ala Cys Phe
        115                 120                 125

Ser His Asn Phe Cys Thr Lys Cys Gln Glu Gly Leu Tyr Leu His Lys
    130                 135                 140

Gly Arg Cys Tyr Pro Ala Cys Pro Glu Gly Ser Thr Ala Ala Asn Ser
145                 150                 155                 160

Thr Met Glu Cys Gly Ser Pro Ala Gln Cys Glu Met Ser Glu Trp Ser
                165                 170                 175

Pro Trp Gly Pro Cys Ser Lys Lys Arg Lys Leu Cys Gly Phe Arg Lys
            180                 185                 190

Gly Ser Glu Glu Arg Thr Arg Arg Val Leu His Ala Pro Gly Gly Asp
        195                 200                 205

His Thr Thr Cys Ser Asp Thr Lys Glu Thr Arg Lys Cys Thr Val Arg
    210                 215                 220

Arg Thr Pro Cys Pro Glu Gly Gln Lys Arg Arg Lys Gly Gly Gln Gly
225                 230                 235                 240

Arg Arg Glu Asn Ala Asn Arg His Pro Ala Arg Lys Asn Ser Lys Glu
                245                 250                 255

Pro Gly Ser Asn Ser Arg Arg His Lys Gly Gln Gln Gln Pro Gln Pro
            260                 265                 270

Gly Thr Thr Gly Pro Leu Thr Ser Val Gly Pro Thr Trp Ala Gln Arg
        275                 280                 285

Arg Leu Glu Pro Arg Gly Pro Thr Ile Lys Pro Cys Pro Pro Cys Lys
    290                 295                 300

Cys Pro Ala Pro Asn Leu Leu Gly Gly Pro Ser Val Phe Ile Phe Pro
305                 310                 315                 320

Pro Lys Ile Lys Asp Val Leu Met Ile Ser Leu Ser Pro Ile Val Thr
                325                 330                 335

Cys Val Val Val Asp Val Ser Glu Asp Asp Pro Asp Val Gln Ile Ser
            340                 345                 350

Trp Phe Val Asn Asn Val Glu Val His Thr Ala Gln Thr Gln Thr His
        355                 360                 365

Arg Glu Asp Tyr Asn Ser Thr Leu Arg Val Val Ser Ala Leu Pro Ile
    370                 375                 380

Gln His Gln Asp Trp Met Ser Gly Lys Glu Phe Lys Cys Lys Val Asn
385                 390                 395                 400

Asn Lys Asp Leu Pro Ala Pro Ile Glu Arg Thr Ile Ser Lys Pro Lys
                405                 410                 415

Gly Ser Val Arg Ala Pro Gln Val Tyr Val Leu Pro Pro Pro Glu Glu
            420                 425                 430

Glu Met Thr Lys Lys Gln Val Thr Leu Thr Cys Met Val Thr Asp Phe
        435                 440                 445

Met Pro Glu Asp Ile Tyr Val Glu Trp Thr Asn Asn Gly Lys Thr Glu
    450                 455                 460

Leu Asn Tyr Lys Asn Thr Glu Pro Val Leu Asp Ser Asp Gly Ser Tyr
465                 470                 475                 480
```

```
Phe Met Tyr Ser Lys Leu Arg Val Glu Lys Lys Asn Trp Val Glu Arg
                485                 490                 495

Asn Ser Tyr Ser Cys Ser Val Val His Glu Gly Leu His Asn His His
            500                 505                 510

Thr Thr Lys Ser Phe Ser Arg Thr Pro Gly Lys
        515                 520
```

<210> SEQ ID NO 18
<211> LENGTH: 1629
<212> TYPE: DNA
<213> ORGANISM: Artificial Sequence
<220> FEATURE:
<223> OTHER INFORMATION: Nucleotide sequence encoding the extracellular domain of human LGR5

<400> SEQUENCE: 18

```
ggcagctctc ccaggtctgg tgtgttgctg aggggctgcc ccacacactg tcattgcgag     60

cccgacggca ggatgttgct cagggtggac tgctccgacc tggggctctc ggagctgcct    120

tccaacctca gcgtcttcac ctcctaccta gacctcagta tgaacaacat cagtcagctg    180

ctcccgaatc ccctgcccag tctccgcttc ctggaggagt tacgtcttgc gggaaacgct    240

ctgacataca ttcccaaggg agcattcact ggcctttaca gtcttaaagt tcttatgctg    300

cagaataatc agctaagaca cgtacccaca gaagctctgc agaatttgcg aagccttcaa    360

tccctgcgtc tggatgctaa ccacatcagc tatgtgcccc caagctgttt cagtggcctg    420

cattccctga ggcacctgtg gctggatgac aatgcgttaa cagaaatccc cgtccaggct    480

tttagaagtt tatcggcatt gcaagccatg accttggccc tgaacaaaat acaccacata    540

ccagactatg cctttggaaa cctctccagc ttggtagttc tacatctcca taacaataga    600

atccactccc tgggaaagaa atgctttgat gggctccaca gcctagagac tttagattta    660

aattacaata accttgatga attccccact gcaattagga cactctccaa ccttaaagaa    720

ctaggatttc atagcaacaa tatcaggtcg atacctgaga aagcatttgt aggcaaccct    780

tctcttatta caatacattt ctatgacaat cccatccaat ttgttgggag atctgctttt    840

caacatttac ctgaactaag aacactgact ctgaatggtg cctcacaaat aactgaattt    900

cctgatttaa ctggaactgc aaacctggag agtctgactt taactggagc acagatctca    960

tctcttcctc aaaccgtctg caatcagtta cctaatctcc aagtgctaga tctgtcttac   1020

aacctattag aagatttacc cagtttttca gtctgccaaa agcttcagaa aattgaccta   1080

agacataatg aaatctacga aattaaagtt gacactttcc agcagttgct tagcctccga   1140

tcgctgaatt tggcttggaa caaaattgct attattcacc ccaatgcatt ttccactttg   1200

ccatccctaa taaagctgga cctatcgtcc aacctcctgt cgtcttttcc tataactggg   1260

ttacatggtt taactcactt aaaattaaca ggaaatcatg ccttacagag cttgatatca   1320

tctgaaaact ttccagaact caaggttata gaaatgcctt atgcttacca gtgctgtgca   1380

tttggagtgt gtgagaatgc ctataagatt tctaatcaat ggaataaagg tgacaacagc   1440

agtatggacg accttcataa gaaagatgct ggaatgtttc aggctcaaga tgaacgtgac   1500

cttgaagatt tcctgcttga ctttgaggaa gacctgaaag cccttcattc agtgcagtgt   1560

tcaccttccc caggcccctt caaaccctgt gaacacctgc ttgatggctg gctgatcaga   1620

attggatag                                                           1629
```

<210> SEQ ID NO 19

```
<211> LENGTH: 542
<212> TYPE: PRT
<213> ORGANISM: Artificial Sequence
<220> FEATURE:
<223> OTHER INFORMATION: Polypeptide sequence of the extracellular
      domain of human LGR5 encoded by the above sequence

<400> SEQUENCE: 19

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Leu Pro Asn Pro
    50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
            100                 105                 110

Leu Gln Asn Leu Arg Ser Leu Gln Ser Leu Arg Leu Asp Ala Asn His
        115                 120                 125

Ile Ser Tyr Val Pro Pro Ser Cys Phe Ser Gly Leu His Ser Leu Arg
    130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
            180                 185                 190

Val Leu His Leu His Asn Asn Arg Ile His Ser Leu Gly Lys Lys Cys
        195                 200                 205

Phe Asp Gly Leu His Ser Leu Glu Thr Leu Asp Leu Asn Tyr Asn Asn
    210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
                245                 250                 255

Val Gly Asn Pro Ser Leu Ile Thr Ile His Phe Tyr Asp Asn Pro Ile
            260                 265                 270

Gln Phe Val Gly Arg Ser Ala Phe Gln His Leu Pro Glu Leu Arg Thr
        275                 280                 285

Leu Thr Leu Asn Gly Ala Ser Gln Ile Thr Glu Phe Pro Asp Leu Thr
    290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
        355                 360                 365

Lys Val Asp Thr Phe Gln Gln Leu Leu Ser Leu Arg Ser Leu Asn Leu
```

```
    370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Ile Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
        435                 440                 445

Val Ile Glu Met Pro Tyr Ala Tyr Gln Cys Cys Ala Phe Gly Val Cys
    450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
        515                 520                 525

Pro Cys Glu His Leu Leu Asp Gly Trp Leu Ile Arg Ile Gly
    530                 535                 540


<210> SEQ ID NO 20
<211> LENGTH: 19
<212> TYPE: DNA
<213> ORGANISM: Artificial Sequenc
<220> FEATURE:
<223> OTHER INFORMATION: 2559(+) primer

<400> SEQUENCE: 20

ctttgtttgc catttccta                                                    19


<210> SEQ ID NO 21
<211> LENGTH: 22
<212> TYPE: DNA
<213> ORGANISM: Artificial Sequence
<220> FEATURE:
<223> OTHER INFORMATION: 2634(-) primer

<400> SEQUENCE: 21

ctagtgagtt taatagcact aa                                                22


<210> SEQ ID NO 22
<211> LENGTH: 26
<212> TYPE: DNA
<213> ORGANISM: Artificial Sequence
<220> FEATURE:
<223> OTHER INFORMATION: 2586(+) probe

<400> SEQUENCE: 22

acgccatcat taggattcac tgtaac                                            26


<210> SEQ ID NO 23
<211> LENGTH: 19
<212> TYPE: DNA
<213> ORGANISM: Artificial Sequence
<220> FEATURE:
<223> OTHER INFORMATION: 1066(+) primer

<400> SEQUENCE: 23

atctcatctc ttcctcaaa                                                    19
```

<210> SEQ ID NO 24
<211> LENGTH: 21
<212> TYPE: DNA
<213> ORGANISM: Artificial Sequence
<220> FEATURE:
<223> OTHER INFORMATION: 1144(-) primer

<400> SEQUENCE: 24
cttctaatag gttgtaagac a 21

<210> SEQ ID NO 25
<211> LENGTH: 27
<212> TYPE: DNA
<213> ORGANISM: Artificial Sequence
<220> FEATURE:
<223> OTHER INFORMATION: 1092(+) probe

<400> SEQUENCE: 25
caatcagtta cctaatctcc aagtgct 27

<210> SEQ ID NO 26
<211> LENGTH: 17
<212> TYPE: DNA
<213> ORGANISM: Artificial Sequence
<220> FEATURE:
<223> OTHER INFORMATION: 2933(+) primer

<400> SEQUENCE: 26
ctcttccctt tcctctc 17

<210> SEQ ID NO 27
<211> LENGTH: 20
<212> TYPE: DNA
<213> ORGANISM: Artificial Sequence
<220> FEATURE:
<223> OTHER INFORMATION: 3001(-) primer

<400> SEQUENCE: 27
ctgagttttg gttgtatttg 20

<210> SEQ ID NO 28
<211> LENGTH: 20
<212> TYPE: DNA
<213> ORGANISM: Artificial Sequence
<220> FEATURE:
<223> OTHER INFORMATION: 2975(-) probe

<400> SEQUENCE: 28
aagcagccat cattcaccga 20

<210> SEQ ID NO 29
<211> LENGTH: 19
<212> TYPE: DNA
<213> ORGANISM: Artificial Sequence
<220> FEATURE:
<223> OTHER INFORMATION: 487(+) primer

<400> SEQUENCE: 29
tactcagtat taaggttgg 19

<210> SEQ ID NO 30
<211> LENGTH: 19
<212> TYPE: DNA
<213> ORGANISM: Artificial Sequence
<220> FEATURE:

<223> OTHER INFORMATION: 562(-) primer

<400> SEQUENCE: 30
cctcggaata tcatatgag 19

<210> SEQ ID NO 31
<211> LENGTH: 19
<212> TYPE: DNA
<213> ORGANISM: Artificial Sequence
<220> FEATURE:
<223> OTHER INFORMATION: 515(+) probe

<400> SEQUENCE: 31
tagtccctgc tgacgtgac 19

<210> SEQ ID NO 32
<211> LENGTH: 17
<212> TYPE: DNA
<213> ORGANISM: Artificial Sequence
<220> FEATURE:
<223> OTHER INFORMATION: 1076(+) primer

<400> SEQUENCE: 32
gaatgtgtgg aaggatg 17

<210> SEQ ID NO 33
<211> LENGTH: 18
<212> TYPE: DNA
<213> ORGANISM: Artificial Sequence
<220> FEATURE:
<223> OTHER INFORMATION: 1143(-) primer

<400> SEQUENCE: 33
gtgcgattat ttctgcta 18

<210> SEQ ID NO 34
<211> LENGTH: 20
<212> TYPE: DNA
<213> ORGANISM: Artificial Sequence
<220> FEATURE:
<223> OTHER INFORMATION: 1115(+) probe

<400> SEQUENCE: 34
attcgctcca atgaccaact 20

<210> SEQ ID NO 35
<211> LENGTH: 17
<212> TYPE: DNA
<213> ORGANISM: Artificial Sequence
<220> FEATURE:
<223> OTHER INFORMATION: 1007(+) primer

<400> SEQUENCE: 35
atccagcaaa gaaatcc 17

<210> SEQ ID NO 36
<211> LENGTH: 20
<212> TYPE: DNA
<213> ORGANISM: Artificial Sequence
<220> FEATURE:
<223> OTHER INFORMATION: 1090(-) primer

<400> SEQUENCE: 36
gataccgatt tctgtttatc 20

<210> SEQ ID NO 37
<211> LENGTH: 19
<212> TYPE: DNA
<213> ORGANISM: Artificial Sequence
<220> FEATURE:
<223> OTHER INFORMATION: 1061(-) probe

<400> SEQUENCE: 37
tcgcttcttc tgctgctgt 19

<210> SEQ ID NO 38
<211> LENGTH: 18
<212> TYPE: DNA
<213> ORGANISM: Artificial Sequence
<220> FEATURE:
<223> OTHER INFORMATION: 895(+) primer

<400> SEQUENCE: 38
ctctgtcttc tccatttg 18

<210> SEQ ID NO 39
<211> LENGTH: 17
<212> TYPE: DNA
<213> ORGANISM: Artificial Sequence
<220> FEATURE:
<223> OTHER INFORMATION: 966(-) primer

<400> SEQUENCE: 39
aaagggaagg tagactg 17

<210> SEQ ID NO 40
<211> LENGTH: 26
<212> TYPE: DNA
<213> ORGANISM: Artificial Sequence
<220> FEATURE:
<223> OTHER INFORMATION: 915(+) probe

<400> SEQUENCE: 40
ctctctttct ttccaccctt ctatca 26

<210> SEQ ID NO 41
<211> LENGTH: 4170
<212> TYPE: DNA
<213> ORGANISM: Artificial Sequence
<220> FEATURE:
<223> OTHER INFORMATION: LRP6 nucleotide

<400> SEQUENCE: 41
gcccctttgt tgctttatgc aaacagacgg gacttgcgat tggttgatgc tacaaatggc 60
aaagagaatg ctacgattgt agttggaggc ttggaggatg cagctgcggt ggactttgtg 120
tttagtcatg gcttgatata ctggagtgat gtcagcgaag aagccattaa acgaacagaa 180
tttaacaaaa ctgagagtgt gcagaatgtt gttgtttctg gattattgtc ccccgatggg 240
ctggcatgtg attggcttgg agaaaaattg tactggacag attctgaaac taatcggatt 300
gaagtttcta atttagatgg atctttacga aaagttttat tttggcaaga gttggatcaa 360
cccagagcta ttgccttaga tccttcaagt gggttcatgt actggacaga ctggggagaa 420
gtgccaaaga tagaacgtgc tggaatggat ggttcaagtc gcttcattat aataaacagt 480
gaaatttact ggccaaatgg actgactttg gattatgaag aacaaaagct ttattgggca 540
gatgcaaaac ttaatttcat ccacaaatca aatctggatg gaacaaatcg gcaggcagtg 600
gttaaaggtt cccttccaca tccttttgcc ttgacgttat ttgaggacat attgtactgg 660

-continued

```
actgactgga gcacacactc cattttggct tgcaacaagt atactggtga gggtctgcgt    720
gaaatccatt ctgacatctt ctctcccatg gatatacatg ccttcagcca acagaggcag    780
ccaaatgcca caaatccatg tggaattgac aatgggggtt gttcccattt gtgtttgatg    840
tctccagtca agccttttta tcagtgtgct tgccccactg ggtcaaact  cctggagaat    900
ggaaaaacct gcaaagatgg tgccacagaa ttattgcttt tagctcgaag gacagacttg    960
agacgcattt ctttggatac accagatttt acagacattg ttctgcagtt agaagacatc   1020
cgtcatgcca ttgccataga ttacgatcct gtggaaggct acatctactg gactgatgat   1080
gaagtgaggg ccatacgccg ttcatttata gatggatctg gcagtcagtt tgtggtcact   1140
gctcaaattg cccatcctga tggtattgct gtggactggg ttgcacgaaa tctttattgg   1200
acagacactg gcactgatcg aatagaagtg acaaggctca atgggaccat gaggaagatc   1260
ttgatttcag aggacttaga ggaaccccgg gctattgtgt tagatcccat ggttgggtac   1320
atgtattgga ctgactgggg agaaattccg aaaattgagc gagcagctct ggatggttct   1380
gaccgtgtag tattggttaa cacttctctt ggttggccaa atggtttagc cttggattat   1440
gatgaaggca aaatatactg gggagatgcc aaaacagaca agattgaggt tatgaatact   1500
gatggcactg ggagacgagt actagtggaa gacaaaattc ctcacatatt tggatttact   1560
ttgttgggtg actatgttta ctggactgac tggcagaggc gtagcattga aagagttcat   1620
aaacgaagtg cagagaggga agtgatcata gatcagctgc ctgacctcat gggcctaaag   1680
gctacaaatg ttcatcgagt gattggttcc aacccctgtg ctgaggaaaa cgggggatgt   1740
agccatctct gcctctatag acctcagggc cttcgctgtg cttgccctat tggctttgaa   1800
ctcatcagtg acatgaagac ctgcattgtc ccagaggctt tccttttgtt ttcacggaga   1860
gcagatatca gacgaatttc tctggaaaca aacaataata atgtggctat tccactcact   1920
ggtgtcaaag aagcttctgc tttggatttt gatgtgacag acaaccgaat ttattggact   1980
gatatatcac tcaagaccat cagcagagcc tttatgaatg gcagtgcact ggaacatgtg   2040
gtagaattcg gcttagatta tccagaaggc atggcagtag actggcttgg gaagaacttg   2100
tactgggcag acacaggaac gaatcgaatt gaggtgtcaa agttggatgg gcagcaccga   2160
caagttttgg tgtggaaaga cctagatagt cccagagctc tcgcgttgga ccctgccgaa   2220
ggatttatgt attggactga atggggtgga aaacctaaga tagacagagc tgcaatggat   2280
ggaagtgaac gtactacctt agttccaaat gtggggcggg caaacggcct aactattgat   2340
tatgctaaaa ggaggcttta ttggacagac ctggacacca acttaataga atcttcaaat   2400
atgcttgggc tcaaccgtga agttatagca gatgacttgc ctcatccttt tggcttaact   2460
cagtaccaag attatatcta ctggacggac tggagccgac gcagcattga gcgtgccaac   2520
aaaaccagtg gccaaaaccg caccatcatt cagggccatt tggattatgt gatggacatc   2580
ctcgtctttc actcatctcg acagtcaggg tggaatgaat gtgcttccag caatgggcac   2640
tgctcccacc tctgcttggc tgtgccagtt gggggttttg tttgtggatg ccctgcccac   2700
tactctctta atgctgacaa caggacttgt agtgctccta cgactttcct gctcttcagt   2760
caaaagagtg ccatcaaccg catggtgatt gatgaacaac agagccccga catcatcctt   2820
cccatccaca gccttcggaa tgtccgggcc attgactatg acccactgga caagcaactc   2880
tattggattg actcacgaca aaacatgatc cgaaaggcac aagaagatgg cagccagggc   2940
tttactgtgg ttgtgagctc agttccgagt cagaacctgg aaatacaacc ctatgacctc   3000
agcattgata tttacagccg ctacatctac tggacttgtg aggctaccaa tgtcattaat   3060
```

```
gtgacaagat tagatgggag atcagttgga gtggtgctga aaggcgagca ggacagacct   3120

cgagccgttg tggtaaaccc agagaaaggg tatatgtatt ttaccaatct tcaggaaagg   3180

tctcctaaaa ttgaacgggc tgctttggat gggacagaac gggaggtcct ctttttcagt   3240

ggcttaagta aaccaattgc tttagccctt gatagcaggc tgggcaagct cttttgggct   3300

gattcagatc tccggcgaat tgaaagcagt gatctctcag gtgctaaccg gatagtatta   3360

gaagactcca atatcttgca gcctgtggga cttactgtgt ttgaaaactg gctctattgg   3420

attgataaac agcagcaaat gattgaaaaa attgacatga caggtcgaga gggtagaacc   3480

aaagtccaag ctcgaattgc ccagcttagt gacattcatg cagtaaagga gctgaacctt   3540

caagaataca gacagcaccc ttgtgctcag gataatggtg gctgttcaca tatttgtctt   3600

gtaaaggggg atggtactac aaggtgttct tgccccatgc acctggttct acttcaagat   3660

gagctatcat gtggagaacc tccaacatgt tctcctcagc agtttacttg tttcacgggg   3720

gaaattgact gtatccctgt ggcttggcgg tgcgatgggt ttactgaatg tgaagaccac   3780

agtgatgaac tcaattgtcc tgtatgctca gagtcccagt tccagtgtgc cagtgggcag   3840

tgtattgatg gtgccctccg atgcaatgga gatgcaaact gccaggacaa atcagatgag   3900

aagaactgtg aagtgctttg tttaattgat cagttccgct gtgccaatgg tcagtgcatt   3960

ggaaagcaca agaagtgtga tcataatgtg gattgcagtg acaagtcaga tgaactggat   4020

tgttatccga ctgaagaacc agcaccacag gccaccaata cagttggttc tgttattggc   4080

gtaattgtca ccatttttgt gtctggaact gtatacttta tctgccagag gatgttgtgt   4140

ccacgtatga agggagatgg ggaaacttga                                    4170
```

<210> SEQ ID NO 42
<211> LENGTH: 1389
<212> TYPE: PRT
<213> ORGANISM: Artificial Sequence
<220> FEATURE:
<223> OTHER INFORMATION: LRP6 amino acid

<400> SEQUENCE: 42

```
Ala Pro Leu Leu Leu Tyr Ala Asn Arg Arg Asp Leu Arg Leu Val Asp
1               5                   10                  15

Ala Thr Asn Gly Lys Glu Asn Ala Thr Ile Val Val Gly Gly Leu Glu
            20                  25                  30

Asp Ala Ala Ala Val Asp Phe Val Phe Ser His Gly Leu Ile Tyr Trp
        35                  40                  45

Ser Asp Val Ser Glu Glu Ala Ile Lys Arg Thr Glu Phe Asn Lys Thr
    50                  55                  60

Glu Ser Val Gln Asn Val Val Val Ser Gly Leu Leu Ser Pro Asp Gly
65                  70                  75                  80

Leu Ala Cys Asp Trp Leu Gly Glu Lys Leu Tyr Trp Thr Asp Ser Glu
                85                  90                  95

Thr Asn Arg Ile Glu Val Ser Asn Leu Asp Gly Ser Leu Arg Lys Val
            100                 105                 110

Leu Phe Trp Gln Glu Leu Asp Gln Pro Arg Ala Ile Ala Leu Asp Pro
        115                 120                 125

Ser Ser Gly Phe Met Tyr Trp Thr Asp Trp Gly Glu Val Pro Lys Ile
    130                 135                 140

Glu Arg Ala Gly Met Asp Gly Ser Ser Arg Phe Ile Ile Ile Asn Ser
145                 150                 155                 160
```

```
Glu Ile Tyr Trp Pro Asn Gly Leu Thr Leu Asp Tyr Glu Glu Gln Lys
                165                 170                 175

Leu Tyr Trp Ala Asp Ala Lys Leu Asn Phe Ile His Lys Ser Asn Leu
            180                 185                 190

Asp Gly Thr Asn Arg Gln Ala Val Val Lys Gly Ser Leu Pro His Pro
        195                 200                 205

Phe Ala Leu Thr Leu Phe Glu Asp Ile Leu Tyr Trp Thr Asp Trp Ser
    210                 215                 220

Thr His Ser Ile Leu Ala Cys Asn Lys Tyr Thr Gly Glu Gly Leu Arg
225                 230                 235                 240

Glu Ile His Ser Asp Ile Phe Ser Pro Met Asp Ile His Ala Phe Ser
                245                 250                 255

Gln Gln Arg Gln Pro Asn Ala Thr Asn Pro Cys Gly Ile Asp Asn Gly
            260                 265                 270

Gly Cys Ser His Leu Cys Leu Met Ser Pro Val Lys Pro Phe Tyr Gln
        275                 280                 285

Cys Ala Cys Pro Thr Gly Val Lys Leu Leu Glu Asn Gly Lys Thr Cys
    290                 295                 300

Lys Asp Gly Ala Thr Glu Leu Leu Leu Leu Ala Arg Arg Thr Asp Leu
305                 310                 315                 320

Arg Arg Ile Ser Leu Asp Thr Pro Asp Phe Thr Asp Ile Val Leu Gln
                325                 330                 335

Leu Glu Asp Ile Arg His Ala Ile Ala Ile Asp Tyr Asp Pro Val Glu
            340                 345                 350

Gly Tyr Ile Tyr Trp Thr Asp Asp Glu Val Arg Ala Ile Arg Arg Ser
        355                 360                 365

Phe Ile Asp Gly Ser Gly Ser Gln Phe Val Val Thr Ala Gln Ile Ala
    370                 375                 380

His Pro Asp Gly Ile Ala Val Asp Trp Val Ala Arg Asn Leu Tyr Trp
385                 390                 395                 400

Thr Asp Thr Gly Thr Asp Arg Ile Glu Val Thr Arg Leu Asn Gly Thr
                405                 410                 415

Met Arg Lys Ile Leu Ile Ser Glu Asp Leu Glu Glu Pro Arg Ala Ile
            420                 425                 430

Val Leu Asp Pro Met Val Gly Tyr Met Tyr Trp Thr Asp Trp Gly Glu
        435                 440                 445

Ile Pro Lys Ile Glu Arg Ala Ala Leu Asp Gly Ser Asp Arg Val Val
    450                 455                 460

Leu Val Asn Thr Ser Leu Gly Trp Pro Asn Gly Leu Ala Leu Asp Tyr
465                 470                 475                 480

Asp Glu Gly Lys Ile Tyr Trp Gly Asp Ala Lys Thr Asp Lys Ile Glu
                485                 490                 495

Val Met Asn Thr Asp Gly Thr Gly Arg Arg Val Leu Val Glu Asp Lys
            500                 505                 510

Ile Pro His Ile Phe Gly Phe Thr Leu Leu Gly Asp Tyr Val Tyr Trp
        515                 520                 525

Thr Asp Trp Gln Arg Arg Ser Ile Glu Arg Val His Lys Arg Ser Ala
    530                 535                 540

Glu Arg Glu Val Ile Ile Asp Gln Leu Pro Asp Leu Met Gly Leu Lys
545                 550                 555                 560

Ala Thr Asn Val His Arg Val Ile Gly Ser Asn Pro Cys Ala Glu Glu
                565                 570                 575

Asn Gly Gly Cys Ser His Leu Cys Leu Tyr Arg Pro Gln Gly Leu Arg
```

```
            580                 585                 590

Cys Ala Cys Pro Ile Gly Phe Glu Leu Ile Ser Asp Met Lys Thr Cys
        595                 600                 605

Ile Val Pro Glu Ala Phe Leu Leu Phe Ser Arg Arg Ala Asp Ile Arg
    610                 615                 620

Arg Ile Ser Leu Glu Thr Asn Asn Asn Asn Val Ala Ile Pro Leu Thr
625                 630                 635                 640

Gly Val Lys Glu Ala Ser Ala Leu Asp Phe Asp Val Thr Asp Asn Arg
                645                 650                 655

Ile Tyr Trp Thr Asp Ile Ser Leu Lys Thr Ile Ser Arg Ala Phe Met
            660                 665                 670

Asn Gly Ser Ala Leu Glu His Val Val Glu Phe Gly Leu Asp Tyr Pro
        675                 680                 685

Glu Gly Met Ala Val Asp Trp Leu Gly Lys Asn Leu Tyr Trp Ala Asp
    690                 695                 700

Thr Gly Thr Asn Arg Ile Glu Val Ser Lys Leu Asp Gly Gln His Arg
705                 710                 715                 720

Gln Val Leu Val Trp Lys Asp Leu Asp Ser Pro Arg Ala Leu Ala Leu
                725                 730                 735

Asp Pro Ala Glu Gly Phe Met Tyr Trp Thr Glu Trp Gly Gly Lys Pro
            740                 745                 750

Lys Ile Asp Arg Ala Ala Met Asp Gly Ser Glu Arg Thr Thr Leu Val
        755                 760                 765

Pro Asn Val Gly Arg Ala Asn Gly Leu Thr Ile Asp Tyr Ala Lys Arg
    770                 775                 780

Arg Leu Tyr Trp Thr Asp Leu Asp Thr Asn Leu Ile Glu Ser Ser Asn
785                 790                 795                 800

Met Leu Gly Leu Asn Arg Glu Val Ile Ala Asp Asp Leu Pro His Pro
                805                 810                 815

Phe Gly Leu Thr Gln Tyr Gln Asp Tyr Ile Tyr Trp Thr Asp Trp Ser
            820                 825                 830

Arg Arg Ser Ile Glu Arg Ala Asn Lys Thr Ser Gly Gln Asn Arg Thr
        835                 840                 845

Ile Ile Gln Gly His Leu Asp Tyr Val Met Asp Ile Leu Val Phe His
    850                 855                 860

Ser Ser Arg Gln Ser Gly Trp Asn Glu Cys Ala Ser Ser Asn Gly His
865                 870                 875                 880

Cys Ser His Leu Cys Leu Ala Val Pro Val Gly Gly Phe Val Cys Gly
                885                 890                 895

Cys Pro Ala His Tyr Ser Leu Asn Ala Asp Asn Arg Thr Cys Ser Ala
            900                 905                 910

Pro Thr Thr Phe Leu Leu Phe Ser Gln Lys Ser Ala Ile Asn Arg Met
        915                 920                 925

Val Ile Asp Glu Gln Gln Ser Pro Asp Ile Ile Leu Pro Ile His Ser
    930                 935                 940

Leu Arg Asn Val Arg Ala Ile Asp Tyr Asp Pro Leu Asp Lys Gln Leu
945                 950                 955                 960

Tyr Trp Ile Asp Ser Arg Gln Asn Met Ile Arg Lys Ala Gln Glu Asp
                965                 970                 975

Gly Ser Gln Gly Phe Thr Val Val Val Ser Ser Val Pro Ser Gln Asn
            980                 985                 990

Leu Glu Ile Gln Pro Tyr Asp Leu  Ser Ile Asp Ile Tyr  Ser Arg Tyr
        995                 1000                1005
```

```
Ile Tyr  Trp Thr Cys Glu Ala  Thr Asn Val Ile Asn  Val Thr Arg
    1010                 1015                 1020

Leu Asp  Gly Arg Ser Val Gly  Val Val Leu Lys Gly  Glu Gln Asp
    1025                 1030                 1035

Arg Pro  Arg Ala Val Val Val  Asn Pro Glu Lys Gly  Tyr Met Tyr
    1040                 1045                 1050

Phe Thr  Asn Leu Gln Glu Arg  Ser Pro Lys Ile Glu  Arg Ala Ala
    1055                 1060                 1065

Leu Asp  Gly Thr Glu Arg Glu  Val Leu Phe Phe Ser  Gly Leu Ser
    1070                 1075                 1080

Lys Pro  Ile Ala Leu Ala Leu  Asp Ser Arg Leu Gly  Lys Leu Phe
    1085                 1090                 1095

Trp Ala  Asp Ser Asp Leu Arg  Arg Ile Glu Ser Ser  Asp Leu Ser
    1100                 1105                 1110

Gly Ala  Asn Arg Ile Val Leu  Glu Asp Ser Asn Ile  Leu Gln Pro
    1115                 1120                 1125

Val Gly  Leu Thr Val Phe Glu  Asn Trp Leu Tyr Trp  Ile Asp Lys
    1130                 1135                 1140

Gln Gln  Gln Met Ile Glu Lys  Ile Asp Met Thr Gly  Arg Glu Gly
    1145                 1150                 1155

Arg Thr  Lys Val Gln Ala Arg  Ile Ala Gln Leu Ser  Asp Ile His
    1160                 1165                 1170

Ala Val  Lys Glu Leu Asn Leu  Gln Glu Tyr Arg Gln  His Pro Cys
    1175                 1180                 1185

Ala Gln  Asp Asn Gly Gly Cys  Ser His Ile Cys Leu  Val Lys Gly
    1190                 1195                 1200

Asp Gly  Thr Thr Arg Cys Ser  Cys Pro Met His Leu  Val Leu Leu
    1205                 1210                 1215

Gln Asp  Glu Leu Ser Cys Gly  Glu Pro Pro Thr Cys  Ser Pro Gln
    1220                 1225                 1230

Gln Phe  Thr Cys Phe Thr Gly  Glu Ile Asp Cys Ile  Pro Val Ala
    1235                 1240                 1245

Trp Arg  Cys Asp Gly Phe Thr  Glu Cys Glu Asp His  Ser Asp Glu
    1250                 1255                 1260

Leu Asn  Cys Pro Val Cys Ser  Glu Ser Gln Phe Gln  Cys Ala Ser
    1265                 1270                 1275

Gly Gln  Cys Ile Asp Gly Ala  Leu Arg Cys Asn Gly  Asp Ala Asn
    1280                 1285                 1290

Cys Gln  Asp Lys Ser Asp Glu  Lys Asn Cys Glu Val  Leu Cys Leu
    1295                 1300                 1305

Ile Asp  Gln Phe Arg Cys Ala  Asn Gly Gln Cys Ile  Gly Lys His
    1310                 1315                 1320

Lys Lys  Cys Asp His Asn Val  Asp Cys Ser Asp Lys  Ser Asp Glu
    1325                 1330                 1335

Leu Asp  Cys Tyr Pro Thr Glu  Glu Pro Ala Pro Gln  Ala Thr Asn
    1340                 1345                 1350

Thr Val  Gly Ser Val Ile Gly  Val Ile Val Thr Ile  Phe Val Ser
    1355                 1360                 1365

Gly Thr  Val Tyr Phe Ile Cys  Gln Arg Met Leu Cys  Pro Arg Met
    1370                 1375                 1380

Lys Gly  Asp Gly Glu Thr
    1385
```

<210> SEQ ID NO 43
<211> LENGTH: 263
<212> TYPE: PRT
<213> ORGANISM: Artificial Sequence
<220> FEATURE:
<223> OTHER INFORMATION: RSPO1 amino acid

<400> SEQUENCE: 43

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gln Gly Thr Val Gly Pro
                245                 250                 255

Leu Thr Ser Ala Gly Pro Ala
            260
```

<210> SEQ ID NO 44
<211> LENGTH: 243
<212> TYPE: PRT
<213> ORGANISM: Artificial Sequence
<220> FEATURE:
<223> OTHER INFORMATION: RSPO2 amino acid

<400> SEQUENCE: 44

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45
```

```
Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln
```

<210> SEQ ID NO 45
<211> LENGTH: 4997
<212> TYPE: DNA
<213> ORGANISM: Artificial Sequence
<220> FEATURE:
<223> OTHER INFORMATION: b-catenin reporter plasmid Super 8x TOPFlash (firefly luciferase)

<400> SEQUENCE: 45

```
ggtaccgagc tcttacgcga gatcaaaggg ggtaagatca aagggggtaa gatcaaaggg      60

ggtaagatca aaggcgcgag atcaaagggg gtaagatcaa agggggtaag atcaaagggg     120

gtaagatcaa aggggcgcgc ccgcgtgcta gcccgggctc gagatctaga ctctagaggg     180

tatataatgg aagctcgaat tccagcttgg cattccggta ctgttggtaa aaagcttggc     240

attccggtac tgttggtaaa gccaccatgg aagacgccaa aaacataaag aaaggcccgg     300

cgccattcta tccgctggaa gatggaaccg ctggagagca actgcataag gctatgaaga     360

gatacgccct ggttcctgga acaattgctt ttacagatgc acatatcgag gtggacatca     420

cttacgctga gtacttcgaa atgtccgttc ggttggcaga agctatgaaa cgatatgggc     480

tgaatacaaa tcacagaatc gtcgtatgca gtgaaaactc tcttcaattc tttatgccgg     540

tgttgggcgc gttatttatc ggagttgcag ttgcgcccgc gaacgacatt tataatgaac     600

gtgaattgct caacagtatg ggcatttcgc agcctaccgt ggtgttcgtt tccaaaaagg     660

ggttgcaaaa aattttgaac gtgcaaaaaa agctcccaat catccaaaaa attattatca     720

tggattctaa aacggattac cagggatttc agtcgatgta cacgttcgtc acatctcatc     780

tacctcccgg ttttaatgaa tacgattttg tgccagagtc cttcgatagg gacaagacaa     840

ttgcactgat catgaactcc tctggatcta ctggtctgcc taaaggtgtc gctctgcctc     900
```

```
atagaactgc ctgcgtgaga ttctcgcatg ccagagatcc tatttttggc aatcaaatca    960
ttccggatac tgcgatttta agtgttgttc cattccatca cggttttgga atgtttacta   1020
cactcggata tttgatatgt ggatttcgag tcgtcttaat gtatagattt gaagaagagc   1080
tgtttctgag gagccttcag gattacaaga ttcaaagtgc gctgctggtg ccaaccctat   1140
tctccttctt cgccaaaagc actctgattg acaaatacga tttatctaat ttacacgaaa   1200
ttgcttctgg tggcgctccc ctctctaagg aagtcgggga agcggttgcc aagaggttcc   1260
atctgccagg tatcaggcaa ggatatgggc tcactgagac tacatcagct attctgatta   1320
cacccgaggg ggatgataaa ccgggcgcgg tcggtaaagt tgttccattt tttgaagcga   1380
aggttgtgga tctggatacc gggaaaacgc tgggcgttaa tcaaagaggc gaactgtgtg   1440
tgagaggtcc tatgattatg tccggttatg taaacaatcc ggaagcgacc aacgccttga   1500
ttgacaagga tggatggcta cattctggag acatagctta ctgggacgaa gacgaacact   1560
tcttcatcgt tgaccgcctg aagtctctga ttaagtacaa aggctatcag gtggctcccg   1620
ctgaattgga atccatcttg ctccaacacc ccaacatctt cgacgcaggt gtcgcaggtc   1680
ttcccgacga tgacgccggt gaacttcccg ccgccgttgt tgttttggag cacggaaaga   1740
cgatgacgga aaaagagatc gtggattacg tcgccagtca agtaacaacc gcgaaaaagt   1800
tgcgcggagg agttgtgttt gtggacgaag taccgaaagg tcttaccgga aaactcgacg   1860
caagaaaaat cagagagatc ctcataaagg ccaagaaggg cggaaagatc gccgtgtaat   1920
tctagagtcg gggcggccgg ccgcttcgag cagacatgat aagatacatt gatgagtttg   1980
gacaaaccac aactagaatg cagtgaaaaa aatgctttat ttgtgaaatt tgtgatgcta   2040
ttgctttatt tgtaaccatt ataagctgca ataaacaagt taacaacaac aattgcattc   2100
attttatgtt tcaggttcag ggggaggtgt gggaggtttt ttaaagcaag taaaacctct   2160
acaaatgtgg taaaatcgat aaggatccgt cgaccgatgc ccttgagagc cttcaaccca   2220
gtcagctcct tccggtgggc gcggggcatg actatcgtcg ccgcacttat gactgtcttc   2280
tttatcatgc aactcgtagg acaggtgccg gcagcgctct tccgcttcct cgctcactga   2340
ctcgctgcgc tcggtcgttc ggctgcggcg agcggtatca gctcactcaa aggcggtaat   2400
acggttatcc acagaatcag gggataacgc aggaaagaac atgtgagcaa aaggccagca   2460
aaaggccagg aaccgtaaaa aggccgcgtt gctggcgttt ttccataggc tccgcccccc   2520
tgacgagcat cacaaaaatc gacgctcaag tcagaggtgg cgaaacccga caggactata   2580
aagataccag gcgtttcccc ctggaagctc cctcgtgcgc tctcctgttc cgaccctgcc   2640
gcttaccgga tacctgtccg cctttctccc ttcgggaagc gtggcgcttt ctcatagctc   2700
acgctgtagg tatctcagtt cggtgtaggt cgttcgctcc aagctgggct gtgtgcacga   2760
accccccgtt cagcccgacc gctgcgcctt atccggtaac tatcgtcttg agtccaaccc   2820
ggtaagacac gacttatcgc cactggcagc agccactggt aacaggatta gcagagcgag   2880
gtatgtaggc ggtgctacag agttcttgaa gtggtggcct aactacggct acactagaag   2940
gacagtattt ggtatctgcg ctctgctgaa gccagttacc ttcggaaaaa gagttggtag   3000
ctcttgatcc ggcaaacaaa ccaccgctgg tagcggtggt ttttttgttt gcaagcagca   3060
gattacgcgc agaaaaaaag gatctcaaga agatcctttg atcttttcta cggggtctga   3120
cgctcagtgg aacgaaaact cacgttaagg gattttggtc atgagattat caaaaaggat   3180
cttcacctag atccttttaa attaaaaatg aagttttaaa tcaatctaaa gtatatatga   3240
```

-continued

```
gtaaacttgg tctgacagtt accaatgctt aatcagtgag gcacctatct cagcgatctg   3300

tctatttcgt tcatccatag ttgcctgact ccccgtcgtg tagataacta cgatacggga   3360

gggcttacca tctggcccca gtgctgcaat gataccgcga gacccacgct caccggctcc   3420

agatttatca gcaataaacc agccagccgg aagggccgag cgcagaagtg gtcctgcaac   3480

tttatccgcc tccatccagt ctattaattg ttgccgggaa gctagagtaa gtagttcgcc   3540

agttaatagt ttgcgcaacg ttgttgccat tgctacaggc atcgtggtgt cacgctcgtc   3600

gtttggtatg gcttcattca gctccggttc ccaacgatca aggcgagtta catgatcccc   3660

catgttgtgc aaaaaagcgg ttagctcctt cggtcctccg atcgttgtca gaagtaagtt   3720

ggccgcagtg ttatcactca tggttatggc agcactgcat aattctctta ctgtcatgcc   3780

atccgtaaga tgcttttctg tgactggtga gtactcaacc aagtcattct gagaatagtg   3840

tatgcggcga ccgagttgct cttgcccggc gtcaatacgg gataataccg cgccacatag   3900

cagaacttta aaagtgctca tcattggaaa acgttcttcg gggcgaaaac tctcaaggat   3960

cttaccgctg ttgagatcca gttcgatgta acccactcgt gcacccaact gatcttcagc   4020

atcttttact ttcaccagcg tttctgggtg agcaaaaaca ggaaggcaaa atgccgcaaa   4080

aaagggaata agggcgacac ggaaatgttg aatactcata ctcttccttt ttcaatatta   4140

ttgaagcatt tatcagggtt attgtctcat gagcggatac atatttgaat gtatttagaa   4200

aaataaacaa ataggggttc cgcgcacatt tccccgaaaa gtgccacctg acgcgccctg   4260

tagcggcgca ttaagcgcgg cgggtgtggt ggttacgcgc agcgtgaccg ctacacttgc   4320

cagcgcccta gcgcccgctc ctttcgcttt cttcccttcc tttctcgcca cgttcgccgg   4380

ctttccccgt caagctctaa atcgggggct ccctttaggg ttccgattta gtgctttacg   4440

gcacctcgac cccaaaaaac ttgattaggg tgatggttca cgtagtgggc catcgccctg   4500

atagacggtt tttcgccctt tgacgttgga gtccacgttc tttaatagtg gactcttgtt   4560

ccaaactgga acaacactca accctatctc ggtctattct tttgatttat aagggatttt   4620

gccgatttcg gcctattggt taaaaaatga gctgatttaa caaaaattta acgcgaattt   4680

taacaaaata ttaacgttta caatttccca ttcgccattc aggctgcgca actgttggga   4740

agggcgatcg gtgcgggcct cttcgctatt acgccagccc aagctaccat gataagtaag   4800

taatattaag gtacgggagg tacttggagc ggccgcaata aaatatcttt attttcatta   4860

catctgtgtg ttggtttttt gtgtgaatcg atagtactaa catacgctct ccatcaaaac   4920

aaaacgaaac aaaacaaact agcaaaatag gctgtcccca gtgcaagtgc aggtgccaga   4980

acatttctct atcgata                                                  4997
```

<210> SEQ ID NO 46
<211> LENGTH: 819
<212> TYPE: DNA
<213> ORGANISM: Artificial Sequence
<220> FEATURE:
<223> OTHER INFORMATION: human RSPO3 nucleotide sequence

<400> SEQUENCE: 46

```
atgcacttgc gactgatttc ttggcttttt atcattttga actttatgga atacatcggc     60

agccaaaacg cctcccgggg aaggcgccag cgaagaatgc atcctaacgt tagtcaaggc    120

tgccaaggag gctgtgcaac atgctcagat tacaatggat gtttgtcatg taagcccaga    180

ctattttttg ctctggaaag aattggcatg aagcagattg gagtatgtct ctcttcatgt    240

ccaagtggat attatggaac tcgatatcca gatataaata agtgtacaaa atgcaaagct    300
```

```
gactgtgata cctgtttcaa caaaaatttc tgcacaaaat gtaaaagtgg attttactta    360

caccttggaa agtgccttga caattgccca gaagggttgg aagccaacaa ccatactatg    420

gagtgtgtca gtattgtgca ctgtgaggtc agtgaatgga atccttggag tccatgcacg    480

aagaagggaa aaacatgtgg cttcaaaaga gggactgaaa cacgggtccg agaaataata    540

cagcatcctt cagcaaaggg taacctgtgt cccccaacaa atgagacaag aaagtgtaca    600

gtgcaaagga agaagtgtca gaagggagaa cgaggaaaaa aaggaaggga gaggaaaaga    660

aaaaaaccta ataaaggaga aagtaaagaa gcaatacctg acagcaaaag tctggaatcc    720

agcaaagaaa tcccagagca acgagaaaac aaacagcagc agaagaagcg aaaagtccaa    780

gataaacaga aatcggtatc agtcagcact gtacactag                           819
```

```
<210> SEQ ID NO 47
<211> LENGTH: 271
<212> TYPE: PRT
<213> ORGANISM: Artificial Sequence
<220> FEATURE:
<223> OTHER INFORMATION: human RSPO3 polypeptide sequence

<400> SEQUENCE: 47

His Leu Arg Leu Ile Ser Trp Leu Phe Ile Ile Leu Asn Phe Met Glu
1               5                   10                  15

Tyr Ile Gly Ser Gln Asn Ala Ser Arg Gly Arg Arg Gln Arg Arg Met
            20                  25                  30

His Pro Asn Val Ser Gln Gly Cys Gln Gly Gly Cys Ala Thr Cys Ser
        35                  40                  45

Asp Tyr Asn Gly Cys Leu Ser Cys Lys Pro Arg Leu Phe Phe Ala Leu
    50                  55                  60

Glu Arg Ile Gly Met Lys Gln Ile Gly Val Cys Leu Ser Ser Cys Pro
65                  70                  75                  80

Ser Gly Tyr Tyr Gly Thr Arg Tyr Pro Asp Ile Asn Lys Cys Thr Lys
                85                  90                  95

Cys Lys Ala Asp Cys Asp Thr Cys Phe Asn Lys Asn Phe Cys Thr Lys
            100                 105                 110

Cys Lys Ser Gly Phe Tyr Leu His Leu Gly Lys Cys Leu Asp Asn Cys
        115                 120                 125

Pro Glu Gly Leu Glu Ala Asn Asn His Thr Met Glu Cys Val Ser Ile
    130                 135                 140

Val His Cys Glu Val Ser Glu Trp Asn Pro Trp Ser Pro Cys Thr Lys
145                 150                 155                 160

Lys Gly Lys Thr Cys Gly Phe Lys Arg Gly Thr Glu Thr Arg Val Arg
                165                 170                 175

Glu Ile Ile Gln His Pro Ser Ala Lys Gly Asn Leu Cys Pro Pro Thr
            180                 185                 190

Asn Glu Thr Arg Lys Cys Thr Val Gln Arg Lys Lys Cys Gln Lys Gly
        195                 200                 205

Glu Arg Gly Lys Lys Gly Arg Glu Arg Lys Arg Lys Lys Pro Asn Lys
    210                 215                 220

Gly Glu Ser Lys Glu Ala Ile Pro Asp Ser Lys Ser Leu Glu Ser Ser
225                 230                 235                 240

Lys Glu Ile Pro Glu Gln Arg Glu Asn Lys Gln Gln Gln Lys Lys Arg
                245                 250                 255

Lys Val Gln Asp Lys Gln Lys Ser Val Ser Val Ser Thr Val His
            260                 265                 270
```

<210> SEQ ID NO 48
<211> LENGTH: 705
<212> TYPE: DNA
<213> ORGANISM: Artificial Sequence
<220> FEATURE:
<223> OTHER INFORMATION: human RSPO4 nucleotide sequence

<400> SEQUENCE: 48

```
atgcgggcgc cactctgcct gctcctgctc gtcgcccacg ccgtggacat gctcgccctg     60
aaccgaagga agaagcaagt gggcactggc ctgggggggca actgcacagg ctgtatcatc   120
tgctcagagg agaacggctg ttccacctgc cagcagaggc tcttcctgtt catccgccgg   180
gaaggcatcc gccagtacgg caagtgcctg cacgactgtc cccctgggta cttcggcatc   240
cgcggccagg aggtcaacag gtgcaaaaaa tgtggggcca cttgtgagag ctgcttcagc   300
caggacttct gcatccggtg caagaggcag ttttacttgt acaaggggaa gtgtctgccc   360
acctgcccgc cgggcacttt ggcccaccag aacacacggg agtgccaggg ggagtgtgaa   420
ctgggtccct ggggcggctg gagcccctgc acacacaatg gaaagacctg cggctcggct   480
tggggcctgg agagccgggt acgagaggct ggccgggctg ggcatgagga ggcagccacc   540
tgccaggtgc tttctgagtc aaggaaatgt cccatccaga ggccctgccc aggagagagg   600
agccccggcc agaagaaggg caggaaggac cggcgcccac gcaaggacag gaagctggac   660
cgcaggctgg acgtgaggcc gcgccagccc ggcctgcagc cctga                    705
```

<210> SEQ ID NO 49
<211> LENGTH: 234
<212> TYPE: PRT
<213> ORGANISM: Artificial Sequence
<220> FEATURE:
<223> OTHER INFORMATION: human RSPO4 polypeptide sequence

<400> SEQUENCE: 49

```
Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
```

```
        180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230


<210> SEQ ID NO 50
<211> LENGTH: 1059
<212> TYPE: DNA
<213> ORGANISM: Artificial Sequence
<220> FEATURE:
<223> OTHER INFORMATION: human Wnt3a nucleotide sequence

<400> SEQUENCE: 50

atggccccac tcggatactt cttactcctc tgcagcctga agcaggctct gggcagctac     60

ccgatctggt ggtcgctggc tgttgggcca cagtattcct ccctgggctc gcagcccatc    120

ctgtgtgcca gcatcccggg cctggtcccc aagcagctcc gcttctgcag gaactacgtg    180

gagatcatgc ccagcgtggc cgagggcatc aagattggca tccaggagtg ccagcaccag    240

ttccgcggcc gccggtggaa ctgcaccacc gtccacgaca gcctggccat cttcgggccc    300

gtgctggaca aagctaccag ggagtcggcc tttgtccacg ccattgcctc agccggtgtg    360

gcctttgcag tgacacgctc atgtgcagaa ggcacggccg ccatctgtgg ctgcagcagc    420

cgccaccagg gctcaccagg caagggctgg aagtggggtg gctgtagcga ggacatcgag    480

tttggtggga tggtgtctcg ggagttcgcc gacgcccggg agaaccggcc agatgcccgc    540

tcagccatga accgccacaa caacgaggct gggcgccagg ccatcgccag ccacatgcac    600

ctcaagtgca agtgccacgg gctgtcgggc agctgcgagg tgaagacatg ctggtggtcg    660

caacccgact tccgcgccat cggtgacttc ctcaaggaca agtacgacag cgcctcggag    720

atggtggtgg agaagcaccg ggagtcccgc ggctgggtgg agaccctgcg gccgcgctac    780

acctacttca aggtgcccac ggagcgcgac ctggtctact acgaggcctc gcccaacttc    840

tgcgagccca accctgagac gggctccttc ggcacgcgcg accgcacctg caacgtcagc    900

tcgcacggca tcgacggctg cgacctgctg tgctgcggcc gcggccacaa cgcgcgagcg    960

gagcggcgcc gggagaagtg ccgctgcgtg ttccactggt gctgctacgt cagctgccag   1020

gagtgcacgc gcgtctacga cgtgcacacc tgcaagtag                          1059


<210> SEQ ID NO 51
<211> LENGTH: 352
<212> TYPE: PRT
<213> ORGANISM: Artificial Sequence
<220> FEATURE:
<223> OTHER INFORMATION: human Wnt3a polypeptide sequence

<400> SEQUENCE: 51

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60
```

```
Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350


<210> SEQ ID NO 52
<211> LENGTH: 1977
<212> TYPE: DNA
<213> ORGANISM: Artificial Sequence
<220> FEATURE:
<223> OTHER INFORMATION: beta-arrestin2-GFP nucleotide sequence

<400> SEQUENCE: 52

atgggtgaaa aacccgggac cagggtcttc aagaagtcga gccctaactg caagctcacc      60

gtgtacttgg gcaagcgtga ctttgtggat cacttggaca aagtggatcc tgtcgatggt     120

gtggtgcttg tggatcctga ctacttgaag gaccggaaag tgtttgtgac cctcacctgt     180

gccttccgct atggccgaga agacctggat gtactgggcc tgtctttccg caaagatctg     240

ttcatcgcca cctaccaggc cttccccccc atgcccaacc cacctcggcc ccccacccgc     300

ctacaggacc gactgctgaa gaagttgggc cagcatgccc acccctttt tttcacaata      360

ccccagaatt tgccttgctc cgtcacactg cagccaggac cggaggacac agggaaggcc     420

tgtggagtag actttgagat tcgagccttc tgtgccaaat ctatagaaga aaaaagccac     480
```

```
aaaaggaact ccgtgcggct tatcatcaga aaggtacagt ttgctcctga gacacccggc    540

ccccagccat cagctgaaac cacacgccac ttcctcatgt ctgaccggag gtccctgcac    600

ctagaggctt ccctggacaa agagctgtac taccatgggg aacccctcaa tgtcaacgtc    660

cacgtcacca acaattctgc caagaccgtc aagaagatca gagtgtctgt gagacagtat    720

gccgacattt gcctcttcag caccgcgcag tacaagtgtc ctgtggctca gcttgaacaa    780

gatgaccagg tgtctcccag ttccacattc tgcaaggtgt acaccataac cccgctgctc    840

agtgacaacc gagagaagcg tggccttgcc cttgatgggc aactcaagca cgaagacacc    900

aacctggctt ccagcaccat tgtgaaggag ggagccaaca aggaggtgct gggaatccta    960

gtatcctaca gggtcaaggt gaagctggtg gtgtctcgag gcggggatgt ctccgtggag   1020

ctacctttcg tcctaatgca ccccaagccc cacgaccaca tcacccttcc ccgaccccag   1080

tcagcccccc gggaaataga catccctgtg gataccaacc tcattgaatt cgataccaac   1140

tatgccacag acgacgacat cgtgtttgag gactttgcga ggcttcggct gaaggggatg   1200

aaggatgacg actgtgatga ccagttctgc tacggatcca tcgccaccat gggtaaagga   1260

gaagaacttt tcactggagt tgtcccaatt cttgttgaat tagatggtga tgttaatggg   1320

cacaaatttt ctgtcagtgg agagggtgaa ggtgatgcaa catacggaaa acttaccctt   1380

aaatttattt gcactactgg aaaactacct gttccatggc caacacttgt cactactttt   1440

acgtatggtg ttcaatgctt ttcaagatac ccagatcata tgaaacggca tgactttttc   1500

aagagtgcca tgcccgaagg ttatgtacag gaaagaacta tatttttcaa agatgacggg   1560

aactacaaga cacgtgctga agtcaagttt gaaggtgata cccttgttaa tagaatcgag   1620

ttaaaaggta ttgattttaa agaagatgga aacattcttg gacacaaatt ggaatacaac   1680

tataactcac acaatgtata catcatggca gacaaacaaa agaatggaat caaagttaac   1740

ttcaaaatta gacacaacat tgaagatgga agcgttcaac tagcagacca ttatcaacaa   1800

aatactccaa ttggcgatgg ccctgtcctt ttaccagaca accattacct gtccacacaa   1860

tctgcccttt cgaaagatcc caacgaaaag agagaccaca tggtccttct tgagtttgta   1920

acagctgctg ggattacaca tggcatggat gaactataca agtccggatc tagataa      1977
```

<210> SEQ ID NO 53
<211> LENGTH: 658
<212> TYPE: PRT
<213> ORGANISM: Artificial Sequence
<220> FEATURE:
<223> OTHER INFORMATION: beta-arrestin2-GFP polypeptide sequence

<400> SEQUENCE: 53

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95
```

```
Pro Pro Thr Arg Leu Gln Asp Arg Leu Leu Lys Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Thr Arg His Phe Leu
            180                 185                 190

Met Ser Asp Arg Arg Ser Leu His Leu Glu Ala Ser Leu Asp Lys Glu
        195                 200                 205

Leu Tyr Tyr His Gly Glu Pro Leu Asn Val Asn Val His Val Thr Asn
    210                 215                 220

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
                245                 250                 255

Gln Leu Glu Gln Asp Asp Gln Val Ser Pro Ser Ser Thr Phe Cys Lys
            260                 265                 270

Val Tyr Thr Ile Thr Pro Leu Leu Ser Asp Asn Arg Glu Lys Arg Gly
        275                 280                 285

Leu Ala Leu Asp Gly Gln Leu Lys His Glu Asp Thr Asn Leu Ala Ser
    290                 295                 300

Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
                325                 330                 335

Val Ser Val Glu Leu Pro Phe Val Leu Met His Pro Lys Pro His Asp
            340                 345                 350

His Ile Thr Leu Pro Arg Pro Gln Ser Ala Pro Arg Glu Ile Asp Ile
        355                 360                 365

Pro Val Asp Thr Asn Leu Ile Glu Phe Asp Thr Asn Tyr Ala Thr Asp
    370                 375                 380

Asp Asp Ile Val Phe Glu Asp Phe Ala Arg Leu Arg Leu Lys Gly Met
385                 390                 395                 400

Lys Asp Asp Asp Cys Asp Asp Gln Phe Cys Tyr Gly Ser Ile Ala Thr
                405                 410                 415

Met Gly Lys Gly Glu Glu Leu Phe Thr Gly Val Val Pro Ile Leu Val
            420                 425                 430

Glu Leu Asp Gly Asp Val Asn Gly His Lys Phe Ser Val Ser Gly Glu
        435                 440                 445

Gly Glu Gly Asp Ala Thr Tyr Gly Lys Leu Thr Leu Lys Phe Ile Cys
    450                 455                 460

Thr Thr Gly Lys Leu Pro Val Pro Trp Pro Thr Leu Val Thr Thr Phe
465                 470                 475                 480

Thr Tyr Gly Val Gln Cys Phe Ser Arg Tyr Pro Asp His Met Lys Arg
                485                 490                 495

His Asp Phe Phe Lys Ser Ala Met Pro Glu Gly Tyr Val Gln Glu Arg
            500                 505                 510

Thr Ile Phe Phe Lys Asp Asp Gly Asn Tyr Lys Thr Arg Ala Glu Val
```

```
        515                 520                 525

Lys Phe Glu Gly Asp Thr Leu Val Asn Arg Ile Glu Leu Lys Gly Ile
    530                 535                 540

Asp Phe Lys Glu Asp Gly Asn Ile Leu Gly His Lys Leu Glu Tyr Asn
545                 550                 555                 560

Tyr Asn Ser His Asn Val Tyr Ile Met Ala Asp Lys Gln Lys Asn Gly
                565                 570                 575

Ile Lys Val Asn Phe Lys Ile Arg His Asn Ile Glu Asp Gly Ser Val
            580                 585                 590

Gln Leu Ala Asp His Tyr Gln Gln Asn Thr Pro Ile Gly Asp Gly Pro
        595                 600                 605

Val Leu Leu Pro Asp Asn His Tyr Leu Ser Thr Gln Ser Ala Leu Ser
    610                 615                 620

Lys Asp Pro Asn Glu Lys Arg Asp His Met Val Leu Leu Glu Phe Val
625                 630                 635                 640

Thr Ala Ala Gly Ile Thr His Gly Met Asp Glu Leu Tyr Lys Ser Gly
                645                 650                 655

Ser Arg


<210> SEQ ID NO 54
<211> LENGTH: 5157
<212> TYPE: DNA
<213> ORGANISM: Artificial Sequence
<220> FEATURE:
<223> OTHER INFORMATION: control plasmid (pIRESpuro3) nucleotide
      sequence

<400> SEQUENCE: 54

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gagctcggat cgatatctgc ggcctagcta gcgcttaagg cctgttaacc ggtcgtacgt    960

ctccggattc gaattcggat ccgcggccgc atagataact gatccagtgt gctggaatta   1020

attcgctgtc tgcgagggcc agctgttggg gtgagtactc cctctcaaaa gcgggcatga   1080

cttctgcgct aagattgtca gtttccaaaa acgaggagga tttgatattc acctggcccg   1140

cggtgatgcc tttgagggtg gccgcgtcca tctggtcaga aaagacaatc tttttgttgt   1200
```

-continued

```
caagcttgag gtgtggcagg cttgagatct ggccatacac ttgagtgaca atgacatcca   1260
ctttgccttt ctctccacag gtgtccactc ccaggtccaa ctgcaggtcg agcatgcatc   1320
tagggcggcc aattccgccc ctctccctcc cccccccta acgttactgg ccgaagccgc   1380
ttggaataag gccggtgtgc gtttgtctat atgtgatttt ccaccatatt gccgtctttt   1440
ggcaatgtga gggcccggaa acctggccct gtcttcttga cgagcattcc taggggtctt   1500
tcccctctcg ccaaaggaat gcaaggtctg ttgaatgtcg tgaaggaagc agttcctctg   1560
gaagcttctt gaagacaaac aacgtctgta gcgacccttt gcaggcagcg gaacccccca   1620
cctggcgaca ggtgcctctg cggccaaaag ccacgtgtat aagatacacc tgcaaaggcg   1680
gcacaacccc agtgccacgt tgtgagttgg atagttgtgg aaagagtcaa atggctctcc   1740
tcaagcgtat tcaacaaggg gctgaaggat gcccagaagg taccccattg tatgggatct   1800
gatctggggc ctcggtgcac atgctttaca tgtgtttagt cgaggttaaa aaaacgtcta   1860
ggccccccga accacgggga cgtggttttc ctttgaaaaa cacgatgata agcttgccac   1920
aacccacaag gagacgacct tccatgaccg agtacaagcc cacggtgcgc ctcgccaccc   1980
gcgacgacgt ccccgggcc gtacgcaccc tcgccgccgc gttcgccgac taccccgcca   2040
cgcgccacac cgtcgacccg gaccgccaca tcgagcgggt caccgagctg caagaactct   2100
tcctcacgcg cgtcgggctc gacatcggca aggtgtgggt cgcggacgac ggcgccgcgg   2160
tggcggtctg gaccacgccg gagagcgtcg aagcgggggc ggtgttcgcc gagatcggcc   2220
cgcgcatggc cgagttgagc ggttcccggc tggccgcgca gcaacagatg gaaggcctcc   2280
tggcgccgca ccggcccaag gagcccgcgt ggttcctggc caccgtcggc gtctcgcccg   2340
accaccaggg caagggtctg ggcagcgccg tcgtgctccc cggagtggag gcggccgagc   2400
gcgccggggt gcccgccttc ctggagacct ccgcgccccg caacctcccc ttctacgagc   2460
ggctcggctt caccgtcacc gccgacgtcg agtgcccgaa ggaccgcgcg acctggtgca   2520
tgacccgcaa gcccggtgcc tgacgcccgc cccacgaccc gcagcgcccg accgaaagga   2580
gcgcacgacc ccatggctcc gaccgaagcc gacccgggcg gccccgccga ccccgcaccc   2640
gcccccgagg cccaccgact ctagataact gatcataatc agccatacca catttgtaga   2700
ggttttactt gctttaaaaa acctcccaca cctccccctg aacctgaaac ataaaatgaa   2760
tgcaattgtt gttgttaact tgtttattgc agcttataat ggttacaaat aaagcaatag   2820
catcacaaat ttcacaaata aagcattttt ttcactgcat tctagttgtg gtttgtccaa   2880
actcatcaat gtatcttaac gcgtcgagtg cattctagtt gtggtttgtc caaactcatc   2940
aatgtatctt atcatgtctg tataccgtcg acctctagct agagcttggc gtaatcatgg   3000
tcatagctgt ttcctgtgtg aaattgttat ccgctcacaa ttccacacaa catacgagcc   3060
ggaagcataa agtgtaaagc ctggggtgcc taatgagtga gctaactcac attaattgcg   3120
ttgcgctcac tgcccgcttt ccagtcggga aacctgtcgt gccagctgca ttaatgaatc   3180
ggccaacgcg cggggagagg cggtttgcgt attgggcgct cttccgcttc ctcgctcact   3240
gactcgctgc gctcggtcgt tcggctgcgg cgagcggtat cagctcactc aaaggcggta   3300
atacggttat ccacagaatc aggggataac gcaggaaaga acatgtgagc aaaaggccag   3360
caaaaggcca ggaaccgtaa aaaggccgcg ttgctggcgt ttttccatag gctccgcccc   3420
cctgacgagc atcacaaaaa tcgacgctca agtcagaggt ggcgaaaccc gacaggacta   3480
taaagatacc aggcgtttcc ccctggaagc tccctcgtgc gctctcctgt tccgaccctg   3540
ccgcttaccg gatacctgtc cgcctttctc ccttcgggaa gcgtggcgct ttctcaatgc   3600
```

-continued

```
tcacgctgta ggtatctcag ttcggtgtag gtcgttcgct ccaagctggg ctgtgtgcac   3660

gaaccccccg ttcagcccga ccgctgcgcc ttatccggta actatcgtct tgagtccaac   3720

ccggtaagac acgacttatc gccactggca gcagccactg gtaacaggat tagcagagcg   3780

aggtatgtag gcggtgctac agagttcttg aagtggtggc ctaactacgg ctacactaga   3840

aggacagtat ttggtatctg cgctctgctg aagccagtta ccttcggaaa aagagttggt   3900

agctcttgat ccggcaaaca aaccaccgct ggtagcggtg gtttttttgt ttgcaagcag   3960

cagattacgc gcagaaaaaa aggatctcaa gaagatcctt tgatcttttc tacggggtct   4020

gacgctcagt ggaacgaaaa ctcacgttaa gggattttgg tcatgagatt atcaaaaagg   4080

atcttcacct agatcctttt aaattaaaaa tgaagtttta aatcaatcta aagtatatat   4140

gagtaaactt ggtctgacag ttaccaatgc ttaatcagtg aggcacctat ctcagcgatc   4200

tgtctatttc gttcatccat agttgcctga ctccccgtcg tgtagataac tacgatacgg   4260

gagggcttac catctggccc cagtgctgca atgataccgc gagacccacg ctcaccggct   4320

ccagatttat cagcaataaa ccagccagcc ggaagggccg agcgcagaag tggtcctgca   4380

actttatccg cctccatcca gtctattaat tgttgccggg aagctagagt aagtagttcg   4440

ccagttaata gtttgcgcaa cgttgttgcc attgctacag gcatcgtggt gtcacgctcg   4500

tcgtttggta tggcttcatt cagctccggt tcccaacgat caaggcgagt tacatgatcc   4560

cccatgttgt gcaaaaaagc ggttagctcc ttcggtcctc cgatcgttgt cagaagtaag   4620

ttggccgcag tgttatcact catggttatg gcagcactgc ataattctct tactgtcatg   4680

ccatccgtaa gatgcttttc tgtgactggt gagtactcaa ccaagtcatt ctgagaatag   4740

tgtatgcggc gaccgagttg ctcttgcccg gcgtcaatac gggataatac cgcgccacat   4800

agcagaactt taaaagtgct catcattgga aaacgttctt cggggcgaaa actctcaagg   4860

atcttaccgc tgttgagatc cagttcgatg taacccactc gtgcacccaa ctgatcttca   4920

gcatctttta ctttcaccag cgtttctggg tgagcaaaaa caggaaggca aaatgccgca   4980

aaaaagggaa taagggcgac acggaaatgt tgaatactca tactcttcct ttttcaatat   5040

tattgaagca tttatcaggg ttattgtctc atgagcggat acatatttga atgtatttag   5100

aaaaataaac aaataggggt tccgcgcaca tttccccgaa aagtgccacc tgacgtc      5157
```

REGULATION OF WNT/BETA-CATENIN SIGNALING

This application claims priority to U.S. Provisional Patent Application Ser. No. 61/488,643, entitled "REGULATION OF WNT/BETA-CATENIN SIGNALING," filed on May 20, 2011, the entire content of which is hereby incorporated by reference.

BACKGROUND

The present invention relates generally to the field of cell signaling pathways involved in cancer, and more specifically to identifying ligands involved in the regulation of Wnt/β-catenin signaling, and to detecting the ability of a compound to modulate the activity of a receptor in a cell.

The Wnt/β-catenin signaling pathway is essential for development and stem cell survival and is aberrantly activated in cancer. The Wnt/β-catenin signaling pathway, also called the canonical pathway of Wnt signaling, is one of the most fundamental mechanisms that control cell proliferation and cell fate determination during embryonic development and tissue generation. Signaling of this pathway is initiated by the binding of a Wnt ligand to its co-receptors, Frizzled and LRP5/6, to form a complex that recruits Dishevelled (Dsh), Axin and GSK3, and then internalizes into large multivesicular bodies. The process leads to inhibition of GSK3 activity and thus accumulation of unphosphorylated β-catenin which enters the nucleus. Nuclear β-catenin interacts with transcription factors, such as LEF/TCF, to activate or repress the transcription of Wnt target genes, which then affect cell proliferation and differentiation and provide feedback control during Wnt signaling.

As normal embryogenesis and development are completed, the Wnt/β-catenin signaling pathway becomes essential for the self-renewal and maintenance of adult stem cells. These stem cells are capable of regenerating all cell types of the tissue in which they reside, and are therefore critical to the repair of injured tissues and to the maintenance of tissues with high turnover such as the skin and intestine. Furthermore, adult stem cells are also believed to be the cells-of-origin for many types of cancer since they are already programmed to divide indefinitely. In analogy to normal tissues, many types of cancer are shown to have a hierarchical structure with only a portion of the cells in a tumor mass, the so-called tumor initiating cells or cancer stem cells (CSCs) that can self-renew and are responsible to generate the heterogeneity of the tumor. Therapeutic approaches that can disrupt the homeostasis of CSCs and eradicate them offer the potential of curing the cancer. The Wnt/β-catenin signaling is frequently over-activated in many types of cancer, and is critical to the survival of cancer stem cells. Therefore, targeting this pathway has long been sought for the development of ant-cancer drugs. However, the approach has been challenging due to the complexity and redundancy of the Wnt-FZD-LRP5/6 ligand-receptor system as well as the lack of specific targets in CSCs.

SUMMARY

LGR4, LGR5 and LGR6 function as receptors of R-spondins to regulate Wnt/β-catenin signaling. Adult stem cells are generally identified and traced by one or a set of markers that are specifically expressed in these cells. LGR5 (leucine-rich repeat containing G protein-coupled receptor 5) has been identified and validated as a marker of the crypt basal columnar stem cells along the gastrointestinal tract. This receptor, also known as HG38, GPR49, and FEX, was first reported as an orphan receptor (HG38) with homology to the glycoprotein hormone receptor subfamily of the Class A rhodopsin-like seven transmembrane (7-TM) domain, G protein-coupled receptors (GPCRs). LGR5 is closely related to two other receptors, LGR4 and LGR6 (~50% identity between each other), and together the trio (LGR4-6) form a structurally distinct group of 7-TM receptors that have a substantially large N-terminal extracellular domain comprised of 17 leucine-rich repeats. LGR6 marks a type of stem cells in the hair follicle that are distinct from the LGR5-positive stem cells and can give rise to all cell lineages of the skin.

LGR4 and LGR5 are over-expressed in several types of cancer with higher expression associated with increased metastasis and poorer survival in colon cancer patients. Ectopic expression of LGR4 and LGR5 in tumor cell lines leads to increased invasive activity (LGR4) and proliferation (LGR5) in vitro, and increased tumor formation in vivo while knockdown of their expression has the opposite effect.

Furthermore, LGR5 is expressed much higher in colon cancer stem cells than in non-stem cells. Immunohistochemical studies showed that LGR5-positive cells account for ~5% of cancer cells and are located at the tumor's invasive front, consistent with LGR5 being specifically expressed in cancer stem cells. On the other hand. LGR6 is mutated in ~8% of and its promoter is hypermethylated in ~50% of colon cancer. Despite LGR4-6's critical roles in normal and cancer development and stem cell-specific expression, their endogenous ligands, signaling mechanisms, and potential functions in stem cells remained a mystery.

The present application shows that LGR4-6 function as receptors of R-spondin to affect Wnt/β-catenin signaling. The R-spondins constitute a group of four secreted proteins (RSPO1-4) that were isolated as strong potentiators of Wnt/β-catenin signaling. These proteins share 40-60% identity between each other and a similar structure with a cysteine-rich furin-like domain preceding a thrombospondin-like domain. RSPO1 stimulates the proliferation of intestinal crypt stem cells both in vivo and in vitro through enhancement of Wnt/β-catenin signaling. Furthermore, RSPOs have also been strongly implicated in tumorigenesis. RSPO2 and RSPO3 represent two of the most frequent integrations sites of mouse mammary gland tumor virus (MMTV) in MMTV-induced mammary and colon tumors in the mouse. RSPO2 is over-expressed in ovarian cancer and RSPO3 over-expression transforms normal mammary epithelial cells.

One aspect of the present invention pertains to a composition and method to detect the ability of a compound to modulate the activity of LGR 4, LGR 4, or LGR 6 reception in a cell.

DETAILED DESCRIPTION OF PREFERRED EMBODIMENTS

Figure 1:
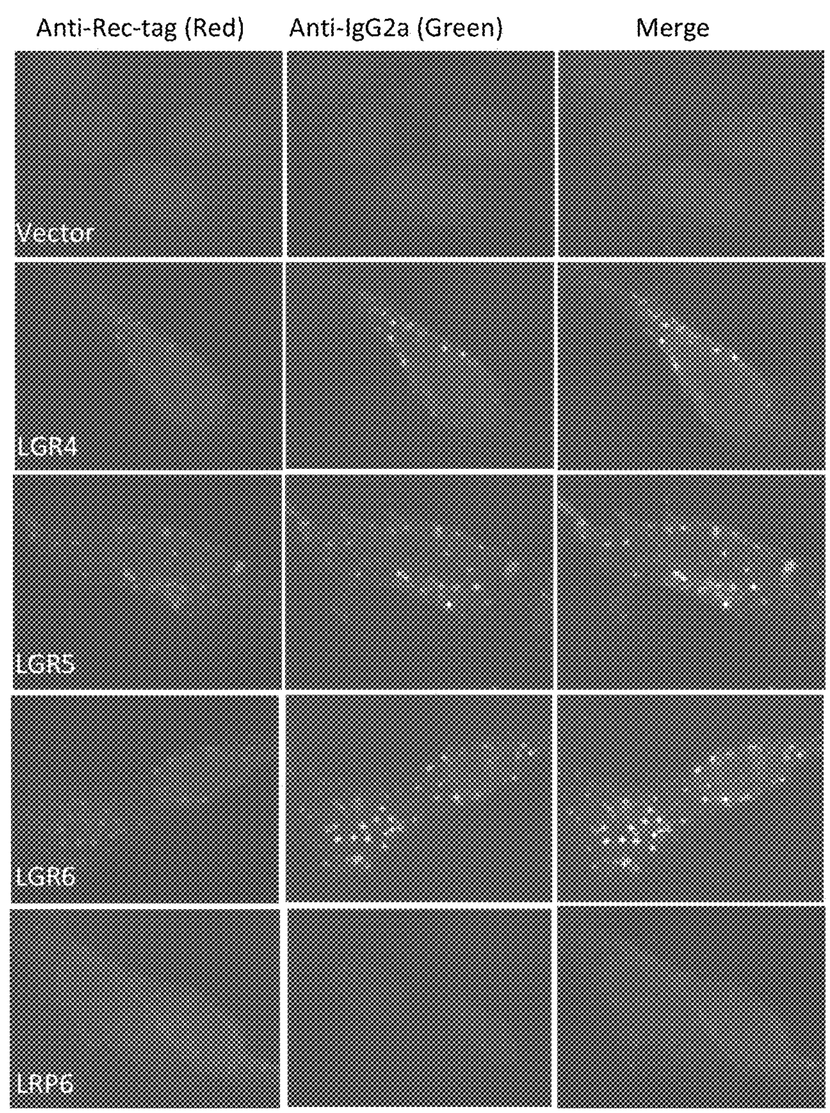
FIG. 1 depicts the binding of mRSPO1-Fc to LGR4-6 by confocal immunofluorescence analysis. HEK293 cells stably expressing Myc-LGR4, Myc-LGR5, FLAG-LGR6, HA-LRP6, or vector alone were incubated with mRSPO1-Fc at 37° C. The cells were then co-stained with fluorescence-labeled anti-tag antibodies (Cy3-anti-Myc, Cy3-anti-FLAG, Alexa Fluor® 594-anti-HA, all three are mouse IgG1 subtype) for receptor detection (left panel) and Alexa Fluor® 488-labeled anti-IgG2a for mRSPO1-Fc detection (middle panel). Nuclei were counter-stained with ToPro-3® (Invitrogen).

The present invention relates generally to the field of cell signaling pathways involved in cancer, and more specifically to the identification of ligands involved in Wnt/β-catenin signaling, or to the detection of the ability of a compound to modulate activity of LGR 4, LGR 5, or LGR 6 receptors in a cell.

In one embodiment, the invention comprises a method for identifying a compound which modulates the activity of a receptor in a cell. The method comprises the steps of: a) contacting the compound and the receptor, and b) determining if the activity of the receptor is modulated by measuring an increase in β-catenin activity in the cell. In this embodiment, the receptor is LGR4 (SEQ ID NO:12, SEQ ID NO:13, SEQ ID NO:14, SEQ ID NO:15), LGR5 (SEQ ID NO:6, SEQ ID NO:7), or LGR6 (SEQ ID NO:8, SEQ ID NO:9). The receptor may also be a sequence having greater than 80% homology to, or whose compliment has greater than 80% homology to SEQ ID NO:12, SEQ ID NO:13, SEQ ID NO:14, SEQ ID NO:15, SEQ ID NO:6, SEQ ID NO:7, SEQ ID NO:8, SEQ ID NO:9. The activity of the receptor is modulated if β-catenin activity in the cell is greater than β-catenin in a cell which has not been exposed to the compound.

In this embodiment, the β-catenin activity in the cell may be measured by transfecting the cell with a β-catenin reporter plasmid carrying firefly luciferase and a control plasmid carrying renilla luciferase, and measuring the firefly luciferase activity and the renilla luciferase activity for a population of transfected cells. β-catenin activity is increased if the ratio of firefly luciferase activity over renilla luciferase activity for a population of cells is increased. The β-catenin reporter plasmid may have the sequence SEQ ID NO:45.

In another embodiment, the invention comprises a composition for identifying a compound which modulates the activity of a receptor in a cell, comprising: a) a β-catenin reporter plasmid carrying firefly luciferase; and b) a control plasmid carrying renilla luciferase. The β-catenin reporter plasmid may have the sequence SEQ ID NO:45.

In another embodiment, the invention comprises a composition for modulating growth or proliferation in a cell, comprising a compound capable of binding LGR4, LGR5, or LGR6; wherein the compound is capable of binding LGR4. LGR5, or LGR6 if β-catenin activity in a cell exposed to the compound is greater than β-catenin in a cell which has not been exposed to the compound. The compound may be a small molecule or an antibody.

In one embodiment, the invention comprises a composition for modulating growth or proliferation in a cell, comprising a compound capable of binding LGR4, LGR5, or LGR6, which is also capable of modulating Wnt/beta-catenin signaling through these receptors.

EXAMPLE 1

Binding of mRSPO1-Fc to LGR4-6 by Confocal Immunofluorescence Analysis

Figure 2:
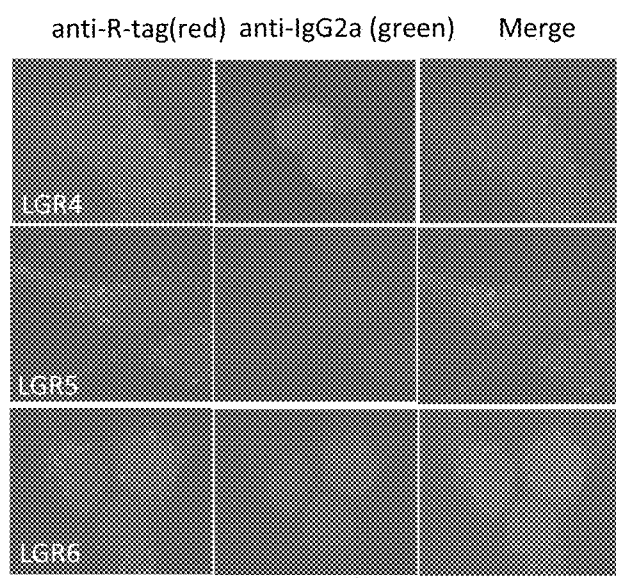
FIG. 2 depicts binding control without mRSPO1-Fc. The binding reactions were carried out side-by-side with those of FIG. 1, except control conditioned media (CM) without mRSPO1-Fc was added to the cells. Receptors were stained with Cy3-labeled anti-Myc (red, LGR4 and LGR5) or Cy3-labeled anti-FLAG (red, LGR6). Alexa Fluor 488®-labeled anti-mouse IgG2a (middle panel) were used to stain mRSPO1-Fc. Nuclei were counter-stained with To-PRO-3®.

Plasmids containing the full-length open reading frames of LGR4-6 were purchased from Open Biosystems. For LGR4, the open reading frame encoding a predicted mature form of the mouse gene (aa23-951, Genbank accession number NP_766259) was fused with sequences encoding an HA tag (SEQ ID NO:1, SEQ ID NO:2) or a Myc-tag (SEQ ID NO:3, SEQ ID NO:4) at the N-terminus, and cloned downstream of a sequence encoding the CD8 signal peptide (MALPVTALLLPLALLLHAA (SEQ ID NO:5) in the vector pIRESpuro3 (Clontech; SEQ ID NO: 54) using standard, PCR-based molecular cloning procedures. The open reading frames encoding the predicted mature forms of human LGR5 (SEQ ID NO:6; aa21-907, Genbank accession number NP_003658 (SEQ ID NO:7)) and human LGR6 (SEQ ID NO:8; aa25-967, Genbank accession number NP_001017403 (SEQ ID NO:9)) were fused at the N-terminus with sequences encoding a Myc tag (LGR5) or a FLAG tag (LGR6) (SEQ ID NO:10; SEQ ID NO:11) and cloned into the same vector as LGR4 (SEQ ID NO:12; SEQ ID NO:13; SEQ ID NO:14; SEQ ID NO:15). All clones were verified by sequencing. HEK293 cells were grown in DMEM supplemented with 10% FCS (fetal calf serum) and penicillin/streptomycin in a 37° C. incubator with 95% humidity and 5% $CO_2$. Plasmids of Myc-LGR4, Myc-LGR5 and FLAG-LGR6 were transfected into HEK293 using FuGene® 6 (Roche), and bulk stable cells were selected and maintained with puromycin at 1 δg/ml. For the production of mRSPO1-Fc, HEK293 cells were transiently transfected with the mRSPO1-Fc plasmid or vector alone using Lipofectamine-2000 (Invitrogen) and incubated for two days. The cells were then switched to serum-free OPTI-MEM®® media (Invitrogen), and incubated for 3 days. The media were collected and briefly centrifuged to remove cell debris, and then concentrated by ~40-fold using Amicon. Ultra-15 10K filter devices with a MW cutoff of 10 kD. The concentration of mRSPO1-Fc was estimated to be ~0.5 μM using the AlphaScreen® HA assay kit (Perkin Elmer), as the fusion protein has an HA tag at the N-terminus The day prior to experimentation, cells stably expressing control vector, Myc-LGR4, Myc-LGR5, FLAG-LGR6, or HA-LRP6 were seeded in poly-D-lysine-coated 8-well culture slides (Becton Dickinson). Media were removed and the cells were gently rinsed with ice-cold phosphate-buffered saline (PBS). Concentrated CM with and without mRSPO1-Fc were diluted by 1:100 in ice-cold OPTI-MEM®+0.5% bovine serum albumin (BSA) and then added to the cells. The slide was incubated for 45 min at 37° C. The cells were washed 3× with cold PBS, fixed in 4% paraformaldehyde/PBS for 15 min at room temperature and then washed 3× with PBS with gentle agitation. The cells were permeabilized with 0.1% saponin/PBS followed by three additional washings with PBS. The cells were then co-stained with Alexa Fluor® 488-labeled goat anti-mouse IgG2a (Invitrogen) at 1:100 dilution in OPTI-MEM®+0.5% BSA plus Cy3-labeled anti-Myc (Sigma, for LGR4 and LGR5 cells), or Cy3-labeled anti-FLAG (Sigma, for LGR6 cells), or Alexa Fluor® 594-labeled anti-HA (Invitrogen, for LRP6 cells) for 1 hr at room temperature. Anti-tag antibodies were used at 1:200 dilution. The cells were then washed 3× with PBS. Nuclei were counter-stained with TO-PRO®-3 iodide (Invitrogen) at 1 μM for 15 min at room temperature. Images were recorded and analyzed using confocal laser scanning microscopy (Leica TCS SP5 microscope) with the LAS AF Lite software.

mRSPO1-Fc (SEQ ID NO:16; SEQ ID NO:17) was observed to bind to cells expressing any of LGR4-6, but not to cells expressing vector only (FIG. 1). Fluorescent anti-receptor tag antibodies identified the location of each receptor in the cells (FIG. 1, middle column). Superimposing of the two images revealed near complete co-localization of mRSPO1-Fc with each of the three receptors (as shown in FIG. 1, right column), indicating that mRSPO1-Fc was co-internalized with LGR4-6. No non-specific Fc-associated staining was observed in the absence of mRSPO1-Fc, as shown in FIG. 2.

Figure 3:
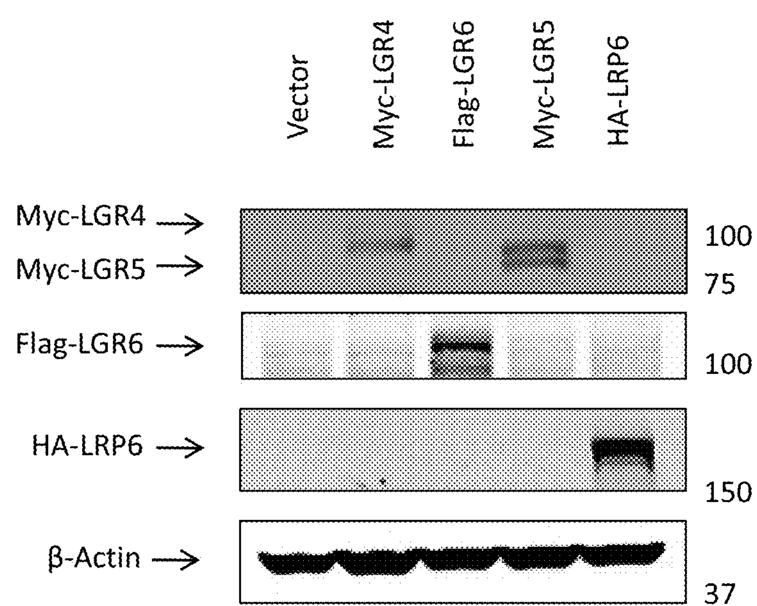
FIG. 3 depicts immunoblotting analysis of the cell lines stably expressing Myc-LGR4, Myc-LGR5, FLAG-LGR6, and HA-LRP6. Total cell lysates were probed with anti-Myc (LGR4 and LGR5 cells), anti-FLAG (LGR6 cells), and anti-HA (LRP6 cells) antibodies. β-actin was also probed as loading control.

In addition, HEK293 cells lines stably overexpressing LRP6 were also tested for binding of mRSPO1-Fc. Though the cells exhibited strong expression of LRP6, no mRSPO1-Fc binding was detected (FIG. 1, bottom row), indicating no direct interaction between mRSPO1-Fc and LRP6. The expression of LGR4-6 and LRP6 in the respective cell lines was confirmed by immunoblot analysis (FIG. 3).

EXAMPLE 2

The Binding of RSPO1 to LGR5 as Demonstrated by Co-Precipitation

Figure 4:
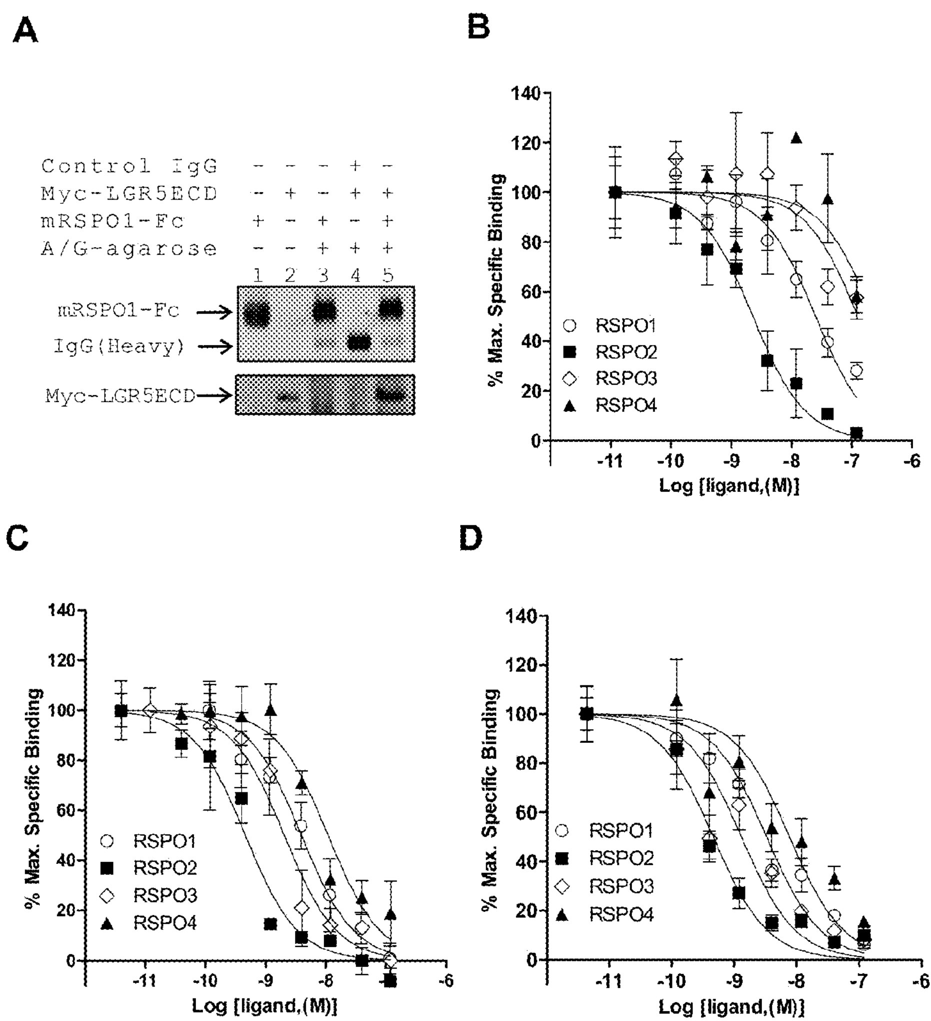
FIG. 4 depicts the binding of RSPO1-4 to LGR4-6 by co-precipitation and competition analysis. (A) Coprecipitation of LGR5ECD to mRSPO1-Fc. Pull-down samples (lanes 3-5) were probed with anti-mouse IgG antibody (top panel) or with anti-Myc antibody (bottom panel). Lanes 1 and 2 are input control. (B-D) Quantitative binding analysis using a whole-cell based assay. HEK293 cells stably expressing Myc-LGR4 (B), Myc-LGR5 (D), or FLAG-LGR6 (D) were incubated with mRSPO1-Fc at ~5 nM plus serial dilutions of purified recombinant RSPO1-4 for 3-4 hrs at 4° C. Binding of mRSPO1-Fc was detected with Alexa Fluor® 647-labeled anti-mouse IgG. Maximum specific binding is defined by the difference between the data of with and without mRSPO1-Fc which is approximately 50% of total binding in general. All error bars are S.E.M. (n=4).

A direct interaction between the ECD of LGR5 (SEQ ID NO:18; SEQ ID NO:19) and mRSPO1-Fc was demonstrated using immunoprecipitation. CM from HEK293 cells transiently transfected with mRSPO1-Fc and from HEK293 cells stably expressing Myc-LGR5ECD were pre-cleared with washed protein A/G plus-agarose beads (Santa Cruz Biotechnology) for 1 hr at 4° C. (40 μl of solid beads per ml of medium, plus protease inhibitor and 1 mM PMSF). The pre-cleared CM containing mRSPO1-Fc or control mouse IgG was mixed with pre-cleared CM containing Myc-LGR5ECD and incubated overnight at 4° C. Fresh A/G-agarose beads were added, and the mixtures were incubated for 2 hrs at 4° C. and then washed 2× in RIPA buffer (50 mM Tris-Cl pH7.4, 150 mM NaCl, 1 mM DTT, 1% Triton X-100, 1% Sodium deoxycholate, 0.1% SDS). The samples were then boiled for 3 min in 1× Laemmli buffer, resolved by SDS-PAGE, and analyzed using anti-Myc and anti-mouse IgG antibodies by standard immunoblotting procedures. FIG. 4A shows the results of a co-precipitation of mRSPO1-Fc with LGR5ECD, but not with control IgG, indicating direct interaction between mRSPO1-Fc and LGR5. Lanes 1 and 2 are input controls and pull-down samples are shown in lanes 3-5, that were probed with anti-mouse IgG antibody (FIG. 4A, top panel) or with anti-Myc antibody (FIG. 4A, bottom panel).

EXAMPLE 3

Quantitative Competition Binding Analysis

A fluorescence-based whole-cell competition binding assay was developed to determine whether purified, recombinant RSP01-4 could compete with mRSPO1-Fc for binding to LGR4-6. HEK293 cells stably expressing Myc-LGR4, Myc-LGR5, or FLAG-LGR6 were seeded into poly-D-lysine-coated 96-well black/clear bottom plates (Becton Dickinson) at ~60,000 cells/well. After overnight culturing, the plates were chilled on ice for 5 min, media were removed from each well, and the cells were washed twice with cold PBS. The recombinant RSPOs under investigation were diluted in 3-fold serial dilutions in cold OPTI-MEM®+0.5% BSA and added onto the cells at 50 μl/well, followed immediately by the addition of equal volume of mRSPO1-Fc diluted by 1:100 in the same buffer. The cells were the incubated for 3.5 hrs at 4° C. with gentle agitation, followed by three quick washes with cold PBS. The cells were then fixed in 4% paraformaldehyde/PBS for 15 min at room temperature and washed 3× with PBS. The cells were further incubated with Alexa Fluor® 647-labeled goat anti-mouse IgG (H+L) (Invitrogen, diluted by 1:200) in OPTI-MEM®+0.5% BSA for 1 hr at room temperature. The cells were washed thrice with PBS and fluorescence intensity was measured using a Tecan M1000 plate reader with excitation at 630 nm and emission at 670 nm. All experiments were performed at least twice with quadruplicate replicates in each experiment. HEK293 cells stably expressing Myc-LGR4 (shown in FIG. 4B), Myc-LGR5 (shown in FIG. 4C), or FLAG-LGR6 (shown in FIG. 4D) were incubated with mRSPO1Fc at ~5 nM plus serial dilutions of purified recombinant RSPO1-4 for 3-4 hrs at 4° C. Binding of mRSPO1-Fc was detected with Alexa Fluor® 647-labeled anti-mouse IgG. Maximum specific binding is defined by the difference between the data of with and without mRSPO1-Fc which is approximately 50% of total binding in general. All error bars are S.E.M. (n=4). Selective binding of a receptor was indicated when the IC50 was determined to be less than or equal to 1 μM (micro Molar). As shown in FIGS. 4B-D, RSPO1-4 were able to completely displace the binding of mRSPO1-Fc to LGR4-6 with IC50's in the nM range, the one exception was the μM IC50's for RSPO3 (SEQ ID NO:46; SEQ ID NO:47) and RSPO4 (SEQ ID NO:48; SEQ ID NO:49) binding to LGR4. Taken together, these results indicated that RSPO1-4 can specifically bind to LGR4-6 with RSPO2 demonstrating the highest affinity to all three receptors.

EXAMPLE 4

Potentiation of Wnt/β-Catenin Signaling by LGR4-6 in Response to RPSO1-4

A β-catenin-responsive reporter assay was used to characterize the effect of treatment with RSPO1-4 on Wnt/β-catenin signaling in HEK293T cells individually over-expressing LGR4-6 in the presence of Wnt3a (SEQ ID NO:50; SEQ ID NO:51) conditioned media (CM). HEK293T cells were cultured in 6-well plates, and transient transfections were performed using FuGene® HD (Roche Applied Sciences, Indianapolis, Ind.) according to the manufacturer's suggested protocol. For transfection, 1 μg of the Super 8× TOPFlash reporter and 100 ng of pRL-SV40 plasmid were used. LGR4-6 constructs and vector control were transfected at 1 μg/well and LRP6 wild-type and mutant constructs were transfected at 500 ng/well. The total amount of vector transfected per well was normalized using the control vector pIRESpuro3. Twenty four hours post transfection, the cells were detached with trypsin and seeded into 384-well plates in OPTI-MEM® containing 1% FCS. Control CM and Wnt3a CM were prepared by culturing L cells and Wnt3a-L cells, respectively, according to the ATCC protocol. Recombinant human RSPO1-4 (R & D Systems) were diluted in control CM or Wnt3aCM in 3-fold serial dilutions and added to the cells at six hours post seeding. The final dilution of control CM or Wnt3a CM was 1:5. After the cells were stimulated overnight, luciferase assay measurements were carried out using the Dual-Glo® luciferase assay kit (Promega) according to the manufacturer's protocol and the plates were read on a PerkinElmer EnVision plate reader. The plasmid Super 8× TOPFlash was purchased from Addgene. pRL-SV40 (SV40 promoter-controlled renilla luciferase) was purchased from Promega. All recombinant proteins were purchased from R&D systems.

All experiments were performed at least twice with quadruplicate replicates in each experiment.

Figure 5:
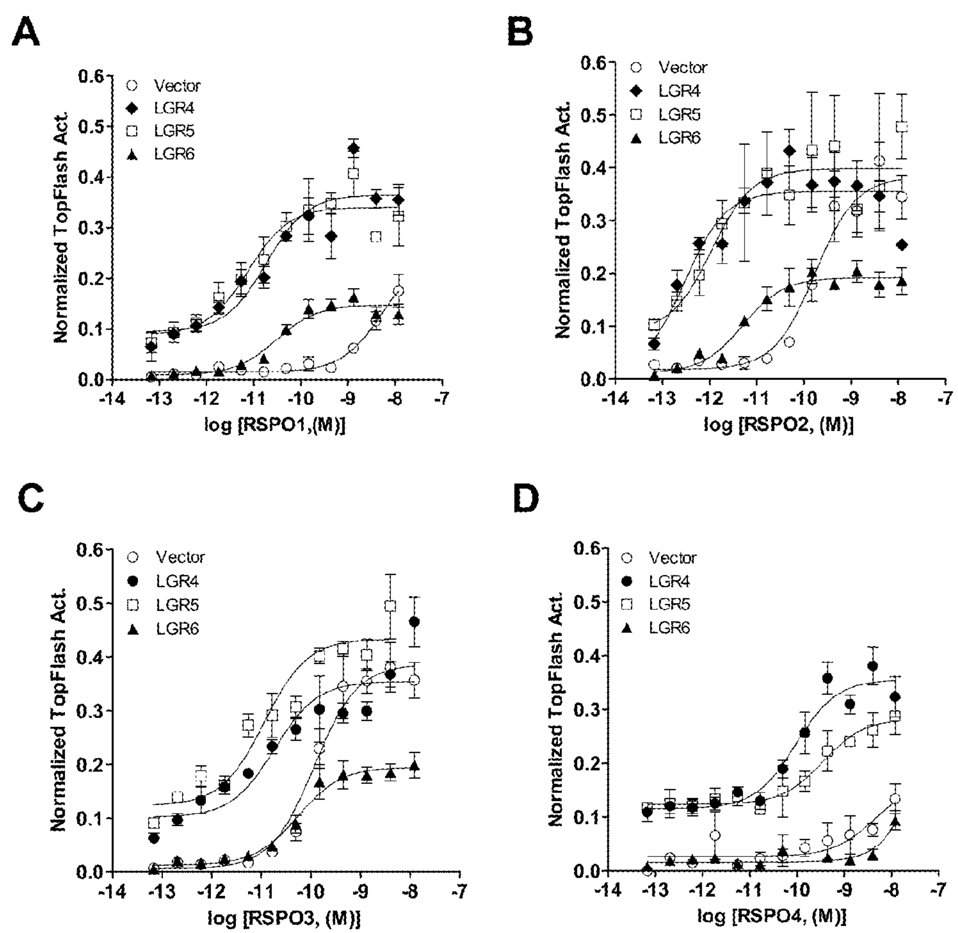
FIG. 5 depicts the potentiation of Wnt/β-catenin signaling by LGR4-6 in response to RPSO1-4. HEK293T cells were transiently transfected with each of LGR4-6 or vector, plus the β-catenin reporter plasmid Super 8× TOPFlash (firefly luciferase) and pRL-SV40 (renilla luciferase) and then stimulated with serial dilutions of purified recombinant RSPO1 (A), RSPO2 (B), RSPO3 (C), or RSPO4 (D) with Wnt3a CM. Firefly luciferase activity of each well was normalized to that of renilla luciferase activity of the same well. All error bars are S.E.M. (n=4).
Figure 6:
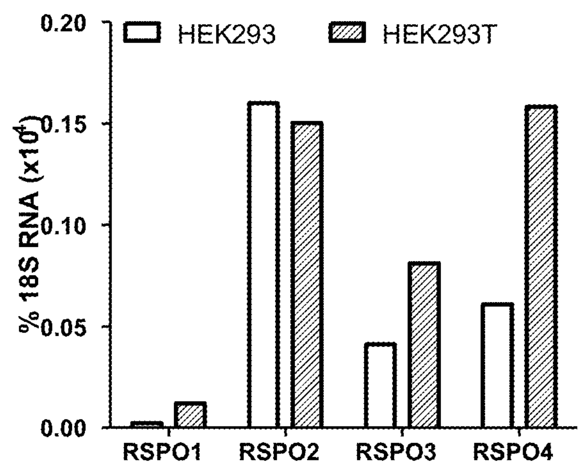
FIG. 6 depicts the result of quantitative PCR analysis of the constitutive expression levels of RSPO1-4 and LGR4-6 in HEK293 and HEK293T cells A, Expression level of RSPO1-4 in HEK293 and HEK293T cells after being normalized to that of 18S RNA. B, Expression level of LGR4-6 in HEK293 and HEK293T cells after being normalized to that of 18s RNA.
Figure 6:
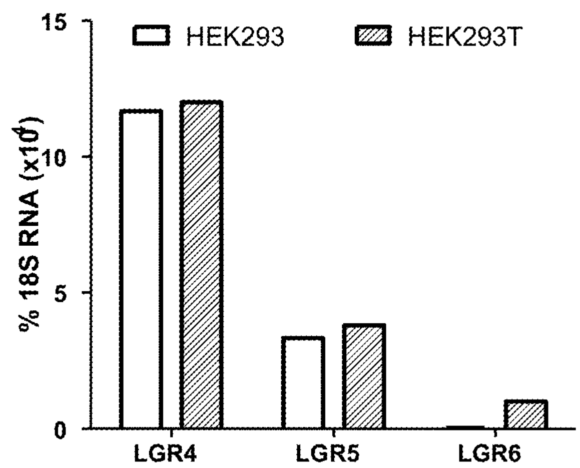
Figure 7:
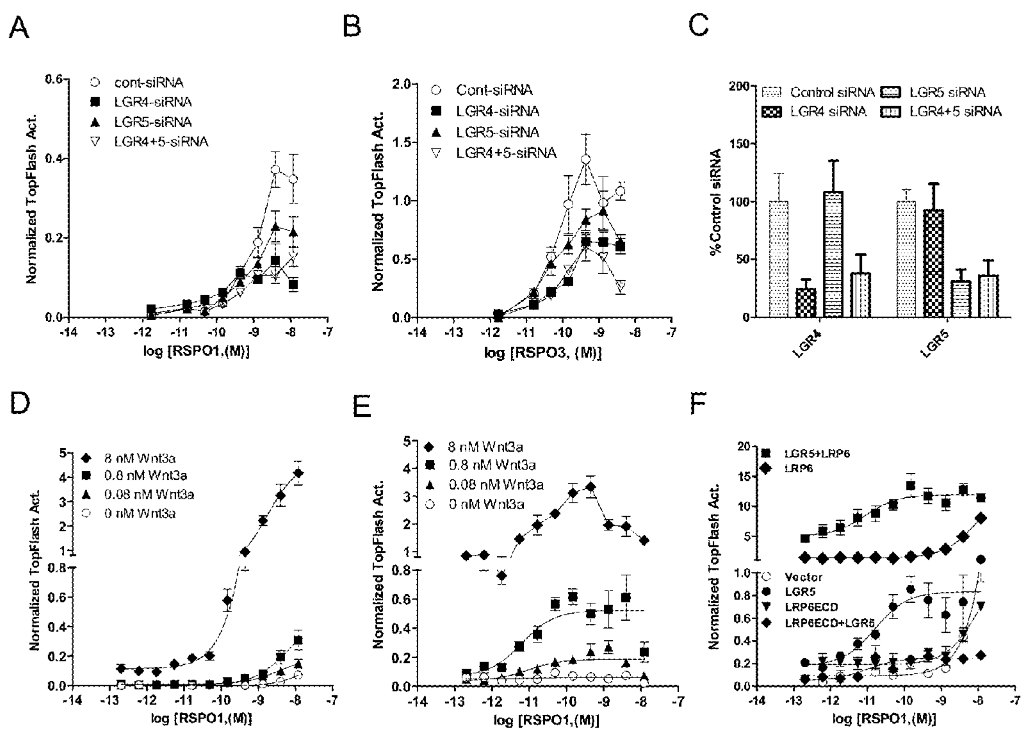
FIG. 7 depicts the effect of LGR4 and LGR5 knockdown, Wnt3a concentration, and LRP6 expression on Wnt/β-catenin signaling potentiation. A-C, siRNA of LGR4, LGR5, or both, and control siRNA were transiently transfected into HEK293T cells. The cells were then transfected with Super 8× TOPFlash and pRL-SV50 plasmids and stimulated with serial dilutions of RSPO1 (A) or RSPO3 (B) in Wnt3a CM. C, Expression levels of LGR4 and LGR5 cells in siRNA-transfected cells. D-E, HEK293T cells were transfected with vector alone (D) or LGR5 (E), plus Super 8× TOPFlash, and pRL-SV40, and stimulated with serial dilutions of RSPO1 in the presence of the indicated concentrations of purified recombinant Wnt3a. F, HEK293T cells were transiently transfected with vector, LGR5, LRP6. LRP6ECD, LRP6+LGR5, or LRP6ECD+LGR5, plus Super 8× TOPFlash and pRL-SV40 plasmids, and stimulated with serial dilutions of RSPO1 in Wnt3a CM. All error bars are S.E.M. (n=4).

Cells transfected with LGR4 or LGR5 displayed dramatic increases in the potencies of RSPO1-4, ranging from 10 to 1000-fold, with no significant change in the maximum activity (Emax) of the reporter enzyme compared to vector-transfected cells (FIG. 5A-D and Table 1). Furthermore, both LGR4 and LGR5-transfected cells showed elevated basal activity relative to vector control cells (FIG. 5A-D). The increased basal activity could be due to constitute receptor activity or endogenous expression of the r-spondins in HEK293 cells (FIG. 6A). On the other hand, cells over-expressing LGR6 demonstrated an increase in the EC50's of RSPO1 and RSPO2 (20-fold), with a decrease (50%) in the Emax, and no change in basal activity (FIG. 5A-D and Table 1). We also demonstrated the effect of RSPO1 depends on the supply of Wnt3a, as shown in FIG. 7. Increasing concentrations of Wnt3a produced a corresponding increase in RSPO1 response (FIG. 7D). In cells over-expressing LGR5, RSPO1 demonstrated higher potency at the same concentration of Wnt3a compared to vector cells (FIG. 7E vs. FIG. 7D). Overall, the data demonstrate that over-expression of LGR4 and LGR5 leads to a dramatic increase in the potency of RSPO1-4 without changing the maximum effect in the potentiation of Wnt/β-catenin signaling. Over-expression of LGR6 had a complex effect: it increased the potency of RSPO1-3, but inhibited maximum activity.

TABLE 1

Binding affinity ($IC_{50}$, nM), potency ($EC_{50}$, nM) and maximum effect (Emax, fraction of vector control) of RSPO1-4 in cells over-expressing LGR4-6.

| | Vector | | | LGR4 | | | LGR5 | | | LGR6 | | |
|---|---|---|---|---|---|---|---|---|---|---|---|---|
| Ligand | $IC_{50}$ | $EC_{50}$ | Emax | $IC_{50}$ | $EC_{50}$ | Emax | $IC_{50}$ | $EC_{50}$ | Emax | $IC_{50}$ | $EC_{50}$ | Emax |
| RSPO1 | ND | NC | NC | 25 | 0.02 | NC | 4.0 | 0.008 | NC | 3.3 | 0.03 | NC |
| RSPO2 | ND | 0.2 | 1 | 2.3 | 0.0003 | 0.9 | 0.5 | 0.001 | 1 | 0.5 | 0.01 | 0.5 |

TABLE 1-continued

Binding affinity ($IC_{50}$, nM), potency ($EC_{50}$, nM) and maximum effect (Emax, fraction of vector control) of RSPO1-4 in cells over-expressing LGR4-6.

| | Vector | | | LGR4 | | | LGR5 | | | LGR6 | | |
|---|---|---|---|---|---|---|---|---|---|---|---|---|
| Ligand | $IC_{50}$ | $EC_{50}$ | Emax | $IC_{50}$ | $EC_{50}$ | Emax | $IC_{50}$ | $EC_{50}$ | Emax | $IC_{50}$ | $EC_{50}$ | Emax |
| RSPO3 | ND | 0.1 | 1 | 126 | 0.02 | 0.9 | 2.1 | 0.01 | 1.1 | 1.3 | 0.05 | 0.5 |
| RSPO4 | ND | NC | NC | 228 | 0.09 | NC | 11 | 0.4 | NC | 7.7 | NC | NC |

ND, not determined; NC, not calculated due to lack of saturation.

EXAMPLE 5

Knockdown with LGR4 and LGR5 siRNA

The strong endogenous response of HEK293T cells to RSPOs in the β-catenin reporter assay suggested that one or more of the LGRs were endogenously expressed in these cells. Quantitative PCR analyses were done by isolation of total RNA from HEK293T and HEK293 cells by lysing the cells with TRIzol® (Invitrogen), followed by the successive addition of chloroform and isopropyl alcohol for phase separation and RNA precipitation, respectively. For further purification, the samples were run through RNeasy Mini Kit columns (Qiagen) according to the manufacturer's protocol. RNA was eluted with RNase-free, DEPC-treated water and then treated with DNase. Quantitative RT-PCR of LGR4-6 and RSPO1-4 was performed by the Quantitative Genomics Core Lab (UT Health, Houston, Tex.). Briefly, a total of 100 ng RNA was run in triplicate per assays (along with no-template and non-amplifying controls) using the Taqman primer/probe combinations listed in the following table (Table 2).

TABLE 2

| Gene Nomen-clature | GenBank Accession No. | Amplicon Length | Amplicon Location | Forward Primer Sequence | Reverse Primer Sequence | Probe Sequence | PCR Efficiency |
|---|---|---|---|---|---|---|---|
| LGR4 | NM_003667 | 80 | Exon 18 | 2559(+) CTTTGTTT GCCATTT C CTA (SEQ ID NO: 20) | 2634(-) CTAGTGA G TTTAATA G CACTAA (SEQ ID NO: 21) | 2586(+) FAM- ACGCCATC AT TAGGATTCA CTGTAAC - BHQ1 (SEQ ID NO: 22) | 99% |
| LGR5 | NM_018490 | 86 | Exon 11/12 Boundary | 1066(+) ATCTCAT C TCTTCCTC AAA (SEQ ID NO: 23) | 1144(-) CTTCTAAT A GGTTGTAA GACA (SEQ ID NO: 24) | 1092(+) FAM- CAATCAGTT A CCTAATCTC C AAGTGCT - BHQ1 (SEQ ID NO: 25) | 95% |
| LGR6 | NM_001017403 | 70 | Exon 20 | 2933(+) CTCTTCC C TTTCCTCT C (SEQ ID NO: 26) | 3001(-) CTGAGTTT T GGTTGTAT T TG (SEQ ID NO: 27) | 2975(-) FAM- AAGCAGCC AT CATTCACCG A -BHQ1 (SEQ ID NO: 28) | 93% |
| RSPO1 | NM_001038633 | 81 | Exon 3/4 Boundary | 487 + TACT C AGTATTA A GGTTGG (SEQ ID NO: 29) | 562- CCTCGGA A TATCATAT G AG (SEQ ID NO: 30) | 515(+) FAM- TAGTCCCTG C TGACGTGA CBHQ1 (SEQ ID NO: 31) | 99% |
| RSPO2 | NM_178565 | 72 | Exon 4/5 Boundary | 1076 + GAA T GTGTGGA A GGATG (SEQ ID NO: 32) | 1143- GTGCGATT ATTTCTGC T A (SEQ ID NO: 33) | 1115(+) FAM- ATTCGCTCC A ATGACCAA CT TC-BHQ1 (SEQ ID NO: 34) | 93% |

TABLE 2-continued

| Gene Nomen-clature | GenBank Accession No. | Amplicon Length | Amplicon Location | Forward Primer Sequence | Reverse Primer Sequence | Probe Sequence | PCR Efficiency |
|---|---|---|---|---|---|---|---|
| RSPO3 | NM_032784 | 87 | Exon 5 | 1007 + ATC C AGCAAAG A AATCC (SEQ ID NO: 35) | 1090-GATACCG A TTTCTGTT T ATC (SEQ ID NO: 36) | 1061(-) FAM-TCGCTTCTT C TGCTGCTGT BHQI (SEQ ID NO: 37) | 94% |
| RSPO4 | NM_001029871 | 77 | Exon 5 | 895 + CTCT G TCTTCTCC ATTTG (SEQ ID NO: 38) | 966-AAAGGGA A GGTAGAC T G (SEQ ID NO: 39) | 915(+) FAM-CTCTCTTTC T TTCCACCCT T CTATCA-BHQI (SEQ ID NO: 40) | 98% |

Quantified expression levels of LGR4-6 and RSPO1-4 were determined from an ssDNA standard curve and expression was normalized to levels of 18S rRNA. Quantitative RT-PCR analysis revealed that all three receptors were expressed in HEK293 and HEK293T cells with the highest expression levels being those of LGR4 (as shown in FIG. 6B). The effect of reduced expression of LGR4 and LGR5 was characterized using knockdown with siRNA as follows. The siRNA used in this study were the human LGR4 and LGR5 ON-Targetplus SMARTpool, and Non-targeting pool derived siRNA were used as negative control (Dharmacon). HEK293T cells were first transfected with the siRNA in Dharmafect 1 (Dharmacon) and 24 hrs later the cells were transfected with Super 8× TOPFlash and pRL-SV40. Following overnight incubation, the cells were seeded into 384-well plates, and stimulated with serial dilutions of RSPO1 (FIG. 7A) or RSPO3 (FIG. 7B) with Wnt3a CM. Luciferase activities were then determined as described To selectively knockdown expression, HEK293T cells were transfected with LGR4-siRNA, LGR5-siRNA, or both. It was determined that cells transfected with LGR4-siRNA or both experienced a ~50% reduction in response to RSPO1, across multiple concentrations (as shown in FIG. 7A). Similar reductions were observed in responses to RSPO3 (as shown in FIG. 7B).

Quantitative RT-PCR analysis confirmed the selectivity of the effect of siRNA with a commensurable decrease in the mRNA levels of LGR4 and LGR5 when exposed to each siRNA or the combination (FIG. 7C). This indicates that the endogenous response to RSPOs in HEK293T cells is mostly mediated by LGR4. This is consistent with the higher level of LGR4 mRNA observed and the robust response seen in response to RSPO1-4 when LGR4 was over-expressed.

Illustrating the requirement for LRP6 to mediate RSPO1-LGR5 activity, it was determined that transfection of LRP6 alone increased Wnt3a-mediated activity by 20-fold, but did not change the potency of RSPO1 (FIG. 7F). Co-transfection of LRP6 with LGR5 increased basal activity by another ~4-fold as compared to transfection of cells with LRP6 alone (FIG. 7F). The potency of RSPO1 in LGR5 transfected cells and LRP6+LGR5 (0.016 and 0.009 nM, respectively) transfected cells were similar, yet much higher than those observed in LRP6-transfected and control cells. Over-expression of the extracellular domain of LRP6 (LRP6ECD, SEQ ID NO:41; SEQ ID NO:42), which acts as a dominant negative form of LRP6, led to the loss of the effect of LGR5. These results further demonstrated that the activity of LGR4 requires the presence of Wnt3a and LRP6 signaling pathway.

EXAMPLE 6

Potentiation is Mediated Through LRP6

Levels of phospho-LRP6 (pLRP6) and active β-catenin were compared in response to treatments with Wnt3a or RSPO1 or both. HEK293T cells were seeded in 10-cm dishes and transiently transfected with Myc-LGR5 plasmid or vector control plasmids using FuGENE® 6 transfection reagent (Roche Applied Sciences, Indianapolis, Ind.). On the next day, the cells were detached, seeded into 6-well plates and cultured overnight in DMEM+10% FCS. They were then changed to DMEM with 1% FCS and incubated overnight, and treated with Wnt3a CM (1:5) or Control CM, with and without RSPO1 for the indicated periods of time. The cells were collected and then lysed with RIPA lysis buffer (50 mM Tris-Cl pH 7.4, 150 mM NaCl, 1 mM DTT, 1% Triton X-100, 1% Sodium deoxycholate, 0.1% SDS) with protease and phosphatase inhibitors.

Phospho-LRP6 was probed with a phospho-Ser1490-specific antibody (Cell signaling #2568) and total LRP6 were probed with an anti-LRP6 polyclonal antibody (Cell Signaling #3395). β-Actin was also probed as protein-loading control. Immunoblotting of cytosolic (non-membrane bound) β-Catenin were carried out using cell lysates that were treated with ConA-sepharose beads for overnight followed by centrifugation to remove cadherin bound β-catenin and probed with the anti-β-catenin antibody that detects total β-catentin (Cell Signaling #9562). Other antibodies used were anti-TCF4 (Cell Signaling #2953) and anti-cyclin D1 (Cell Signaling #2922). All immunoblotting procedures were carried out using HRP-conjugated secondary antibodies by following manufacturers suggested protocols.

Figure 8:
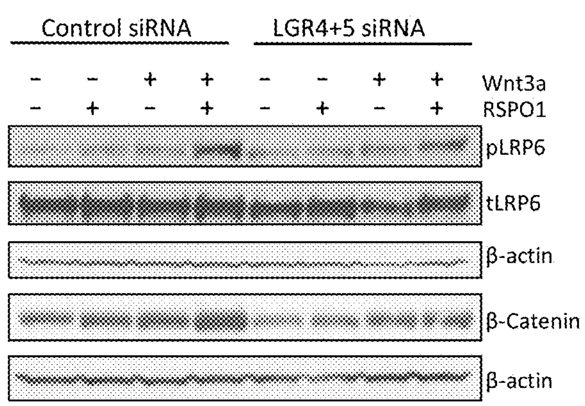
FIG. 8 depicts the effect of LGR4 and LGR5 expression knockdown and LGR5 over-expression on Wnt3a-RSPO1-induced LRP6 phosphorylation and active β-catenin accumulation. A, Effect of LGR4 and LGR5 expression knockdown on endogenous response to Wnt3a-RSPO1 in LRP6 phosphorylation and β-catenin levels. HEK293T cells were co-transfected with LGR4-siRNA and LGR5-siRNA, and two days later, the cells were stimulated with RSPO1 (4 nM) or Wnt3a (3 nM) or both for 3 hrs. Phospho-LRP6 at Ser1490 (pLRP6), total LRP6 (tLRP6), non-membrane-associated β-catenin, and β-actin (loading control) were then probed by immunoblot analysis. B, Change in pLRP6 and active β-catenin levels in response to RSPO1 and Wnt3a treatment in vector and LGR5 cells. HEK293 cells stably expressing vector or LGR5 were stimulated with RSPO1 (0, 3, and 10 ng/ml) with or without Wnt3a CM for 3 hrs, and probed as above. C, Time course of LRP6 phosphorylation and changes in active β-catenin levels following Wnt3a and RSPO1 treatment. The cells were stimulated with RSPO1 (100 ng/ml) and Wnt3a CM for 0-6 hrs, and probed as above.
Figure 8:
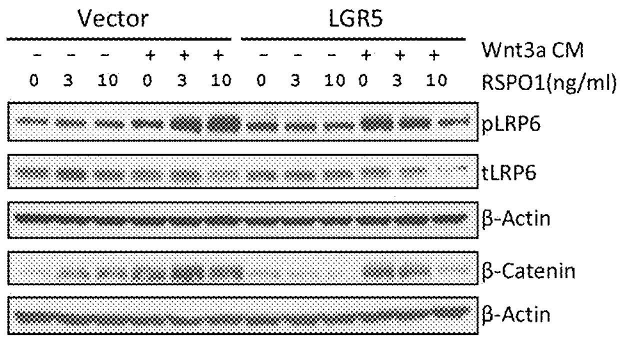
Figure 8:
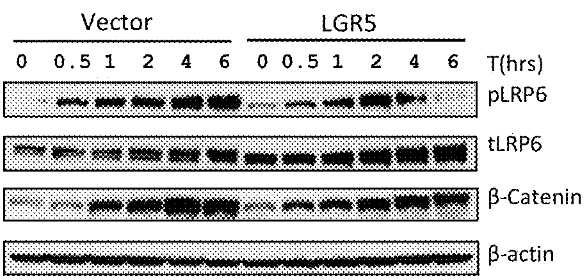
Figure 9:
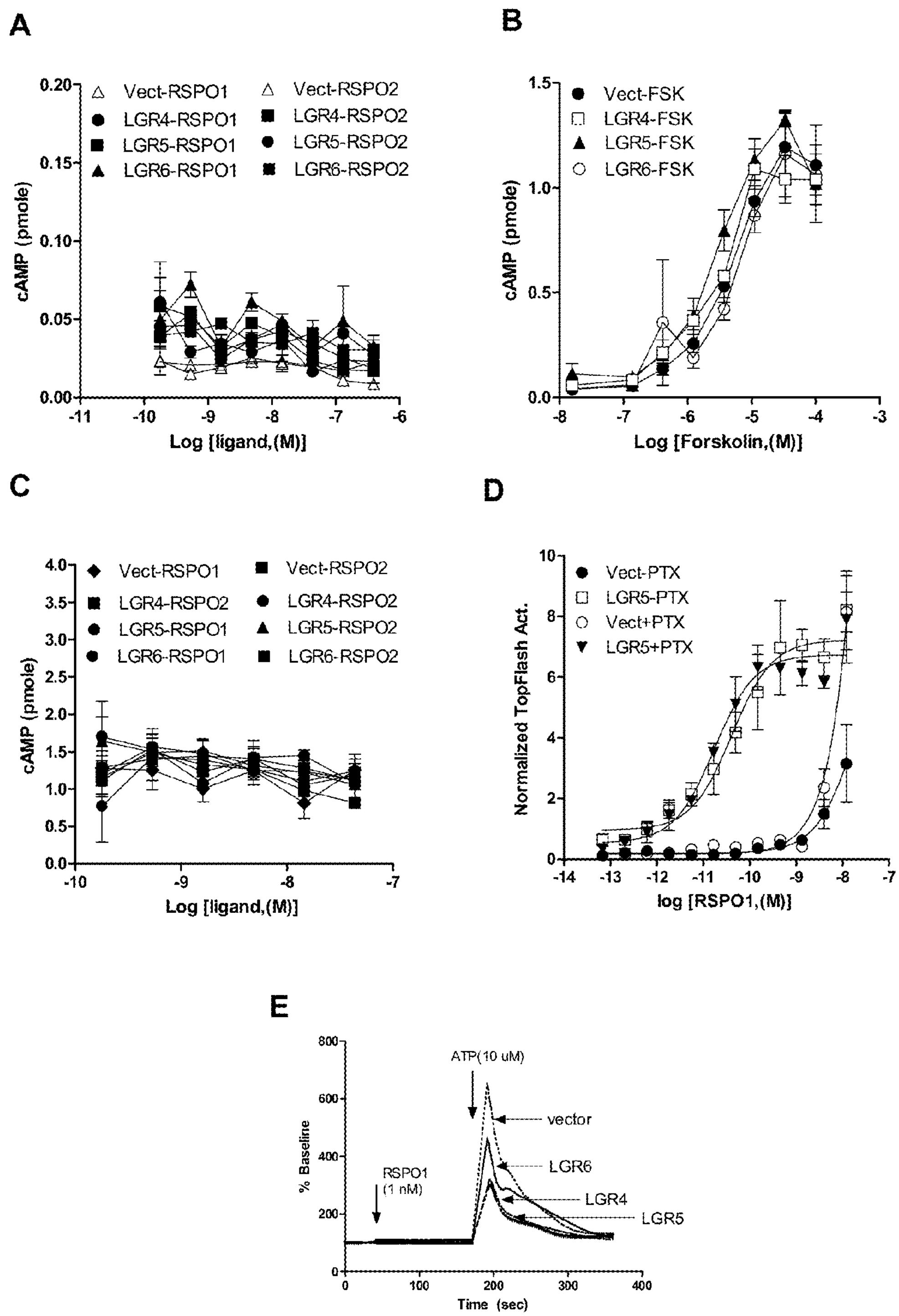
FIG. 9 depicts G protein-coupling assays of LGR4-6 in response to RSPO1-2. (A) cAMP production in vector and LGR4-6 cells treated with RSPO1 and RSPO2. No cAMP response was observed. (B) As positive control, forskolin showed strong stimulation of cAMP production in these cells. (C) RSPO treatments had no effect on forskolin-stimulated cAMP production in vector and LGR4-6 cells. (D) Pertussis toxin had no effect on RSPO1-LGR5-mediated Wnt signaling potentiation. (E) $Ca^{2+}$ mobilization was not induced in vector and LGR4-6 cells in response to RSPO1, while ATP gave a robust response in all cells.

The effect of RSPO1 in vector and LGR5 cells was characterized at different concentrations of purified recombinant Wnt3a. HEK293T cells were transiently transfected with vector or LGR5, and stimulated with RSPO1 (4 nM) or different concentrations of Wnt3a (0.5 or 2.5 nM) or both (as shown in FIG. 8A). Three hours after addition of the ligands, the cells were harvested and probed for levels of phosph-LRP6 (pLRP6) at the Ser1490 site, total LRP6, non-membrane β-catenin (membrane bound β-catenin was removed with Con A-sepharose beads), and β-actin (loading control) by immunoblotting analysis. This confirmed the synergistic effect of RSPO1 and Wnt3a in inducing LRP6 phosphorylation and increasing levels of β-catenin in HEK293 cells (FIG. 8B). Knockdown of the endogenous expression of LGR4 and LGR5 by siRNA led to significant reduction of this effect (FIG. 8A). This finding, taken together with the LGR4- and LGR5-siRNA knockdown data from the β-catenin reporter assay, indicates that the endogenous expression of LGR4 and LGR5 in HEK293 cells is essential for RSPO-induced potentiation of Wnt/β-catenin signaling.

Also examined was the effect of LGR5 over-expression on pLRP6 and active β-catenin following Wnt3a-RSPO1 treatment. HEK293T cells were transiently transfected with vector or LGR5, and stimulated with RSPO1 (4 nM) and Wnt3a CM. The cells were harvested at the indicated time points following the addition of the ligands, and probed as above. LGR5 cells showed increased basal levels of pLRP6 and β-catenin compared to vector cells (FIG. 8B), consistent with increased basal activity in the β-catenin reporter assay (as shown in FIG. 5). Surprising, treatment of Wnt3a and RSPO1 in LGR5 cells led to decreased levels of pLRP6 and active β-catenin (FIG. 8B).

The time course of pLRP6 and active β-catenin between vector and LGR5 cells following treatment with Wnt3a and RSPO1 was also characterized. FIG. 8C illustrates a time course of LRP6 phosphorylation and β-catenin accumulation in HEK293 cells stably expressing LGR5 or vector alone. The cells were stimulated with RSPO1 (4 nM) and Wnt3a CM for various time points between 0-6 hours (hrs), and then harvested and probed as above. In vector cells, the levels of pLRP6 and β-catenin increased with time through 6 hrs (FIG. 8C). In LGR5 cells, pLRP6 also increased with time, but started to decline at 4 hrs and almost totally disappeared at 6 hrs. The level of β-catenin failed to reach the maximum level of the vector cells and began to decline at the 6 hr time point (FIG. 8C). The results suggest that stimulation of cells over-expressing LGR5 with RSPO1 and Wnt3a accelerates either LRP6 dephosphorylation or pLRP6 degradation, as well as enhances β-catenin turnover.

EXAMPLE 7

Potentiation does not Involve G Proteins or β-Arrestin

Figure 10:
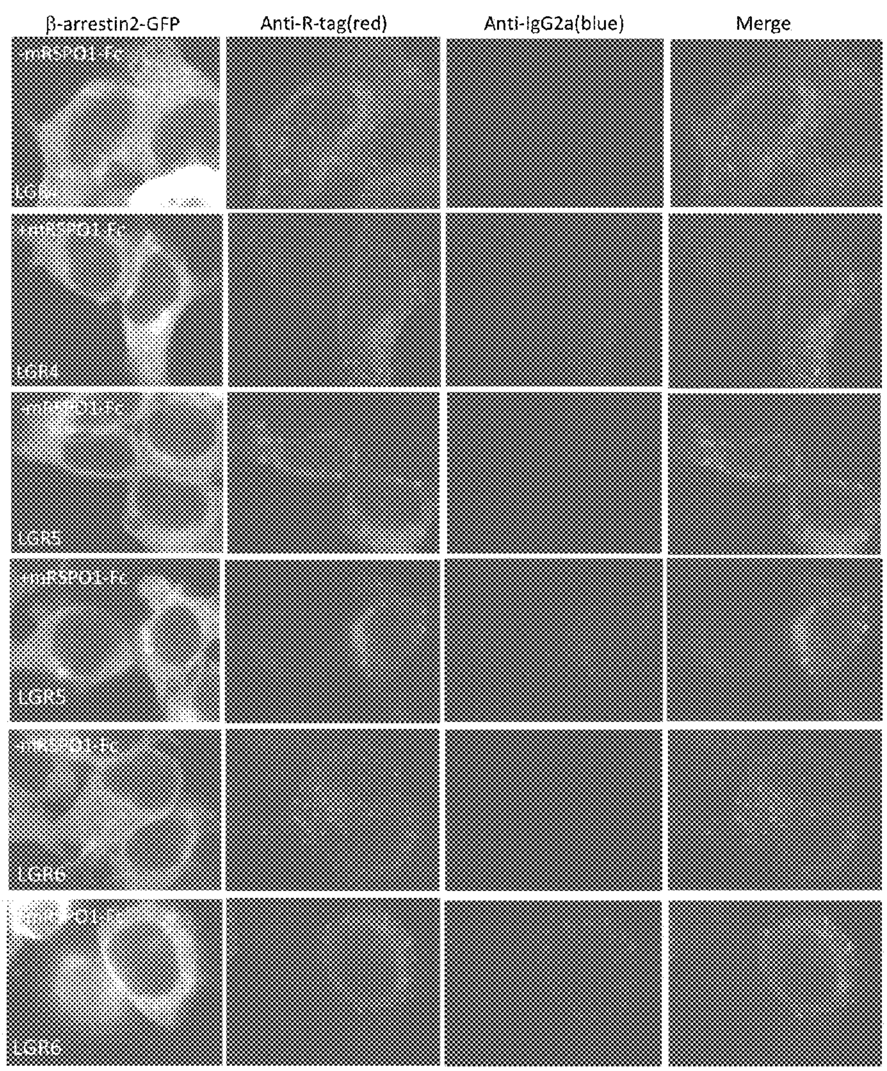
FIG. 10 depicts a β-arrestin translocation assay of LGR4-6 and mRSPO1-Fc. (A) β-arrestin translocation assay of LGR4-6 in HEK293T cells. The cells were co-transfected with β-arrestin2-GFP plus Myc-LGR4, or Myc-LGR5, or FLAG-LGR6. The cells were stimulated with mRSPO1-Fc (~5 nM) or control CM, fixed, permeabilized, and stained with Alexa Fluor 647®-labeled anti-mouse IgG2a plus Cy3-anti-Myc (LGR4 and LGR5 cells) or Cy3-anti-FLAG (LGR6 cells), and viewed by confocal microscopy. No translocation of β-arrestin was observed in LGR4-6 cells treated with mRSPO1-Fc while co-localization of mRSPO1-Fc with each receptor was confirmed. No mRSPO1-Fc associated staining (blue) was observed in cells treated with control CM. (B) As positive control, HE K293T cells were also transfected with β-arrestin2-GFP plus β2-adrenergic receptor (β2-ADR). The cells were then stimulated with isoproterenol (1 μM) or buffer alone. Translocation of β-arrestin following treatment with the agonist was clearly observed.
Figure 10:
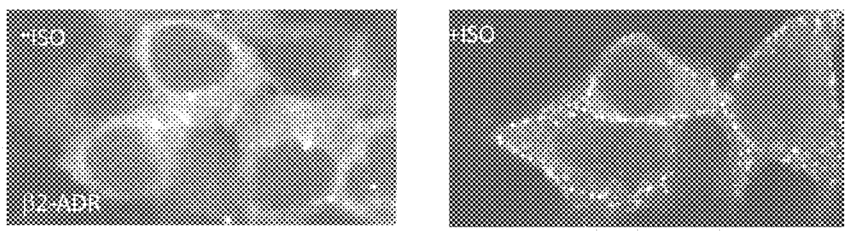

To understand the mechanism of action of LGR4-6 in potentiating Wnt/β-catenin signaling and because as LGR4-6 are predicted to be members of the GPCR superfamily based on their amino acid sequences, the possible coupling of LGR4-6 to heterotrimeric G proteins and/or to β-arrestin was investigated. For cAMP assays, HEK293T cells were transiently transfected with vector, HA-LGR4, Myc-LGR5, and FLAG-LGR6 using Fugene 6. Next day, the cells were harvested and cAMP responses were measured with the AlphaScreen® cAMP assay kit (Perkin Elmer) according to the manufacturer's suggested protocol. RSPO1 and RSPO2 were diluted in 3× serial dilutions in the stimulation buffer. Forskolin was used a positive control for cAMP production. For $Ca^{2+}$ mobilization assays, HEK293T cells were transfected as above, and then seeded into poly-D-lysine coated black/clear bottom 96-well plates next day. After overnight culturing, the cells were loaded with Calicium 5 (Molecular Devices) according to the manufacturer's protocol and incubated at 37° C. for 1 hr in a $CO_2$ incubator. RSPO1 and ATP were prepared in hanks-balanced salt solutions (HBSS)+0.5% BSA. Fluorescence intensity was measured every 3 sec for 6 min using a Tecan M1000 plate reader with excitation at 485 nm and emission at 525 nm. RSPO1 and ATP were injected at 30 sec. and 3 min., respectively, after the initiation of fluorescence reading. In all cases, receptor expression was verified by immunoblotting analysis. No activation was detected in any of the three classic pathways of G proteins in HEK293T cells with or without the over-expression of LGR4-6 following treatment with various concentrations of RSPOs (FIG. 9A-E). Co-treatment with Wnt3a did not cause any difference For the β-arrestin translocation assay, HEK293T cells were transiently transfected with β-arrestin2-GFP plus vector (SEQ ID NO: 52; SEQ ID NO: 53), Myc-LGR4, Myc-LGR5, or FLAG-LGR6 as above, and then seeded into poly-D-lysine coated 8-well slides (Becton-Dickenson). After overnight culturing, the cells were washed once with OPTI-MEM®, and incubated with mRSPO1-Fc diluted by 1:100 in OPTI-MEM®+0.2% BSA or buffer alone for 45 min at room temperature. The cells were then washed 3× with PBS, fixed for 10 min at room temperature in 4% paraformaldehyde/PBS, washed 2× with PBS, and permeabalized with 0.1% saponin in PBS for 10 min. The cells were washed once with PBS and stained with Alexa Fluor® 647-labeled anti-mouse IgG2a plus Cy3-anti-MyC (LGR4 and LGR5 cells) or Cy3-anti-FLAG (LGR6 cells) for 1 hr at room temperature. The cells were washed 3× with PBS and mounted for confocal microscopy. No indication of β-arrestin translocation was observed under any circumstances, while receptor expression and ligand-receptor co-localization were clearly confirmed (FIG. 10A). As a positive control, robust translocation was observed in cells over-expressing the β2 adrenergic receptor and treated with isoproterenol (FIG. 10B). These data indicate that LGR4-6, despite having significant homology to the rhodopsin type of GPCRs in the TM regions, are coupled neither to G proteins nor to β-arrestin, at least when they are stimulated by the R-spondins.

REFERENCES CITED

The following references, to the extent that they provide exemplary procedural or other details supplementary to those set forth herein, are specifically incorporated herein by reference.

U.S. Patent Documents

US Patent Publication No. US 2009/0074782, dated Mar. 19, 2009, with A. Gurney, listed as the inventor;

US Patent Publication No. US 2009/0191205, dated Jul. 30, 2009, with A. Gurney, listed as the inventor;

International Patent Publication WO 2009/005809, dated Jan. 8, 2009, with A. Gurney listed as the inventor;

International Patent Publication WO 2010/016766, dated Feb. 11, 2010, with J. C. Clevers, et al., listed as the inventors;

Non-Patent Documents

Andreu P, et al. (2005) Crypt-restricted proliferation and commitment to the Paneth cell lineage following Ape loss in the mouse intestine. *Development* 132:1443-1451.

Barak L S, et al. (1997) A beta-arrestin/green fluorescent protein biosensor for detecting G protein-coupled receptor activation J Biol. Chem. 272(44):27497-500.

Barker N, et al. (2007) Identification of stem cells in small intestine and colon by marker gene Lgr5. *Nature* 449: 1003-1007.

Barker, N., et al. (2009) Crypt stem cells as the cells-of-origin of intestinal cancer, *Nature* 457, 608-611.

Bhanja, P. et al. (2009) Protective Role of R-spondin1, and Intestinal Stem Cell Growth Factor, against Radiation-Induced Gastrointestinal Syndrome in Mice PLoS ONE 4(11):e8014.

Bilic J, et al. (2007) Wnt induces LRP6 signalosomes and promotes dishevelled-dependent LRP6 phosphorylation. *Science* 316:1619-1622.

Binnerts M E, et al. (2007) R-Spondin1 regulates Wnt signaling by inhibiting internalization of LRP6. *Proc Natl Acad Sci USA* 104:14700-14705.

Blitzer J T & Nusse R (2006) A critical role for endocytosis in Wnt signaling. *BMC Cell Biol* 7:28.

Bohn, L. M., and McDonald, P. H. (2010) Seeking Ligand Bias: Assessing GPCR Coupling to Beta-Arrestins for Drug Discovery *Drug Discov Today Technol.* 7(1): e37-e42.

Dick, J. E. (2008) Stem cell concepts renew cancer research, *Blood* 112, 4793-4807.

Gao Y, et al. (2006) Up-regulation of GPR48 induced by down-regulation of p27Kip1 enhances carcinoma cell invasiveness and metastasis. *Cancer Res* 66:11623-11631.

Garcia M I, et al. (2009) LGR5 deficiency deregulates Wnt signaling and leads to precocious Paneth cell differentiation in the fetal intestine. *Dev Biol* 331:58-67.

Haegebarth, A., and Clevers, H. (2009) Wnt signaling, lgr5, and stem cells in the intestine and skin, *Am J Pathol* 174, 715-721.

Harada N, et al. (1999) Intestinal polyposis in mice with a dominant stable mutation of the beta-catenin gene. *EMBO J* 18:5931-5942.

Hermey G, Methner A, Schaller H C, & Hermans-Borgmeyer 1 (1999) Identification of a novel seven-transmembrane receptor with homology to glycoprotein receptors and its expression in the adult and developing mouse. *Biochem Biophys Res Comun* 254:273-279.

Hoshii T, et al. (2007) LGR4 regulates the postnatal development and integrity of male reproductive tracts in mice. *Biol Reprod* 76:303-313.

Hsu S Y, et al. (2000) The three subfamilies of leucine-rich repeat-containing G protein-coupled receptors (LGR): identification of LGR6 and LGR7 and the signaling mechanism for LGR7. *Mol Endocrinol* 14:1257-1271.

Hsu S Y, Liang S G, & Hsueh A J (1998) Characterization of two LGR genes homologous to gonadotropin and thyrotropin receptors with extracellular leucine-rich repeats and a G protein-coupled, seven-transmembrane region. *Mol Endocrinol* 12:1830-1845.

Jaks V, et al. (2008) Lgr5 marks cycling, yet long-lived, hair follicle stem cells. *Nat Genet.* 40:1291-1299.

Kato S, et al. (2006) Leucine-rich repeat-containing G protein-coupled receptor-4 (LGR4, Gpr48) is essential for renal development in mice. *Nephron Exp Nephrol* 104:e63-75.

Kazanskaya O, et al. (2004) R-Spondin2 is a secreted activator of Wnt/beta-catenin signaling and is required for *Xenopus* myogenesis. *Dev Cell* 7:525-534.

Kim K A, et al. (2005) Mitogenic influence of human R-spondin1 on the intestinal epithelium. *Science* 309:1256-1259.

Kim K A, et al. (2006) R-Spondin proteins: a novel link to beta-catenin activation. *Cell Cycle* 5:23-26.

Kim K A, et al. (2008) R-Spondin family members regulate the Wnt pathway by a common mechanism. *Mol Biol Cell* 19:2588-2596.

Lefkowitz R J & Shenoy S K (2005) Transduction of receptor signals by beta-arrestins. *Science* 308:512-517.

Logan, C. Y., and Nusse, R. (2004) The Wnt signaling pathway in development and disease, *Annu Rev Cell Dev Biol* 20, 781-810.

Luo J, et al. (2009) Regulation of bone formation and remodeling by G-protein-coupled receptor 48. *Development* 136: 2747-2756.

Mazerbourg S, et al. (2004) Leucine-rich repeat-containing, G protein-coupled receptor 4 null mice exhibit intrauterine growth retardation associated with embryonic and perinatal lethality. *Mol Endocrinol* 18:2241-2254.

McClanahan T, et al. (2006) Identification of overexpression of orphan G protein-coupled receptor GPR49 in human colon and ovarian primary tumors. *Cancer Biol Ther* 5:419-426.

McDonald T, et al. (1998) Identification and cloning of an orphan G protein-coupled receptor of the glycoprotein hormone receptor subfamily. *Biochem Biophys Res Commun* 247:266-270.

Mendive F, et al. (2006) Defective postnatal development of the male reproductive tract in LGR4 knockout mice. *Dev Biol* 290:421-434.

Mimeault, M., et al. (2007) Recent advances in cancer stem/progenitor cell research: therapeutic implications for overcoming resistance to the most aggressive cancers, *J Cell Mol Med* 11, 981-1011.

Mohri Y, Kato S, Umezawa A, Okuyama R, & Nishimori K (2008) Impaired hair placode formation with reduced expression of hair follicle-related genes in mice lacking Lgr4. *Dev Dyn* 237:2235-2242.

Morita H, et al. (2004) Neonatal lethality of LGR5 null mice is associated with ankyloglossia and gastrointestinal distension. *Mol Cell Biol* 24:9736-9743.

Nam J S, Turcotte T J, Smith P F, Choi S, & Yoon J K (2006) Mouse cristin/R-spondin family proteins are novel ligands for the Frizzled 8 and LRP6 receptors and activate beta-catenin-dependent gene expression. *J Biol Chem* 281: 13247-13257.

Ootani A, et al. (2009) Sustained in vitro intestinal epithelial culture within a Wnt-dependent stem cell niche. *Nat Med* 15:701-706.

Polakis, P. (2007) The many ways of Wnt in cancer, *Curr Opin Genet Dev* 17, 45-51.

Reya, T., et al. (2003) A role for Wnt signalling in self-renewal of haematopoietic stem cells, *Nature* 423. 409-414.

Sato T, et al. (2011) Paneth cells constitute the niche for Lgr5 stem cells in intestinal crypts. *Nature* 469:415-418.

Taelman V F, et al. (2010) Wnt signaling requires sequestration of glycogen synthase kinase 3 inside multivesicular endosomes. *Cell* 143:1136-1148.

Tan, B. T., et al. (2006) The cancer stem cell hypothesis: a work in progress, *Lab Invest* 86, 1203-1207.

Tanese K, et al. (2008) G-protein-coupled receptor GPR49 is up-regulated in basal cell carcinoma and promotes cell proliferation and tumor formation. *Am J Pathol* 173:835-843.

Veeman M T, Slusarski D C, Kaykas A. Louie S H. & Moon R T (2003) Zebrafish prickle, a modulator of noncanonical Wnt/Fz signaling, regulates gastrulation movements. *Curr Biol* 13:680-685.

Veeman, M. T. et al. (2003) Curr Biol 13, 680.

Vermeulen, L., et al. (2010) Wnt activity defines colon cancer stem cells and is regulated by the microenvironment, *Nat Cell Biol* 12, 468-476.

Wang, Y., et al. (2010) The Wnt/beta-catenin pathway is required for the development of leukemia stem cells in AML, *Science* 327, 1650-1653.

Wei Q, et al. (2007) R-spondin1 is a high affinity ligand for LRP6 and induces LRP6 phosphorylation and beta-catenin signaling. *J Biol Chem* 282:15903-15911.

Wend, P., et al. (2010) Wnt signaling in stem and cancer stem cells, *Semin Cell Dev Biol* 21. 855-863.

Weng J, et al. (2008) Deletion of G protein-coupled receptor 48 leads to ocular anterior segment dysgenesis (ASD) through down-regulation of Pitx2. *Proc Natl Acad Sci USA* 105:6081-6086.

Yamashita R, et al. (2009) Defective development of the gall bladder and cystic duct in Lgr-4-hypomorphic mice. *Dev Dyn* 238:993-1000.

Zeng, Y. A., and Nusse, R. (2010) Wnt proteins are self-renewal factors for mammary stem cells and promote their long-term expansion in culture, *Cell Stem Cell* 6, 568-577.

Zhao J, et al. (2007) R-spondin 1, a novel intestinotrophic mitogen, ameliorates experimental colitis in mice. *Gastroenterology* 132:1331-1343.

What is claimed:

1. A method for identifying a compound having an ability to modulate activity of a receptor in a cell comprising the steps of:

(a) contacting the compound with the receptor, the receptor having β-catenin activity and greater than 80% homology to an amino acid sequence encoded by the nucleic acid sequence SEQ ID NO:14;

(b) determining if the activity of the receptor is modulated by measuring β-catenin activity in the cell; and (c) identifying the compound as a compound having an ability to modulate activity of the receptor in the cell if β-catenin activity in the cell is greater than the β-catenin activity in a cell which has not been exposed to the compound.

2. The method of claim 1, wherein the cell is transfected with a β-catenin reporter plasmid carrying firefly luciferase and a control plasmid carrying renilla luciferase, and wherein the measuring β-catenin activity in the cell is by measuring firefly luciferase activity and renilla luciferase activity in the cell, and wherein the compound is identified as a compound having an ability to modulate activity of the receptor in the cell if firefly luciferase activity exceeds renilla luciferase activity in the cell.

3. The method of claim 2, wherein the β-catenin reporter plasmid has the sequence SEQ ID NO:45.

4. The method of claim 2, wherein the control plasmid has the sequence SEQ ID NO:54.

* * * * *